(12) United States Patent
Zimmermann et al.

(10) Patent No.: US 7,767,704 B2
(45) Date of Patent: Aug. 3, 2010

(54) ANTIVIRAL 4-AMINOCARBONYLAMINO-SUBSTITUTED IMIDAZOLE COMPOUNDS

(75) Inventors: Holger Zimmermann, Wuppertal (DE); David Brueckner, Essen (DE); Dirk Heimbach, Duesseldorf (DE); Martin Hendrix, Odenthal (DE); Kerstin Henninger, Wuppertal (DE); Guy Hewlett, Wuppertal (DE); Ulrich Rosentreter, Binnen (DE); Joerg Keldenich, Wuppertal (DE); Dieter Lang, Velbert (DE); Martin Radtke, Erkrath (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 329 days.

(21) Appl. No.: 10/594,343

(22) PCT Filed: Mar. 11, 2005

(86) PCT No.: PCT/EP2005/002571

§ 371 (c)(1),
(2), (4) Date: Jul. 23, 2007

(87) PCT Pub. No.: WO2005/092865

PCT Pub. Date: Oct. 6, 2005

(65) Prior Publication Data

US 2008/0004275 A1    Jan. 3, 2008

(30) Foreign Application Priority Data

Mar. 26, 2004  (DE) ............... 10 2004 015 007

(51) Int. Cl.
*A61K 31/4164* (2006.01)
*C07D 233/54* (2006.01)

(52) U.S. Cl. ............................ 514/400; 548/326.5
(58) Field of Classification Search ............ 548/300.1, 548/326.5, 333.5, 335.1; 514/400
See application file for complete search history.

(56) References Cited

U.S. PATENT DOCUMENTS

2008/0176859 A1    7/2008  Zimmermann et al.

FOREIGN PATENT DOCUMENTS

| CA | 2 508 788 | 6/2004 |
|----|-----------|--------|
| WO | WO-98/52558 | 11/1998 |
| WO | 9923091 | 5/1999 |
| WO | 0034261 | 6/2000 |
| WO | 0042043 | 7/2000 |
| WO | WO-2004/052852 | 6/2004 |
| WO | WO-2005/092865 | 10/2005 |
| WO | WO-2006/089664 | 8/2006 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
"HIV-AIDS." Retrieved online via Internet [Mar. 25, 2009], URL: http://www.mayoclinic.com/health/hiv-aids/DS00005.*
Chong et al., Abstracts of 39th Interscience Conference on Antimicrobial Agents and Chemotherapy, 1999, p. 441.
Cinatl Jr. et al., FEMS Microbiology Reviews (2004) 28:59-77.
Kraemer et al., Cancer Research (1983) 43:4822-4827.
PCT Patent No. WO 2005/092865, International Publication Date: Oct. 6, 2005 (English abstract only).
English translation of the International Preliminary Report on Patentability for PCT/EP2006/001325, mailed Sep. 20, 2007, 8 pages.
Chaimbault et al., Pharmacy and Pharmacology Communications (1999) 5(3):211-215.

* cited by examiner

*Primary Examiner*—Kamal A Saeed
*Assistant Examiner*—Samantha L Shterengarts
(74) *Attorney, Agent, or Firm*—Morrison & Foerster, LLP

(57) ABSTRACT

The invention relates to the substituted imidazoles of formula (I) and to methods for producing the same, to their use in the treatment and/or prophylaxis of diseases and to their use for producing drugs for use in the treatment and/or prophylaxis of diseases, especially for use as antiviral agents, especially against cytomegaloviruses.

7 Claims, No Drawings

ANTIVIRAL 4-AMINOCARBONYLAMINO-SUBSTITUTED IMIDAZOLE COMPOUNDS

The invention relates to substituted imidazoles and processes for their preparation, to their use for the treatment and/or prophylaxis of diseases and to their use for the production of medicaments for the treatment and/or prophylaxis of diseases, in particular for use as antiviral agents, in particular against cytomegaloviruses.

WO 99/23091 describes aromatic heterocyclic compounds as antiinflammatory agents which may be suitable inter alia also for the treatment of viral infections.

Although agents having an antiviral effect but having different types of structures are available on the market, the therapies currently available with ganciclovir, valganciclovir, foscarnet and cidofovir are associated with serious side effects, e.g. nephrotoxicity, neutropenia or thrombocytopenia. It is moreover always possible for resistance to develop. Novel agents for effective therapy are therefore desirable.

One object of the present invention is therefore to provide novel compounds with the same or improved antiviral effect for the treatment of viral infectious diseases in humans and animals.

It has surprisingly been found that the substituted imidazoles described in the present invention have high antiviral activity.

The present invention relates to compounds of the formula

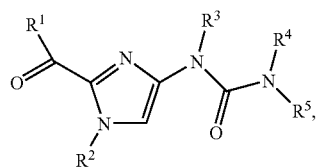

(I)

in which
$R^1$ is —$OR^6$ or —$NR^7R^8$,
$R^2$ is $C_1$-$C_6$-alkyl or $C_1$-$C_6$-alkenyl,
  where alkyl and alkenyl may be substituted by 1 to 3 substituents, where the substituents are selected independently of one another from the group consisting of halogen, $C_1$-$C_6$-alkoxy, $C_3$-$C_8$-cycloalkyl, 5- to 10-membered heterocyclyl, $C_6$-$C_{10}$-aryl, phenoxy and 5- to 10-membered heteroaryl,
    in which cycloalkyl, heterocyclyl, aryl, phenoxy and heteroaryl may be substituted by 1 to 3 substituents, where the substituents are selected independently of one another from the group consisting of halogen, hydroxy, oxo, nitro, cyano, trifluoromethyl, difluoromethyl, trifluoromethoxy, difluoromethoxy, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylaminocarbonyl and phenyl,
$R^3$ and $R^4$ are independently of one another hydrogen or $C_1$-$C_6$-alkyl,
$R^5$ is phenyl,
  where phenyl may be substituted by 1 to 3 substituents, where the substituents are selected independently of one another from the group consisting of halogen, hydroxy, trifluoromethyl, difluoromethyl, trifluoromethoxy, difluoromethoxy, $C_1$-$C_6$-alkyl and $C_1$-$C_6$-alkoxy,
$R^6$ is $C_1$-$C_6$-alkyl,
  where alkyl may be substituted by 1 to 3 substituents, where the substituents are selected independently of one another from the group consisting of halogen, cyano, hydroxy, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclyl, 5- to 7-membered heterocyclylcarbonyl, $C_6$-$C_{10}$-aryl and 5- to 10-membered heteroaryl,
    in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, nitro, cyano, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
    and
    in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_8$-cycloalkylamino and 5- to 7-membered heterocyclyl,
      in which heterocyclyl in turn may be substituted by 1 to 3 substituents, where the substituents are selected independently of one another from the group consisting of $C_1$-$C_4$-alkyl and oxo,
$R^7$ is hydrogen or $C_1$-$C_6$-alkyl,
and
$R^8$ is $C_1$-$C_6$-alkyl,
  where alkyl may be substituted by 1 to 3 substituents, where the substituents are selected independently of one another from the group consisting of halogen, cyano, hydroxy, trifluoromethyl, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclyl, 5- to 7-membered heterocyclylcarbonyl, $C_6$-$C_{10}$-aryl, $C_6$-$C_{10}$-arylamino, 5- to 10-membered heteroaryl and 5- to 10-membered heteroarylamino,
    in which alkoxy and alkylamino may be substituted by 1 to 3 substituents, where the substituents are selected independently of one another from the group consisting of halogen, hydroxy and $C_1$-$C_6$-alkoxy,
    and
    in which cycloalkyl, cycloalkylamino, heterocyclyl, heterocyclylcarbonyl, aryl, arylamino, heteroaryl and heteroarylamino may be substituted by 1 to 3 substituents, where the substituents are selected independently of one another from the group consisting of halogen, hydroxy, oxo, nitro, cyano, trifluoromethyl, difluoromethyl, trifluoromethoxy, difluoromethoxy, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl,
    and
    in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_8$-cycloalkylamino and 5- to 7-membered heterocyclyl, in which heterocyclyl in turn may be substituted by 1 to 3 substituents, where the substituents are selected independently of one another from the group consisting of $C_1$-$C_4$-alkyl and oxo, and the salts thereof, the solvates thereof and the solvates of the salts thereof.

Compounds of the invention are the compounds of the formula (I) and the salts, solvates and solvates of the salts thereof; the compounds which are encompassed by formula (I) and have the formulae (Ia), (Ib), (c) and (Id) mentioned hereinafter, and the compounds which are encompassed by formula (I) and are mentioned hereinafter as exemplary embodiment(s), and the salts, solvates and solvates of the salts thereof, where the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds of the invention can exist in tautomeric forms, the present invention includes all tautomeric forms.

Salts preferred for the purposes of the present invention are physiologically acceptable salts of the compounds of the invention. However, salts which are not themselves suitable for pharmaceutical applications but can be used for example for isolating or purifying the compounds of the invention are also included.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state by coordination with solvent molecules. Hydrates are a special form of solvates in which the coordination takes place with water.

In addition, the present invention also encompasses prodrugs of the compounds of the invention. The term "prodrugs" encompasses compounds which themselves may be biologically active or inactive but are converted (for example by a metabolism or hydrolysis) into compounds of the invention during their residence time in the body.

For the purposes of the present invention, unless specified otherwise, the substituents have the following meaning:

Alkyl per se and "alk" and "alkyl" in alkoxy, alkylamino, alkylcarbonyl, alkylcarbonyloxy alkoxycarbonyl, alkoxycarbonylamino, alkylaminocarbonyl and alkylcarbonylamino are a linear or branched alkyl radical having normally 1 to 6 ("$C_1$-$C_6$-alkyl"), preferably 1 to 4, particularly preferably 1 to 3, carbon atoms, by way of example and preferably methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylamino is an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. ($C_1$-$C_3$)-Alkylamino is for example a monoalkylamino radical having 1 to 3 carbon atoms or a dialkylamino radical having in each case 1 to 3 carbon atoms per alkyl substituent.

Alkylcarbonyl is by way of example and preferably acetyl and propanoyl.

Alkylcarbonyloxy is by way of example and preferably methylcarbonyloxy, ethylcarbonyloxy, n-propylcarbonyloxy, isopropylcarbonyloxy, tert-butylcarbonyloxy, n-pentylcarbonyloxy and n-hexylcarbonyloxy.

Alkoxycarbonyl is by way of example and preferably methoxycarbonyl, ethoxycarbonyl, n-propoxycarbonyl, isopropoxycarbonyl, tert-butoxycarbonyl, n-pentoxycarbonyl and n-hexoxycarbonyl.

Alkoxycarbonylamino is by way of example and preferably methoxycarbonylamino, ethoxycarbonylamino, n-propoxycarbonylamino, isopropoxycarbonylamino, tert-butoxycarbonylamino, n-pentoxycarbonylamino and n-hexoxycarbonylamino.

Alkylaminocarbonyl is an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. ($C_1$-$C_3$)-Alkylaminocarbonyl is for example a monoalkylaminocarbonyl radical having 1 to 3 carbon atoms or a dialkylaminocarbonyl radical having in each case 1 to 3 carbon atoms per alkyl substituent.

Alkylcarbonylamino is by way of example and preferably methylcarbonylamino, ethylcarbonylamino, n-propylcarbonylamino, isopropylcarbonylamino, tert-butylcarbonylamino, n-pentylcarbonylamino and n-hexylcarbonylamino.

Aryl is a mono- to tricyclic aromatic carbocyclic radical having normally 6 to 14 carbon atoms, by way of example and preferably phenyl, naphthyl and phenanthrenyl.

Arylamino is a mono- to tricyclic aromatic, carbocyclic radical having normally 6 to 14 carbon atoms which is linked via an amino group. The second substituent on the amino group is hydrogen or $C_1$-$C_6$-alkyl. Mention may be made by way of example and preferably of: phenylamino, phenylmethylamino, naphthylamino and phenanthrenylamino.

5- to 10-membered heteroaryl for the purposes of the present invention is generally an aromatic, mono- or bicyclic radical having 5 to 10 ring atoms and up to 5 heteroatoms from the series S, O and/or N. 5- to 6-membered heteroaryls having up to 4 heteroatoms are preferred. The heteroaryl radical may be bonded via a carbon atom or heteroatom. Mention may be made by way of example and preferably of: thienyl, furyl, pyrrolyl, thiazolyl, oxazolyl, pyrazolyl, imidazolyl, pyridyl, pyrimidyl, pyridazinyl, indolyl, indazolyl, benzofuranyl, benzothiophenyl, quinolinyl and isoquinolinyl.

5- to 10-membered heteroarylamino is for the purposes of the invention generally an aromatic mono- or bicyclic radical having 5 to 10 ring atoms and up to 5 heteroatoms from the series S, O and/or N, which is linked via an amino group. 5- to 6-membered heteroaryls having up to 4 heteroatoms are preferred. The heteroaryl radical is linked via a carbon atom to the amine. The second substituent on the amino group is hydrogen or $C_1$-$C_6$-alkyl. Mention may be made by way of example and preferably of: thienylamino, furylamino, pyrrolylamino, thiazolylamino, oxazolylamino, pyrazolylamino, imidazolylamino, pyridylamino, pyrimidylamino, pyridazinylamino, indolylamino, indazolylamino, benzofuranylamino, benzothiophenylamino, quinolinylamino and isoquinolinylamino.

Cycloalkyl is a cycloalkyl group having normally 3 to 8, preferably 3 to 6, carbon atoms, by way of example and preferably cyclopropyl, cyclobutyl, cyclopentyl, cyclohexyl and cycloheptyl.

Cycloalkylamino is a cycloalkylamino group having normally 3 to 8, preferably 3 to 6, carbon atoms, by way of example and preferably cyclopropylamino, cyclobutylamino, cyclopentylamino, cyclohexylamino and cycloheptylamino.

5- to 10-membered heterocyclyl is for the purposes of the invention a mono- or bicyclic, saturated or partially unsaturated heterocycle having up to three heteroatoms from the series N, O and/or S, which is linked via ring carbon atom or a nitrogen atom of the heterocycle. Mention may be made by way of example and preferably of: tetrahydrofuryl, dihydrofuryl, imidazolidinyl, thiolanyl, dioxolanyl, pyrrolidinyl, pyrrolinyl, tetrahydropyranyl, dihydropyranyl, piperidinyl, piperazinyl, morpholinyl, thiomorpholinyl, 7-oxabicyclo[2.2.1]heptanyl and 7-oxabicyclo[2.2.1]hept-5-enyl.

5- to 10-membered heterocyclylcarbonyl is for the purposes of the invention a mono- or bicyclic, saturated or partially unsaturated heterocycle which is linked via a carbonyl group, having up to three heteroatoms from the series N, O and/or S, which is linked via a ring carbon atom or a nitrogen atom of the heterocycle to the carbonyl group. Mention may be made by way of example and preferably of: tetrahydrofurylcarbonyl, dihydrofurylcarbonyl, imidazolidinylcarbonyl, thiolanylcarbonyl, dioxolanylcarbonyl, pyrrolidinylcarbonyl, pyrrolinylcarbonyl, tetrahydropyranylcarbonyl, dihydropyranylcarbonyl, piperidinylcarbonyl, piperazinylcarbonyl, morpholinylcarbonyl, thiomorpholinylcarbonyl, 7-oxabicyclo[2.2.1]heptanylcarbonyl and 7-oxabicyclo[2.2.1]hept-5-enylcarbonyl.

A 4- to 8-membered heterocycle having at least one ring nitrogen atom is for the purposes of the invention a saturated or partially unsaturated, monocyclic heterocycle which may comprise up to two further heteroatoms from the series, N, O and/or S and is linked via a ring nitrogen atom of the heterocycle. A 5- to 7-membered, saturated, monocyclic N-heterocycle which may comprise a second nitrogen atom or an oxygen atom as further heteroatom is preferred. Mention may be made by way of example and preferably of: pyrrolidinyl, pyrrolinyl, oxazolidinyl, thiazolidinyl, piperidinyl, piperazinyl, morpholinyl, thiomorpholinyl, hexahydroazepinyl, hexahydro-1,4-diazepinyl, octahydroazocinyl.

Halogen is fluorine, chlorine, bromine or iodine.

A symbol * on a carbon atom means that, in relation to the configuration of this carbon atom, the compound is in enantiopure form, by which is meant for the purposes of the present invention an enantiomeric excess of more than 90% (>90% ee).

Preference is given for the purposes of the present invention to compounds of the formula (I)

in which $R^1$ is —$OR^6$ or —$NR^7R^8$, $R^2$ is $C_1$-$C_6$-alkyl or $C_1$-$C_6$-alkenyl, where alkyl and alkenyl may be substituted by 1 to 3 substituents, where the substituents are selected independently of one another from the group consisting of halogen, $C_1$-$C_6$-alkoxy, $C_3$-$C_8$-cycloalkyl, 5- to 10-membered heterocyclyl, $C_6$-$C_{10}$-aryl, phenoxy and 5- to 10-membered heteroaryl, in which cycloalkyl, heterocyclyl, aryl, phenoxy and heteroaryl may be substituted by 1 to 3 substituents, where the substituents are selected independently of one another from the group consisting of halogen, hydroxy, oxo, nitro, cyano, trifluoromethyl, trifluoromethoxy, $C_1$-$C_6$-alkyl, $C_1$-$C_6$alkoxy, hydroxycarbonyl, $C_1$-$C_6$-alkoxycarbonyl, amino, $C_1$-$C_6$-alkylamino, aminocarbonyl, $C_1$-$C_6$-alkylaminocarbonyl and phenyl, $R^3$ and $R^4$ are independently of one another hydrogen or $C_1$-$C_6$-alkyl, $R^5$ is phenyl, where phenyl may be substituted by 1 to 3 substituents, where the substituents are selected independently of one another from the group consisting of halogen, hydroxy, trifluoromethyl, trifluoromethoxy, $C_1$-$C_6$-alkyl and $C_1$-$C_6$-alkoxy, $R^6$ is $C_1$-$C_6$-alkyl, where alkyl may be substituted by 1 to 3 substituents, where the substituents are selected independently of one another from the group consisting of halogen, cyano, hydroxy, $C_1$-$C_6$-alkoxy, hydroxycarbonyl, $C_1$-$C_6$-alkylcarbonyloxy, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclylcarbonyl, 5- to 7-membered heterocyclylcarbonyl, $C_6$-$C_{10}$-aryl and 5- to 10-membered heteroaryl, in which cycloalkyl, cycloalkylamino, heterocyclyl, heterocyclylcarbonyl, aryl und heteroaryl may be substituted by 1 to 3 substituents, where the substituents are selected independently of one another from the group consisting of halogen, hydroxy, nitro, cyano, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_8$-cycloalkylamino and 5- to 7-membered heterocyclyl, in which heterocyclyl in turn may be substituted by 1 to 3 substituents, where the substituents are selected independently of one another from the group consisting of $C_1$-$C_4$-alkyl and oxo, $R^7$ is hydrogen or $C_1$-$C_6$-alkyl, and $R^8$ $C_1$-$C_6$-alkyl, where alkyl may be substituted by 1 to 3 substituents, where the substituents are selected independently of one another from the group consisting of halogen, cyano, hydroxy, trifluoromethyl, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclyl, 5- to 7-membered heterocyclylcarbonyl, $C_6$-$C_{10}$-aryl and 5- to 10-membered heteroaryl, in which alkoxy and alkylamino may be substituted by 1 to 3 substituents, where the substituents are selected independently of one another from the group consisting of halogen, hydroxy and $C_1$-$C_6$-alkoxy, and in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, oxo, nitro, cyano, trifluoromethyl, trifluoromethoxy, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl und $C_1$-$C_6$-alkylaminocarbonyl, and in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_8$-cycloalkylamino and 5- to 7-membered heterocyclyl, in which heterocyclyl may in turn be substituted by 1 to 3 substituents, where the substituents are selected independently of one another from the group consisting of $C_1$-$C_4$-alkyl and oxo, and the salts thereof, the solvates thereof, and the solvates of the salts thereof.

Preference is also given for the purposes of the present invention to compounds of the formula (I), in which $R^1$ is —$OR^6$ or —$NR^7R^8$, $R^2$ is $C_1$-$C_4$-alkyl or $C_1$-$C_5$-alkenyl, where alkyl and alkenyl may be substituted by 1 to 2 substituents, where the substituents are selected independently of one another from the group consisting of halogen, $C_1$-$C_4$-alkoxy, $C_3$-$C_6$-cycloalkyl, phenyl and phenoxy, in which cycloalkyl, phenyl and phenoxy may be substituted by 1 to 3 substituents, where the substituents are selected independently of one another from the group consisting of halogen, hydroxy, cyano, trifluoromethyl, trifluoromethoxy, $C_1$-$C_4$-alkyl, $C_1$-$C_4$-alkoxy, hydroxycarbonyl, $C_1$-$C_4$-alkoxycarbonyl, amino, $C_1$-$C_6$-alkylamino, aminocarbonyl, $C_1$-$C_6$-alkylaminocarbonyl and phenyl, $R^3$ and $R^4$ are hydrogen, $R^5$ is phenyl, where phenyl may be substituted by 1 to 3 substituents, where the substituents are selected independently of one another from the group consisting of halogen, hydroxy, trifluoromethyl, trifluoromethoxy, $C_1$-$C_4$-alkyl and $C_1$-$C_4$-alkoxy, $R^6$ is $C_1$-$C_5$-alkyl, where alkyl may be substituted by 1 to 3 substituents, where the substituents are selected independently of one another from the group consisting of halogen, cyano, hydroxy, $C_1$-$C_4$-alkoxy, hydroxycarbonyl, amino, $C_1$-$C_6$-alkylamino, aminocarbonyl, $C_1$-$C_4$-alkylcarbonyloxy, $C_1$-$C_4$-alkylcarbonylamino, $C_1$-$C_6$-alkylaminocarbonyl, $C_1$-$C_4$-alkoxycarbonylamino, $C_3$-$C_7$-cycloalkyl, $C_3$-$C_7$-cycloalkylamino, 5- to 7-membered heterocyclyl, 5- to 7-membered heterocyclylcarbonyl, $C_6$-$C_{10}$-aryl and 5- to 10-membered heteroaryl, in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, cyano, $C_1$-$C_4$-alkyl, $C_1$-$C_4$-alkoxy, hydroxycarbonyl, $C_1$-$C_4$-alkoxycarbonyl, amino, $C_1$-$C_6$-alkylamino, aminocarbonyl and $C_1$-$C_6$-alkylaminocarbonyl, and in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_7$-cycloalkylamino and 5- to 7-membered heterocyclyl, $R^7$ is hydrogen, and $R^8$ is $C_1$-$C_8$-alkyl, where alkyl may be substituted by 1 to 3 substituents, where the substituents are selected independently of one another from the group consisting of halogen, cyano, hydroxy, trifluoromethyl, $C_1$-$C_6$-alkoxy, hydroxycarbonyl, amino, $C_1$-$C_6$-alkylamino, aminocarbonyl, $C_1$-$C_4$-alkylcarbonyloxy, $C_1$-$C_4$-alkylcarbonylamino, $C_1$-$C_6$-alkylaminocarbonyl, $C_1$-$C_4$-alkoxycarbonylamino, $C_3$-$C_7$-cycloalkyl, $C_3$-$C_7$-cycloalkylamino, 5- to 7-membered heterocyclyl, 5- to 7-membered heterocyclylcarbonyl, $C_6$-$C_{10}$-aryl and 5- to 10-membered heteroaryl, in which alkoxy and alkylamino may be substituted by 1 to 3 substituents, where the substituents are selected independently of one another from the group consisting of halogen, hydroxy and $C_1$-$C_4$— alkoxy, and in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, oxo, cyano, trifluoromethyl, $C_1$-$C_4$-alkyl, $C_1$-$C_4$-alkoxy, hydroxycarbonyl, $C_1$-$C_4$-alkoxycarbonyl, amino, $C_1$-$C_6$-alkylamino, aminocarbonyl and $C_1$-$C_6$-alkylaminocarbonyl, and in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_7$-cycloalkylamino and 5- to 7-membered heterocyclyl, in which heterocyclyl in turn may be substituted by 1 to 3 substituents, where the substituents are selected independently of one another from the group consisting of $C_1$-$C_4$-alkyl and oxo, and the salts thereof, the solvates thereof and the solvates of the salts thereof.

Preference is also given for the purposes of the present invention to compounds of the formula (I)

in which $R^1$ is —$OR^6$ or —$NR^7R^8$, $R^2$ is methyl, ethyl, n-butyl, prop-2-en-1-yl or 3-methylbut-2-en-1-yl, where methyl, ethyl, n-butyl and prop-2-en-1-yl may be substituted by 1 to 2 substituents, where the substituents are selected independently of one another from the group consisting of chlorine, methoxy, cyclopropyl, phenyl and phenoxy, in which phenyl may be substituted by a substituent trifluoromethyl, $R^3$ and $R^4$ are hydrogen, $R^5$ is phenyl, where phenyl may be substituted by 1 to 3 substituents, where the substituents are selected independently of one another from the group consisting of fluorine, chlorine, trifluoromethoxy and methyl, $R^6$ is $C_1$-$C_3$-alkyl, where alkyl may be substituted by 1 to 2 substituents, where the substituents are selected independently of one another from the group consisting of halogen, cyano, hydroxy and methylcarbonyloxy, in which methylcarbonyloxy may be substituted by 1 to 3 substituents, where the substituents are selected independently of one another from the group consisting of isobutylamino, dimethylamino, diethylamino, cyclopropylamino, pyrrolidinyl and morpholinyl, $R^7$ is hydrogen, and $R^8$ is $C_1$-$C_3$-alkyl, where alkyl may be substituted by 1 to 2 substituents, where the substituents are selected independently of one another from the group consisting of halogen, cyano, hydroxy, trifluoromethyl, ethoxy, isobutylamino, dimethylamino, diethylamino, methylethylamino, aminocarbonyl, methylcarbonyloxy, propylcarbonyloxy, dimethylaminocarbonyl, diethylaminocarbonyl, ethoxycarbonylamino, cyclopropylamino, pyrrolidinyl, piperidinyl, morpholinyl, phenyl, thienyl, pyrazolyl, imidazolyl, triazolyl, pyridyl and benzimidazolyl, in which ethoxy and methylethylamino may be substituted by a substituent, where the substituent is selected from the group consisting of hydroxy and methoxy, and in which phenyl, pyrazolyl, imidazolyl, pyridyl and benzimidazolyl may be substituted by 1 to 3 substituents, where the substituents are selected independently of one another from the group consisting of methyl and methoxy, and in which methylcarbonyloxy and propylcarbonyloxy may be substituted by 1 to 3 substituents, where the substituents are selected independently of one another from the group consisting of hydroxycarbonyl, amino, isobutylamino, dimethylamino, diethylamino, cyclopropylamino, pyrrolidinyl and morpholinyl, and the salts thereof, the solvates thereof and the solvates of the salts thereof.

Preference is also given for the purposes of the present invention to compounds of the formula (I) in which $R^1$ is —$NR^7$—$R^8$.

Preference is also given for the purposes of the present invention to compounds of the formula (I) in which $R^1$ is —$OR^6$.

Preference is also given for the purposes of the present invention to compounds of the formula (I) in which $R^3$ and $R^4$ are hydrogen.

Preference is also given for the purposes of the present invention to compounds of the formula (I) in which $R^5$ is phenyl, where phenyl may be substituted by 1 to 3 substituents, where the substituents are selected independently of one another from the group consisting of fluorine, chlorine, trifluoromethoxy and methyl.

Preference is also given for the purposes of the present invention to compounds of the formula (I) in which $R^7$ is hydrogen.

The invention further relates to a process for preparing compounds of the formula (I) where in process [A]

compounds of the formula

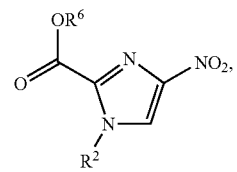

(IIa)

in which $R^6$ has the abovementioned meaning, and $R^2$ has the abovementioned meaning, are reacted in the first stage with a reducing agent, in the second stage where appropriate with compounds of the formula $$X^1—R^3 \qquad (III),$$

in which $R^3$ has the abovementioned meaning, and $X^1$ is halogen, preferably bromine or chlorine, and in the third stage in the presence of a carbonic acid derivative with compounds of the formula

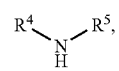

(IV)

in which $R^4$ and $R^5$ have the abovementioned meaning, to give compounds of the formula

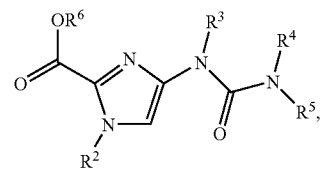

(Ia)

in which $R^6$ has the same meaning as in formula (IIa), and $R^2$, $R^3$, $R^4$ and $R^5$ have the abovementioned meaning, or in process [B]

compounds of the formula (Ia), in which $R^8$ is methyl or ethyl, are reacted in the presence of bases to give compounds of the formula

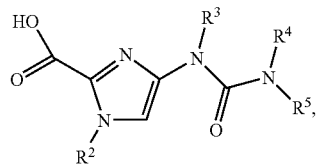
(Ib)

in which $R^2$, $R^3$, $R^4$ and $R^5$ have the abovementioned meaning, or in process [C]

compounds of the formula (Ib) are reacted with compounds of the formula

$R^1$—H    (V), in which $R^1$ has the abovementioned meaning, in the presence of dehydrating reagents to give compounds of the formula (I), or in process [D]

compounds of the formula

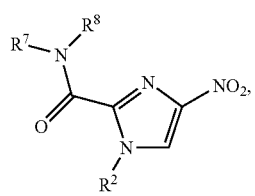
(IIb)

in which $R^2$, $R^7$ and $R^8$ have the abovementioned meaning, are reacted in the first stage with a reducing agent, in the second stage where appropriate with compounds of the formula (III)

and in the third stage in the presence of a carbonic acid derivative with compounds of the formula (IV)

to give compounds of the formula

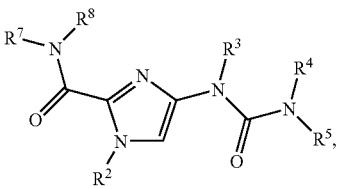
(Ic)

in which $R^2$, $R^3$, $R^4$, $R^5$, $R^7$ and $R^8$ have the abovementioned meaning, or in process [E]

compounds of the formula (IIa) or (IIb)

are reacted in the first stage with a reducing agent, in the second stage where appropriate with compounds of the formula (III)

and in the third stage with compounds of the formula

OCN—$R^5$    (VI), in which $R^5$ has the abovementioned meaning, to give compounds of the formula

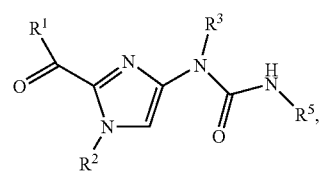
(Id)

in which $R^1$, $R^2$, $R^3$ and $R^5$ have the abovementioned meaning.

Formula (I) encompasses the compounds of the formulae (Ia), (Ib), (Ic) and (Id).

Formula (II) encompasses the compounds of the formulae (IIa) and (IIb).

The compounds of the formula (III), (IV), (V) and (VII) are known or can be synthesized from their appropriate precursors by known processes.

The following applies to processes [A], [D] and [E]:

1st Stage:

The reaction takes place generally in inert solvents, preferably in a temperature range from 0° C. to the reflux of the solvents under atmospheric pressure up to 3 bar.

Examples of reducing agents are palladium on activated carbon and hydrogen, formic acid/triethylamine/palladium on activated carbon, zinc, zinc/hydrochloric acid, iron, iron/hydrochloric acid, iron(II) sulphate/hydrochloric acid, sodium sulphide, sodium disulphide, sodium dithionite, ammonium polysulphide, sodium borohydride/nickel chloride, tin dichloride, titanium trichloride or Raney nickel and aqueous hydrazine solution, with preference for Raney nickel and aqueous hydrazine solution.

Examples of inert solvents are ethers such as diethyl ether, methyl tert-butyl ether, 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or petroleum fractions, or other solvents such as dimethylformamide, dimethylacetamide, acetonitrile or pyridine, and in the case of water-miscible solvents also mixtures thereof with water, with a preferred solvent being methanol, ethanol, isopropanol or, in the case of Raney nickel and aqueous hydrazine solution, tetrahydrofuran.

2nd Stage:

The 2nd stage is carried out for preparing compounds of the invention in which $R^3$ is $C_1$-$C_6$-alkyl and is inapplicable in the preparation of compounds of the invention in which $R^3$ is hydrogen.

The reaction takes place generally in inert solvents, where appropriate in the presence of a base, with preference in a temperature range from −20° C. to 40° C. under atmospheric pressure.

Examples of bases are amides such as sodamide, lithium hexamethyldisilazide, potassium hexamethyldisilazide, lithium diisopropylamide, or other bases such as sodium hydride, DBU or diisopropylethylamine, preferably sodamide, lithium hexamethyldisilazide, potassium hexamethyldisilazide or lithium diisopropylamide.

Examples of inert solvents are ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, ethylbenzene, xylene, toluene, preferably tetrahydrofuran or toluene.

3rd Stage of Processes [A] and [D]:

The reaction takes place generally in inert solvents, preferably in a temperature range from room temperature to 40° C. under atmospheric pressure.

Examples of carbonic acid derivatives are N,N-carbonyldiimidazole, phosgene, diphosgene, triphosgene, phenyl chloroformate or 4-nitrophenyl chloroformate, with preference for N,N-carbonyldiimidazole.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, xylene, toluene, hexane, cyclohexane or petroleum fractions, or other solvents such as ethyl acetate, acetone, dimethylformamide, dimethylacetamide, 2-butanone, dimethyl sulphoxide, acetonitrile or pyridine, and in case of water-miscible solvents also mixtures thereof with water, with preference for dimethyl sulphoxide.

3rd Stage of Process [E]:

The reaction takes place generally in inert solvents, where appropriate in the presence of a base, preferably in a temperature range from room temperature to reflux of the solvents under atmospheric pressure.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, xylene, toluene, hexane, cyclohexane or petroleum fractions, or other solvents such as ethyl acetate, acetone, dimethylformamide, dimethylacetamide, 2-butanone, dimethyl sulphoxide, acetonitrile or pyridine, with preference for tetrahydrofuran or methylene chloride.

Examples of bases are alkali metal carbonates such as caesium carbonate, sodium or potassium carbonate, or potassium tert-butoxide, or other bases such as sodium hydride, DBU, triethylamine or diisopropylethylamine, preferably triethylamine.

The following applies to process [B]:

The reaction takes place generally in inert solvents, preferably in a temperature range from 0° C. to reflux of the solvents under atmospheric pressure.

Examples of bases are alkali metal hydroxides such as sodium, lithium or potassium hydroxide, or alkali metal carbonates such as caesium carbonate, sodium or potassium carbonate, preferably sodium hydroxide.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or petroleum fractions, or other solvents such as dimethylformamide, dimethylacetamide, dimethyl sulphoxide, acetonitrile or pyridine, or mixtures of solvents with water, a preferred solvent being a mixture of ethanol and water.

The following applies to process [C]:

The reaction takes place in general in inert solvents, where appropriate in the presence of a base, preferably in a temperature range from −70° C. to 40° C. under atmospheric pressure.

Examples of suitable dehydrating reagents in this case are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)-phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)-phosphonium hexafluorophosphate (BOP), or mixtures thereof, with bases.

Examples of bases are alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine, or DBU, DBN, pyridine, with preference for triethylamine.

The condensation is preferably carried out with carbonyldiimidazole.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, hydrocarbons such as benzene, xylene, toluene, hexane, cyclohexane or petroleum fractions, or other solvents such as ethyl acetate, acetone, dimethylformamide, dimethylacetamide, 2-butanone, dimethyl sulphoxide, acetonitrile or pyridine, and in case of water-miscible solvents also mixtures thereof with water, with preference for dimethylformamide.

The compounds of the formula (II) are known or can be prepared by reacting compounds of the formula

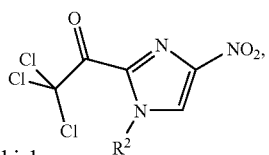
(VII)

in which
R² has the abovementioned meaning, with compounds of the formula (V).

The reaction takes place in general in inert solvents, where appropriate in the presence of a base, preferably in a temperature range from room temperature to 40° C. under atmospheric pressure.

Examples of bases are alkali metal carbonates such as caesium carbonate, sodium or potassium carbonate, or potassium tert-butoxide, or other bases such as sodium hydride, DBU, triethylamine or diisopropylethylamine, with preference for diisopropylethylamine and triethylamine.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, dioxane, tetrahydrofuran, glycol dimethyl ether or diethylene glycol dimethyl ether, alcohols such as methanol, ethanol, n-propanol, n-butanol or tert-butanol, hydrocarbons such as benzene, xylene, toluene, hexane, cyclohexane or petroleum fractions, or other solvents such as ethyl acetate, acetone, dimethylformamide, dimethylacetamide, 2-butanone, dimethyl sulphoxide, acetonitrile or pyridine, with preference for ethanol and tetrahydrofuran.

The compounds of the formula (VII) are known or can be prepared by reacting compounds of the formula

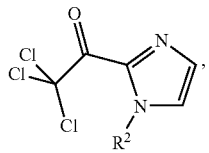
(VIII)

in which
R² has the abovementioned meaning, with fuming nitric acid, concentrated nitric acid, nitration acid or other mixing ratios of sulphuric acid and nitric acid, where appropriate in acetic anhydride as solvent, preferably in a temperature range from −60° C. to 0° C. under atmospheric pressure.

The compounds of the formula (VIII) are known or can be synthesized from the appropriate precursors by known processes.

In an alternative process, the compounds of the formula (IIa) in which R⁶ is methyl or ethyl, and R² has the abovementioned meaning, can be prepared by reacting compounds of the formula

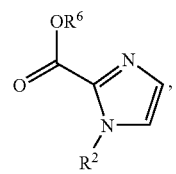
(IX)

in which
R⁶ is methyl or ethyl, and
R² has the abovementioned meaning, with fuming nitric acid, concentrated nitric acid, nitration acid or other mixing ratios of sulphuric acid and nitric acid, where appropriate in acetic anhydride as solvent, preferably in a temperature range from room temperature to 60° C. under atmospheric pressure.

The compounds of the formula (IX) are known or can be synthesized from the appropriate precursors by known processes.

The introduction of the substituent R² by the alkylation methods known to the skilled worker is possible at different places in the synthetic route, depending on the substitution pattern of the imidazole.

Synthesis scheme :

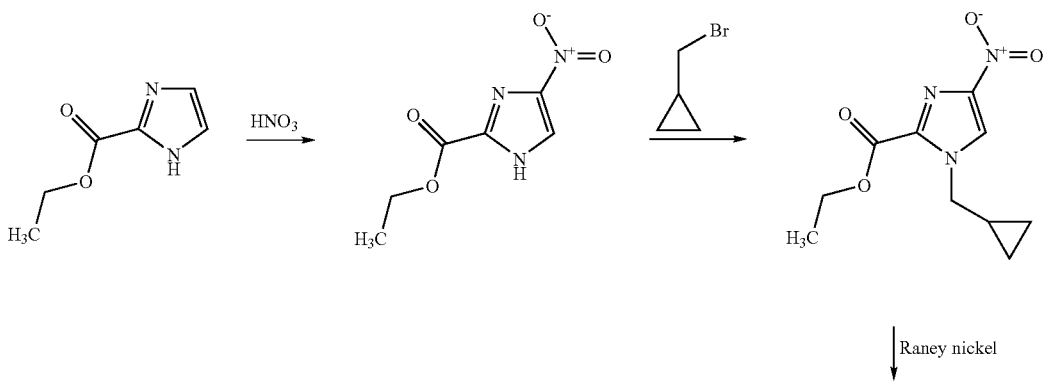

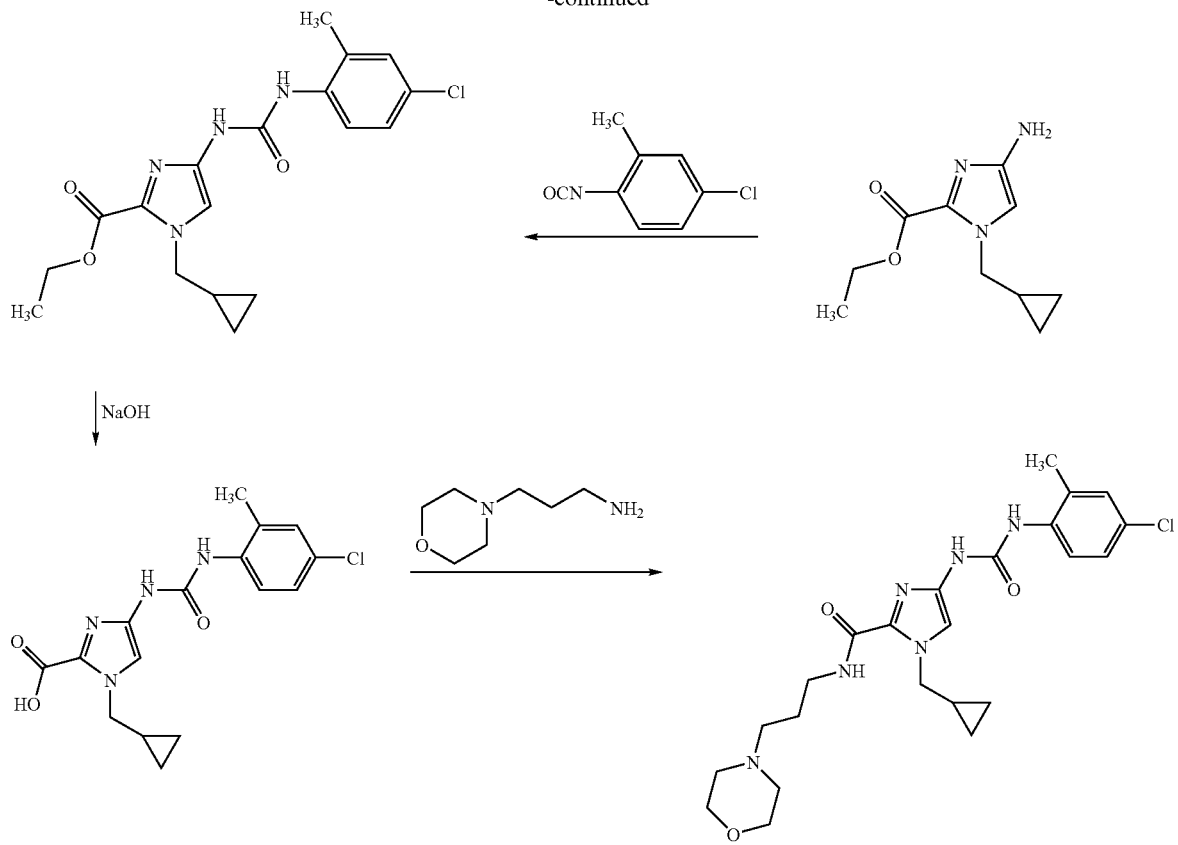

The compounds of the invention of the general formula (I) show a surprising range of effects which could not have been predicted. They show an antiviral effect on representatives of the group of Herpes viridae (herpes viruses), in particular on cytomegaloviruses (CMV) especially on human cytomegalovirus (HCMV). They are therefore suitable for the treatment and/or prophylaxis of diseases, especially of infections with viruses, in particular the aforementioned viruses, and the infectious diseases caused thereby. A viral infection means hereinafter both an infection with a virus and a disease caused by infection with a virus.

The compounds of the formula (I) can, because of their particular properties, be used to produce medicaments which are suitable for the prophylaxis and/or treatment of diseases, especially viral infections.

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone marrow and organ transplant patients who develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.
6) Treatment of HCMV-positive cancer patients with the aim of reducing HCMV-mediated tumour progression (cf. J. Cinatl, et al., *FEMS Microbiology Reviews* 2004, 28, 59-77).

The compounds of the invention are preferably used to produce medicaments which are suitable for the prophylaxis and/or treatment of infections with a representative of the group of Herpes viridae, particularly a cytomegalovirus, in particular human cytomegalovirus.

The compounds of the invention can, because of their pharmacological properties, be employed alone and, if required, also in combination with other active ingredients, especially antiviral active ingredients such as, for example, gancyclovir or acyclovir for the treatment and/or prevention of viral infections, in particular of HCMV infections.

The present invention further relates to the use of the compounds of the invention for the treatment and/or prophylaxis of disorders, preferably of viral infections, in particular of infections with human cytomegalovirus (HCMV) or another representative of the group of Herpes viridae.

The present invention further relates to the use of the compounds of the invention for the treatment and/or prophylaxis of disorders, in particular of the aforementioned disorders.

The present invention further relates to the use of the compounds of the invention for producing a medicament for the treatment and/or prophylaxis of disorders, especially of the aforementioned disorders.

The present invention further relates to a method for the treatment and/or prophylaxis of disorders, in particular of the aforementioned disorders, by using an antivirally effective amount of the compounds of the invention.

The compounds of the invention may have systemic and/or local effects. They can for this purpose be administered in a suitable way, such as, for example, by the oral, parenteral, pulmonary, nasal, sublingual, lingual, buccal, rectal, dermal, transdermal, conjunctival or otic route, or as implant or stent.

For these administration routes it is possible to administer the compounds of the invention in suitable administration forms.

Suitable for oral administration are administration forms which function according to the prior art and deliver the compounds of the invention rapidly and/or in modified manner and which comprise the compounds of the invention in crystalline and/or amorphicized and/or dissolved form, such as, for example, tablets (uncoated or coated tablets, for example with coatings which are resistant to gastric juice or dissolve with a delay or are insoluble and control the release of the compound of the invention), tablets which disintegrate rapidly in the oral cavity, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilisates or sterile powders.

Examples suitable for the other administration routes are pharmaceutical forms for inhalation (inter alia powder inhalers, nebulizers), nasal drops, solutions, sprays; tablets films/wafers or capsules, to be administered lingually, sublingually or buccally, suppositories, preparations for the eyes and ears, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, non-toxic, pharmaceutically suitable excipients. These include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants such as ascorbic acid), colours (for example inorganic pigments such as iron oxides) or flavour- and/or odour-masking agents.

The present invention further relates to medicaments which comprise at least one compound of the invention, usually together with one or more inert, non-toxic, pharmaceutically acceptable excipients, and to the use thereof for the aforementioned purposes.

It has generally proved advantageous to administer on intravenous administration amounts of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the amounts mentioned, specifically as a function of the body weight, administration route, individual response to the active ingredient, mode of preparation and time or interval over which administration takes place. Thus, it may be sufficient in some cases to make do with less than the aforementioned minimal amount, whereas in other cases the upper limit mentioned must be exceeded. It may in the event of administration of larger amounts be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

| Abbreviations used: | |
|---|---|
| aq. | aqueous |
| CD$_3$CN | deuteroacetonitrile |
| conc. | concentrated |
| DCI | direct chemical ionization (in MS) |
| DCM | dichloromethane |
| DIEA | N,N-diisopropylethylamine (Hünig's base) |
| dil. | dilute |
| DMAP | 4-N,N-dimethylaminopyridine |
| DMF | N,N-dimethylformamide |
| DMSO | dimethyl sulphoxide |
| EDCI × HCl | N'-(3-dimethylaminopropyl)-N-ethylcarbodiimide hydrochloride |
| EEA | ethyl acetate (acetic acid ethyl ester) |
| EI | electron impact ionization (in MS) |
| ESI | electrospray ionization (in MS) |
| Ex. | Example |
| h | hour |
| HATU | O-(7-azabenzotriazol-1-yl)-N,N,N',N'-tetramethyluronium hexafluorophosphate |
| HBTU | O-(benzotriazol-1-yl)-N,N,N',N'-tetramethyluronium hexafluorophosphate |
| HPLC | high pressure, high performance liquid chromatography |
| i.v. | in vacuo |
| LC-MS | coupled liquid chromatography-mass spectroscopy |
| LDA | lithium diisopropylamide |
| Lit. | literature (reference) |
| m.p. | melting point |
| MS | mass spectroscopy |
| NMR | nuclear magnetic resonance spectroscopy |
| RP-HPLC | reverse phase HPLC |
| RT | room temperature |
| R$_t$ | retention time (in HPLC) |
| sat. | saturated |
| sol. | solution |
| TBTU | O-(benzotriazol-1-yl)-N,N,N',N'-tetramethyluronium tetrafluoroborate |
| THF | tetrahydrofuran |
| TLC | thin-layer chromatography |

HPLC and LC-MS Methods:

Method 1 (LC-MS): Instrument: Micromass Platform LCZ with HPLC Agilent series 1100; column: Grom-SIL120 ODS-4 HE, 50 mm×2.0 mm, 3 µm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow rate: 0.8 m/min; UV detection: 210 nm.

Method 2 (LC-MS): Instrument: Micromass Quattro LCZ with HPLC Agilent series 1100; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 3 (LC-MS): Instrument: Micromass Platform LCZ with HPLC Agilent series 1100; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm n.

Method 4 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 5 (LC-MS): MS instrument type: Micromass ZQ; HPLC instrument type: HP 1100 Series; UV DAD; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 mL/min; oven: 50° C.; UV detection: 210 nm.

Method 6 (LC-MS): MS instrument type: Micromass ZQ; HPLC instrument type: HP 1100 series; UV DAD; column: Grom-Sil 120 ODS-4 HE 50 mm×2 mm, 3.0 μm; eluent A: water+500 μl 50% formic acid/1, eluent B: acetonitrile+500 μl 50% formic acid/1; gradient: 0.0 min 0% B→2.9 min 70% B→3.1 min 90% B→4.5 min 90% B; oven: 50° C.; flow rate: 0.8 ml/min; UV detection: 210 nm.

Method 7 (LC-MS): MS instrument type: Micromass ZQ; HPLC instrument type: Waters Alliance 2795; column: Merck Chromolith SpeedROD RP-18e 50 mm×4.6 mm; eluent A: water+500 μl50% formic acid/1; eluent B: acetonitrile+500 μl 50% formic acid/1; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 mL/min; UV detection: 210 nm.

Method 8 (LC-MS): Instrument: Micromass Quattro LCZ, with HPLC Agilent series 1100; column: Grom-SIL120 ODS-4 HE, 50 mm×2.0 mm, 3 μm; eluent A: 1 l water+1 ml 50% formic acid, eluent B: 1 l acetonitrile+1 ml 50% formic acid; gradient: 0.0 min 100% A→0.2 min 100% A→2.9 min 30% A→3.1 min 10% A→4.5 min 10% A; oven: 55° C.; flow rate: 0.8 mL/min; UV detection: 208-400 nm.

Method 9 (preparative HPLC): Column: Machery Nagel VP50/21 Nucleosil 100-5 C18 gravity, 5 μm, 21 mm×50 mm; eluent A: water+0.1% formic acid, eluent B: acetonitrile, gradient: 0 min 10% B, 2 min 10% B, 6 min 90% B, 7 min 90% B, 7.1 min 10% B, 8 min 10% B; flow rate: 25 mL/min, UV detection: 220 nm.

Method 10 (preparative HPLC): Column: Machery Nagel VP50/21 Nucleodur C18 gravity, 5 μm, 21 mm×50 mm; eluent A: water+0.1% ammonia, eluent B: acetonitrile, gradient: 0 min 10% B, 2 min 10% B, 6 min 90% B, 7 min 90% B, 7.1 min 10% B, 8 min 10% B; flow rate: 25 mL/min, UV detection: 220 nm.

Method 11 (analytical HPLC): Column: Kromasil 100 RP-18, 60 mm×2.1 mm, 3.5 μm; eluent A: water+0.5% perchloric acid (70% strength), eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; detection: UV 210 nm.

Starting Compounds

Example 1A

Ethyl 1-benzyl-1H-imidazole-2-carboxylate

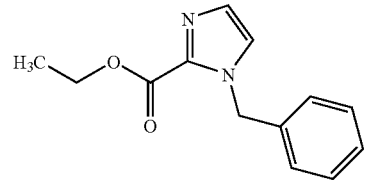

148 g (936 mmol) of 1-benzyl-1H-imidazole are suspended in 480 ml of acetonitrile and, at −20° C., 120 ml (87.1 g; 860 mmol) of triethylamine are added. Then, over the course of 15 minutes, 211.2 ml (239 g; 2208 mmol) of ethyl chloroformate are added dropwise. The reaction mixture is stirred at −20° C. for 10 minutes. After warming to 15 to 20° C., the reaction mixture is stirred for 18 h and then concentrated in vacuo. The residue is mixed with water, saturated sodium chloride solution and saturated sodium bicarbonate solution and extracted three times with ethyl acetate. The combined organic phases are washed with saturated sodium chloride solution and, after drying with magnesium sulphate, evaporated in vacuo. The residue is fractionally distilled under high vacuum (boiling point=173 to 181° C., pressure=1.7 to 1.2 mbar).

Yield: 122.6 g (46% of theory)

LC-MS (Method 4): $R_t$=1.71 min.

MS (ESI$^+$): m/z=231 [M+H]$^+$ $^1$H-NMR (300 MHz, DMSO-d$_6$): δ=7.6 (s, 1H), 7.4-7.1 (m, 6H), 5.2 (s, 2H), 4.25 (q, 2H), 1.25 (tr, 3H) ppm.

Example 2A

Ethyl imidazole-2-carboxylate

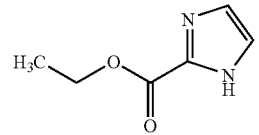

34.7 g (150.9 mmol) of ethyl 1-benzyl-1H-imidazole-2-carboxylate are dissolved in 1005 ml of ethanol, and 34 g of ammonium formate are added. The reaction mixture is heated to reflux for about 6 h. Then a total of 8 g of 10% palladium on activated carbon and 18 g of ammonium formate is added in small portions. After cooling, the catalyst is filtered off and the filtrate is concentrated in vacuo. The product which crystallizes out is stirred in 80 ml of ice-water and filtered off with suction.

Yield: 15.9 g (75% of theory)

MS (ESI$^+$): m/z=141 [M+H]$^+$ $^1$H-NMR (200 MHz, DMSO-d$_6$): δ=13.3 (s broad, 1H), 7.4 (s, 1H), 7.15 (s, 1H), 4.3 (q, 2H), 1.3 (tr, 3H) ppm.

Example 3A

Ethyl 4-nitro-1H-imidazole-2-carboxylate

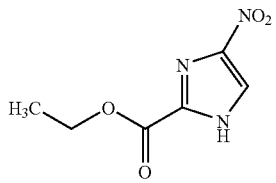

16.08 g (114.7 mmol) of ethyl imidazole-2-carboxylate are dissolved in 71.7 ml of concentrated sulphuric acid while cooling in ice. Then 71.7 ml of 100% strength fuming nitric acid are added dropwise. The reaction solution is stirred at 50 to 60° C. for 3 h and, after cooling, poured into 800 ml of ice/water mixture. The crystals which separate out are filtered off with suction and washed with 1500 ml of ice-water.

Yield: 15 g (70% of theory)
MS (ESI$^+$): m/z=186 [M+H]$^+$
$^1$H-NMR (300 MHz, DMSO-d$_6$): δ=14.5 (s broad, 1H), 8.5 (s, 1H), 4.4 (q, 2H), 1.35 (tr, 3H) ppm.

Example 4A 4-({[(4-Chloro-2-methylphenyl)amino]carbonyl}amino)-1-(cyclopropylmethyl)-1H-imidazole-2-carboxylic Acid

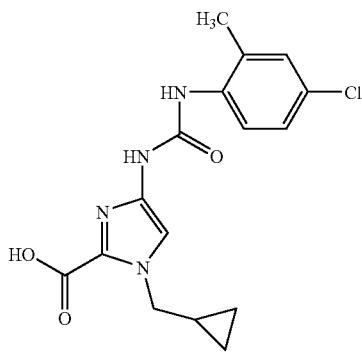

Stage 1

Ethyl 1-(cyclopropylmethyl)-4-nitro-1H-imidazole-2-carboxylate

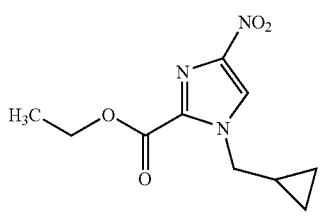

15 g (81 mmol) of ethyl 4-nitro-1H-imidazole-2-carboxylate are stirred together with 13.13 g (97.2 mmol) of cyclopropylmethyl bromide and 22.4 g (162 mmol) of potassium carbonate in 165 ml of DMF at 80° C. under argon for 1 h. After cooling, the reaction mixture is diluted with water and extracted four times with ethyl acetate. The combined organic phases are washed once with water and three times with saturated sodium chloride solution, dried with magnesium sulphate and evaporated in vacuo. The crystalline residue is further used directly for the next reaction.

Yield: 17.59 g (70% of theory)
LC-MS (Method 2): R$_t$=2.02 min.
MS (ESI$^+$): m/z=240 [M+H]$^+$
$^1$H-NMR (300 MHz, DMSO-d$_6$): δ=8.2 (s, 1H), 4.4 (q, 2H), 4.3 (d, 2H), 1.4 (m, 4H), 0.55 (q, 2H), 0.45 (q, 2H) ppm.

Stage 2

Ethyl 4-amino-1-(cyclopropylmethyl)-1H-imidazole-2-carboxylate

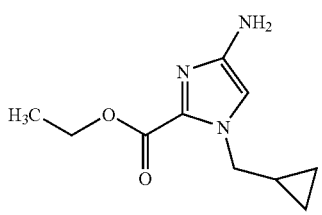

3.89 g (16.26 mmol) of ethyl 1-(cyclopropylmethyl)-4-nitro-1H-imidazole-2-carboxylate are dissolved in 50 ml of THF, and a spatula tip of Raney nickel is added. The reaction mixture is hydrogenated with hydrogen in the hydrogenation apparatus at room temperature. The catalyst is filtered off and the filtrate is evaporated in vacuo. The residue from evaporation is further used directly for the next reaction.

Yield: 3.46 g (100% of theory)
LC-MS (Method 3): R$_t$=1.21 min.
MS (ESI$^+$): m/z=210 [M+H]$^+$
$^1$H-NMR (300 MHz, DMSO-d$_6$): δ=6.55 (s, 1H), 4.55 (s, 2H), 4.2 (q, 2H), 4.1 (d, 2H), 1.25 (tr, 3H), 1.2 (m, 1H), 0.5 (q, 2H), 0.3 (q, 2H) ppm.

Stage 3

Ethyl 4-({[(4-chloro-2-methylphenyl)amino]carbonyl}amino)-1-(cyclopropylmethyl)-1H-imidazole-2-carboxylate

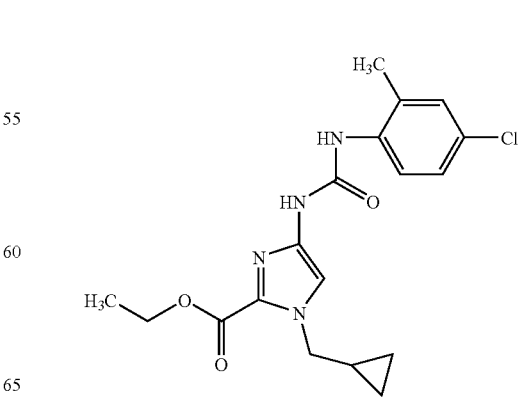

7.49 g (35.8 mmol) of ethyl 4-amino-1-(cyclopropylmethyl)-1H-imidazole-2-carboxylate in 18 ml of THF are mixed with 6 g (35.8 mmol) of 3-chloro-4-phenyl isocyanate and stirred at room temperature for 4 h. The reaction mixture is concentrated in vacuo, and the product which crystallizes out is stirred in 40 ml of ethyl acetate and filtered off with suction.

Yield: 11.1 g (82% of theory)

LC-MS (Method 2): $R_t$=2.66 min.

MS (ESI$^+$): m/z=376 [M+H]$^+$ $^1$H-NMR (300 MHz, DMSO-d$_6$): δ=9.45 (s, 1H), 8.0 (d, 1H), 7.35 (s, 1H), 7.3 (d, 1H), 7.2 (dd, 1H), 4.3 (q, 2H), 4.25 (d, 2H), 2.25 (s, 3H), 1.3 (tr, 3H), 1.25 (m, 1H), 0.55 (q, 2H), 0.35 (q, 2H) ppm.

Stage 4

4-({[(4-Chloro-2-methylphenyl)amino]carbonyl}amino)-1-(cyclopropylmethyl)-1H-imidazole-2-carboxylic Acid

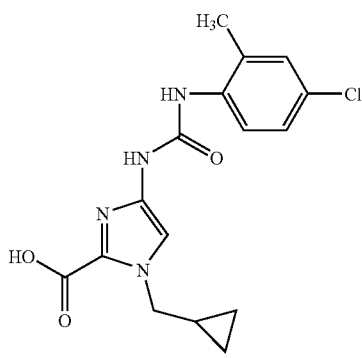

10.6 g (28.1 mmol) of ethyl 4-({[(4-chloro-2-methylphenyl)amino]carbonyl}amino)-1-(cyclopropylmethyl)-1H-imidazole-2-carboxylate are suspended in 158 ml of ethanol. While cooling in ice, 16.4 ml of water and 6 ml (112 mmol) of 50% strength aqueous sodium hydroxide solution are added. The reaction mixture is stirred at room temperature for 1 h and then concentrated in vacuo. The residue is taken up in 100 ml of isopropanol and, while cooling in ice, 100 ml of 1N hydrochloric acid are added. The crystals are filtered off with suction and dried in vacuo at 40° C.

Yield: 9.85 g (100% of theory)

LC-MS (Method 4): $R_t$=1.74 min.

MS (ESI$^+$): m/z=349 [M+H]$^+$ $^1$H-NMR (400 MHz, DMSO-d$_6$): δ=9.4 (s, 1H), 8.0 (d, 1H), 7.3 (s, 1H), 7.25 (d, 1H), 7.2 (dd, 1H), 4.25 (d, 2H), 2.25 (s, 3H), 1.25 (m, 1H), 0.55 (q, 2H), 0.35 (q, 2H) ppm.

Example 5A 1-(Cyclopropylmethyl)-4-[({[4-(trifluoromethoxy)phenyl]amino}carbonyl)amino]-1H-imidazole-2-carboxylic Acid

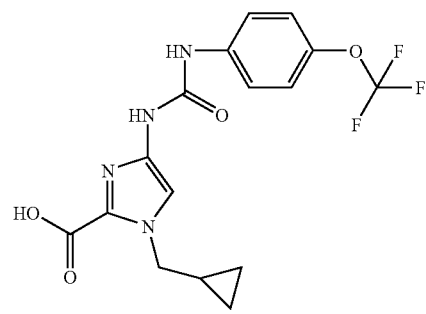

Preparation takes place in analogy to Example 4A.

Yield: 10.2 g (93% of theory)

LC-MS (Method 4): $R_t$=1.87 min.

MS (ESI$^+$): m/z=385 [M+H]$^+$ $^1$H-NMR (400 MHz, DMSO-d$_6$): δ=8.6 (s, 1H), 8.4 (s, 1H), 7.55 (d, 2H), 7.4 (s, 1H), 7.25 (d, 2H), 4.25 (d, 2H), 1.25 (m, 1H), 0.55 (q, 2H), 0.35 (q, 2H) ppm.

Example 6A

1-Butyl-4-({[(4-chloro-2-methylphenyl)amino]carbonyl}amino)-1H-imidazole-2-carboxylic Acid

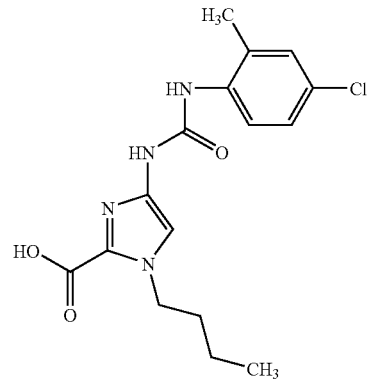

Preparation takes place in analogy to Example 4A. Yield: 2.2 g (93% of theory)

LC-MS (Method 4): $R_t$=1.83 min.

MS (ESI$^+$): m/z=351 [M+H]$^+$ $^1$H-NMR (300 MHz, DMSO-d$_6$): δ=9.35 (s, 1H), 8.0 (d, 1H), 7.3 (s, 1H), 7.25 (d, 1H), 7.2 (dd, 1H), 4.35 (tr, 2H), 2.25 (s, 3H), 1.7 (quintet, 2H), 1.25 (sextet, 2H), 0.9 (tr, 3H) ppm.

Example 7A

1-Butyl-4-[({[4-(trifluoromethoxy)phenyl]amino}carbonyl)amino]-1H-imidazole-2-carboxylic Acid

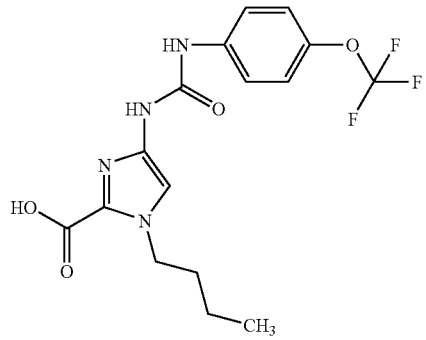

Preparation takes place in analogy to Example 4A. Yield: 2.05 g (96% of theory)

LC-MS (Method 4): $R_t$=1.96 min.

MS (ESI$^+$): m/z=387 [M+H]$^+$ $^1$H-NMR (300 MHz, DMSO-d$_6$): δ=9.0 (s, 1H), 8.9 (s, 1H), 7.55 (d, 2H), 7.3 (s, 1H), 7.25 (d, 1H), 4.35 (tr, 2H), 1.7 (quintet, 2H), 1.25 (sextet, 2H), 0.9 (tr, 3H) ppm.

Example 8A 4-({[(4-Chloro-2-methylphenyl)amino]carbonyl}amino)-1-(2-methoxyethyl)-1H-imidazole-2-carboxylic Acid

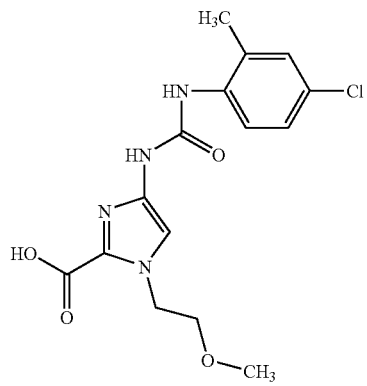

Preparation takes place in analogy to Example 4A.

Yield: 1.36 g (91% of theory)

LC-MS (Method 4): $R_t$=1.56 min.

MS (ESI$^+$): m/z=353 [M+H]$^+$ $^1$H-NMR (300 MHz, DMSO-d$_6$): δ=9.35 (s, 1H), 8.0 (d, 1H), 7.25 (d, 1H), 7.2 (m, 2H), 4.55 (tr, 2H), 3.65 (tr, 2H), 2.25 (s, 3H) ppm.

Example 9A 1-(2-Methoxyethyl)-4-[({[4-(trifluoromethoxy)phenyl]amino}carbonyl)amino]-1H-imidazole-2-carboxylic Acid

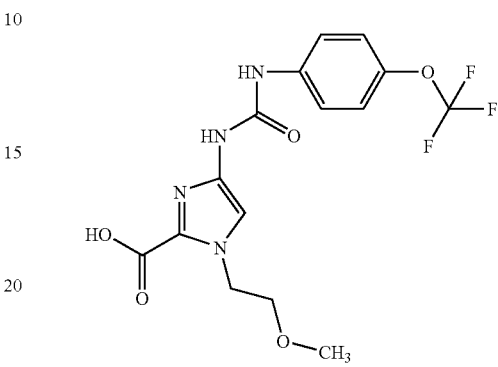

Preparation takes place in analogy to Example 4A.

Yield: 1 g (49% of theory)

LC-MS (Method 4): $R_t$=1.70 min.

MS (ESI$^+$): m/z=389 [M+H]$^+$ $^1$H-NMR (300 MHz, DMSO-d$_6$): δ=9.15 (s, 1H), 8.45 (s, 1H), 7.55 (d, 2H), 7.3 (s, 1H), 7.25 (d, 2H), 4.55 (tr, 2H), 3.65 (tr, 2H) ppm.

Example 10A

1-Benzyl-4-({[(4-chloro-2-methylphenyl)amino]carbonyl}amino)-1H-imidazole-2-carboxylic Acid

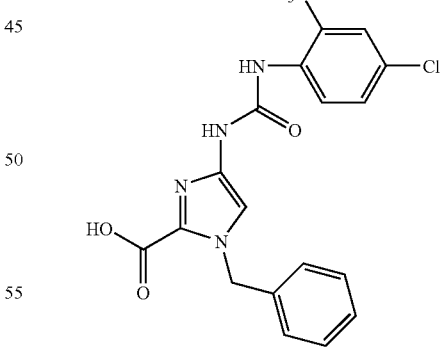

Preparation takes place in analogy to Example 4A.

Yield: 2.34 g (93% of theory)

LC-MS (Method 2): $R_t$=2.12 min.

MS (ESI$^+$): m/z=385 [M+H]$^+$ $^1$H-NMR (300 MHz, DMSO-d$_6$): δ=9.45 (s, 1H), 7.9 (d, 1H), 7.4-7.1 (m, 8H), 5.65 (s, 2H), 2.25 (s, 3H) ppm.

Example 11A

1-Benzyl-4-[({[4-(trifluoromethoxy)phenyl]amino}carbonyl)amino]-1H-imidazole-2-carboxylic Acid

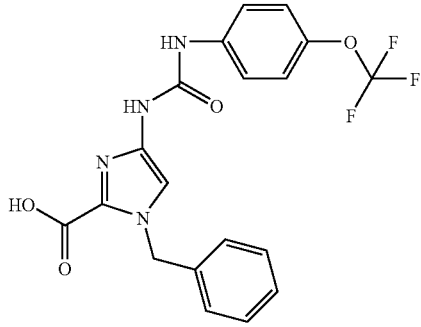

Preparation takes place in analogy to Example 4A.
Yield: 2.37 g (96% of theory)
LC-MS (Method 5): $R_t$=2.29 min.
MS (ESI$^+$): m/z=421 [M+H]$^+$
$^1$H-NMR (300 MHz, DMSO-d$_6$): δ=9.05 (s, 1H), 8.9 (s, 1H), 7.55 (d, 2H), 7.4-7.2 (m, 8H), 5.6 (s, 2H) ppm.

Example 12A 4-({[(4-Chloro-2-methylphenyl)amino]carbonyl}amino)-1-(3-methylbut-2-en-1-yl)-1H-imidazole-2-carboxylic Acid

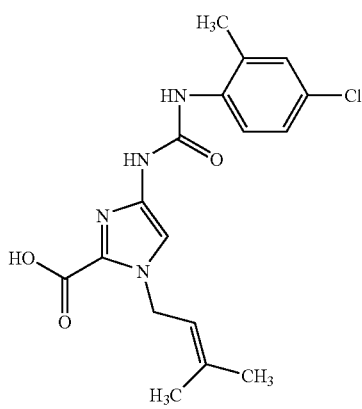

Preparation takes place in analogy to Example 4A.
Yield: 2.53 g (95% of theory)
LC-MS (Method 4): $R_t$=1.91 min.
MS (ESI$^+$): m/z=363 [M+H]$^+$
$^1$H-NMR (300 MHz, DMSO-d$_6$): δ=9.35 (s, 1H), 8.0 (d, 1H), 7.25 (s, 1H), 7.2 (m, 2H), 5.35 (tr, 1H), 5.0 (d, 2H), 2.25 (s, 3H), 1.8 (s, 3H), 1.75 (s, 3H) ppm.

Example 13A 1-(3-Methylbut-2-en-1-yl)-4-[({[4-(trifluoromethoxy)phenyl]amino}carbonyl)amino]-1H-imidazole-2-carboxylic Acid

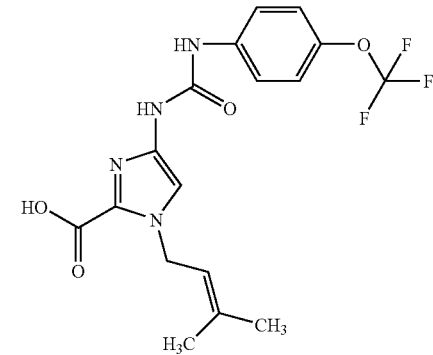

Preparation takes place in analogy to Example 4A.
Yield: 2.67 g (91% of theory)
LC-MS (Method 4): $R_t$=2.03 min.
MS (ESI$^+$): m/z=399 [M+H]$^+$
$^1$H-NMR (300 MHz, DMSO-d$_6$): δ=9.05 (s, 1H), 8.9 (s, 1H), 7.55 (d, 2H), 7.3 (m, 3H), 5.35 (tr, 1H), 5.0 (d, 2H), 1.75 (s, 3H), 1.7 (s, 3H) ppm.

Example 14A 4-({[(4-Chloro-2-methylphenyl)amino]carbonyl}amino)-1-(2-phenoxyethyl)-1H-imidazole-2-carboxylic Acid

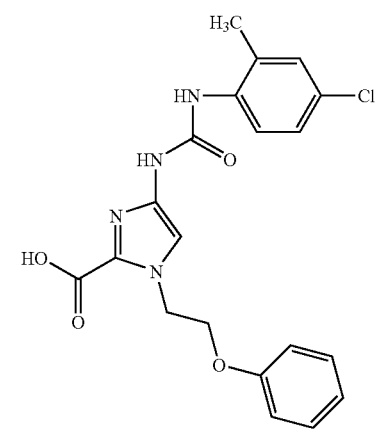

Preparation takes place in analogy to Example 4A.
Yield: 2.97 g (99% of theory)
LC-MS (Method 3): $R_t$=2.21 min.
MS (ESI$^+$): m/z=415 [M+H]$^+$
$^1$H-NMR (300 MHz, DMSO-d$_6$): δ=9.6 (s, 1H), 8.0 (d, 1H), 7.3-7.1 (m, 5H), 6.9 (m, 3H), 4.8 (tr, 2H), 4.35 (d, 2H), 2.25 (s, 3H) ppm.

Example 15A 1-(2-Phenoxyethyl)-4-[({[4-(trifluoromethoxy)phenyl]amino}carbonyl)amino]-1H-imidazole-2-carboxylic Acid

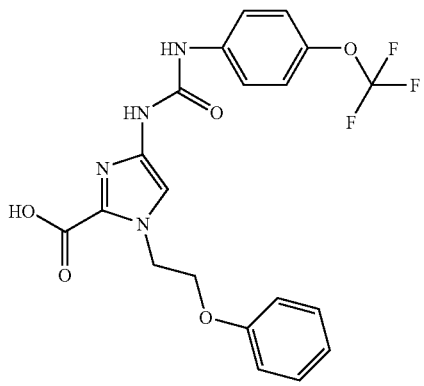

Preparation takes place in analogy to Example 4A.
Yield: 2.9 g (98% of theory)
LC-MS (Method 3): $R_t$=2.31 min.
MS (ESI$^+$): m/z=451 [M+H]$^+$
$^1$H-NMR (300 MHz, DMSO-d$_6$): δ=8.9 (s, 1H), 7.55 (d, 2H), 7.4 (s, 1H), 7.25 (m, 4H), 6.9 (m, 3H), 4.8 (tr, 2H), 4.35 (d, 2H) ppm.

Example 16A 4-({[(4-Chloro-2-methylphenyl)amino]carbonyl}amino)-1-(3,3-dichloroprop-2-en-1-yl)-1H-imidazole-2-carboxylic Acid

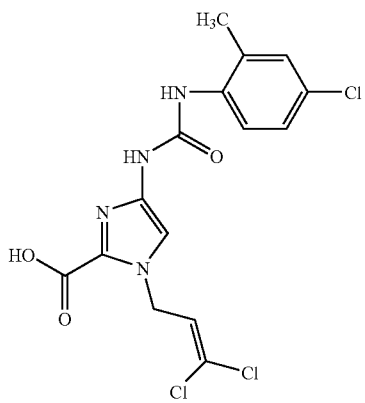

Preparation takes place in analogy to Example 4A.
Yield: 1.46 g (94% of theory)
LC-MS (Method 3): $R_t$=2.21 min.
MS (ESI$^+$): m/z=403 [M+H]$^+$
$^1$H-NMR (300 MHz, DMSO-d$_6$): δ=9.4 (s, 1H), 7.95 (d, 1H), 7.25 (m, 2H), 7.2 (dd, 2H), 6.4 (tr, 1H), 5.1 (d, 2H), 2.25 (s, 3H) ppm.

Example 17A 1-(3,3-Dichloroprop-2-en-1-yl)-4-[({[4-(trifluoromethoxy)phenyl]amino}carbonyl)amino]-1H-imidazole-2-carboxylic Acid

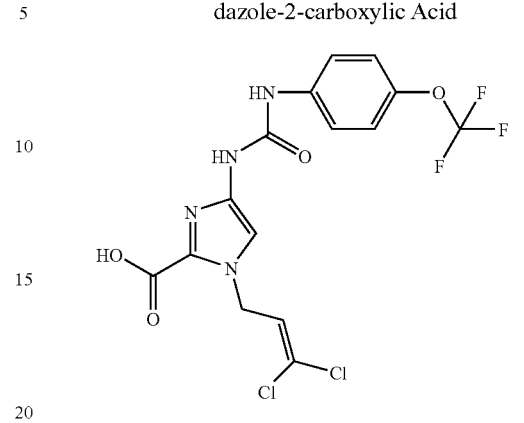

Preparation takes place in analogy to Example 4A.
Yield: 1.93 g (82% of theory)
LC-MS (Method 5): $R_t$=2.35 min.
MS (ESI$^+$): m/z=439 [M+H]$^+$
$^1$H-NMR (400 MHz, DMSO-d$_6$): δ=9.0 (m, 2H), 7.55 (d, 2H), 7.35 (s, 1H), 7.2 (d, 2H), 6.4 (tr, 1H), 5.15 (d, 2H) ppm.

Example 18A 4-({[(4-Methyl-3-fluorophenyl)amino]carbonyl}amino)-1-methyl-1H-imidazole-2-carboxylic Acid

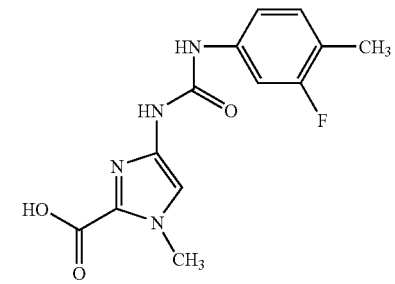

Stage 1

Ethyl 4-({[(3-fluoro-4-methylphenyl)amino]carbonyl}amino)-1-methyl-1H-imidazole-2-carboxylate

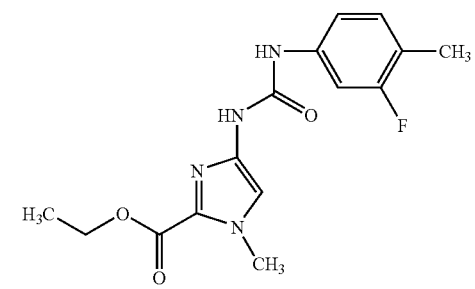

1.30 g (3.84 mmol) of ethyl 4-amino-1-methyl-1H-imidazole-2-carboxylate (synthesis analogous to Example 4A, stage 3, or else according to Tetrahedron Lett. 2003, 44, 1607 and literature cited therein) are mixed in 50 ml of THF with 1.16 g (7.68 mmol) of 3-fluoro-4-methylphenyl isocyanate under argon and stirred at room temperature overnight. The reaction mixture is filtered, and the filtrate is concentrated in vacuo and purified by preparative HPLC. The residue from filtration affords together with the product obtained after the HPLC purification 715 mg of product.

Yield: 715 mg (58% of theory)
LC-MS (Method 6): $R_t$=2.9 min.
MS (ESI$^+$): m/z=321 [M+H]$^+$ Stage 2

4-({[(4-Methyl-3-fluorophenyl)amino]carbonyl}amino)-1-methyl-1H-imidazole-2-carboxylic Acid

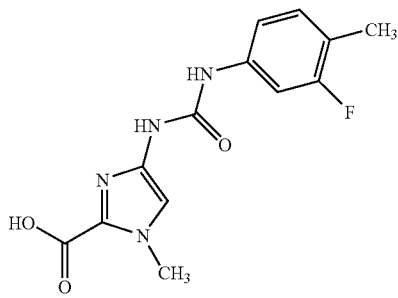

690 mg (2.15 mmol) of ethyl 4-({[(3-fluoro-4-methylphenyl)amino]carbonyl}amino)-1-methyl-1H-imidazole-2-carboxylate are suspended in 5 ml of ethanol and 12 ml of tetrahydrofuran. While cooling in ice, 2 ml (25 mmol) of 50% strength aqueous sodium hydroxide solution are added. The reaction mixture is stirred at room temperature overnight and then, while cooling in ice, acidified with 1N hydrochloric acid. The solution is extracted with dichloromethane. The organic phase is concentrated in vacuo.

Yield: quantitative
LC-MS (Method 7): $R_t$=1.65 min.
MS (ESI$^+$): m/z=293 [M+H]$^+$ Example 19A 4-[({[4-(Trifluoromethoxy)phenyl]amino}carbonyl)amino]-1-[4-(trifluoromethyl)benzyl]-1H-imidazole-2-carboxylic Acid

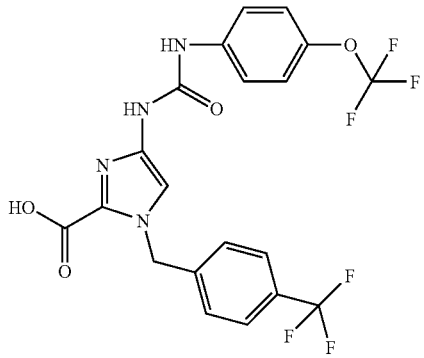

Preparation in analogy to Example 4A.
Yield: 15.2 g (100% of theory)
LC-MS (Method 2): $R_t$=2.46 min.
MS (ESI$^+$): m/z=489 [M+H]$^+$
$^1$H-NMR (300 MHz, DMSO-d$_6$): δ=9.15 (s, 1H), 9.05 (s, 1H), 7.75 (d, 2H), 7.55 (d, 2H), 7.45 (s, 1H), 7.35 (d, 2H), 7.25 (d, 2H), 5.7 (s, 2H) ppm.

Example 20A 4-({[(4-Chloro-2-methylphenyl)amino]carbonyl}amino)-1-[4-(trifluoromethyl)benzyl]-1H-imidazole-2-carboxylic Acid

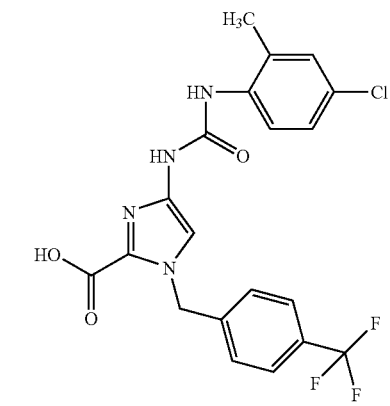

Preparation in analogy to Example 4A.
Yield: 15.6 g (100% of theory)
LC-MS (Method 4): $R_t$=2.23 min.
MS (ESI$^+$): m/z=453 [M+H]$^+$
$^1$H-NMR (300 MHz, DMSO-d$_6$): δ=9.5 (s, 1H), 7.95 (d, 1H), 7.75 (d, 2H), 7.4 (d, 2H), 7.35 (s, 1H), 7.25 (s, 1H), 7.15 (d, 1H), 5.75 (s, 2H), 2.25 (s, 3H) ppm.

Example 21A

N-(2-Chloroethyl)-4-({[(4-chloro-2-methylphenyl)amino]carbonyl}amino)-1-[4-(trifluoromethyl)benzyl]-1H-imidazole-2-carboxamide

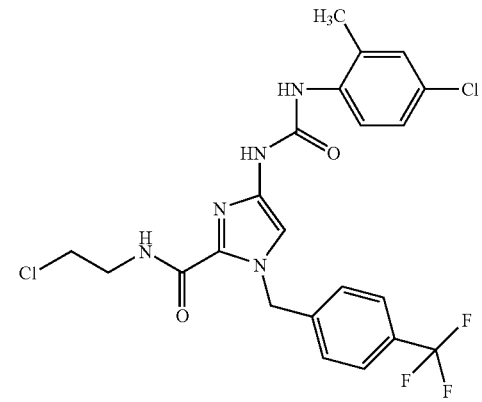

90.6 mg (0.2 mmol) of 4-({[(4-chloro-2-methylphenyl)amino]carbonyl}amino)-1-[4-(trifluoromethyl)benzyl]-1H-imidazole-2-carboxylic acid (Example 20A) are dissolved in 500 μl of DMF, and 36.65 mg (0.3 mmol) of DMAP and 114 mg (0.3 mmol) of HATU are added. After stirring at RT for 5 minutes, a solution of 46.4 mg (0.4 mmol) of 1-chloro-2-aminoethane and 25.8 mg (0.2 mmol) of N,N-diisopropylethylamine in 500 μl of DMF is added dropwise. The reaction mixture is stirred at RT for 6 h, then filtered and purified by preparative HPLC (method 9). The product-containing fractions are evaporated in vacuo.

Yield: 61.1 mg (59% of theory)
LC-MS (Method 4): R$_t$=2.67 min.
MS (ESI): m/z=514 [M+H]$^+$
$^1$H-NMR (300 MHz, DMSO-d$_6$): δ=9.25 (s, 1H), 8.35 (s broad, 2H), 7.9 (d, 1H), 7.7 (d, 2H), 7.45 (d, 2H), 7.3 (s, 1H), 7.25 (s, 1H), 7.15 (d, 1H), 5.75 (s, 2H), 3.7 (tr, 2H), 3.55 (q, 2H), 2.25 (s, 3H) ppm.

Example 22A

N-(2-Chloroethyl)-4-[({[4-(trifluoromethoxy)phenyl]amino}carbonyl)amino]-1-[4-(trifluoromethyl)benzyl]-1H-imidazole-2-carboxamide

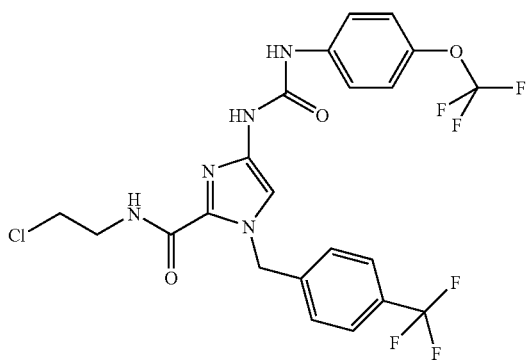

Preparation takes place in analogy to Example 21A from 4-[({[4-(trifluoromethoxy)phenyl]amino}carbonyl)amino]-1-[4-(trifluoromethyl)benzyl]-1H-imidazole-2-carboxylic acid (Example 19A).

Yield: 635 mg (58% of theory)
LC-MS (Method 4): R$_t$=2.73 min.
MS (ESI$^+$): m/z=550 [M+H]$^+$
$^1$H-NMR (300 MHz, DMSO-d$_6$): δ=9.5 (s, 1H), 8.8 (s, 1H), 8.4 (tr, 1H), 7.75 (d, 2H), 7.55 (d, 2H), 7.45 (s, 2H), 7.35 (d, 1H), 7.25 (d, 2H), 5.75 (s, 2H), 3.7 (tr, 2H), 3.55 (q, 2H) ppm.

Example 23A

N-(2-Chloroethyl)-1-(cyclopropylmethyl)-4-[({[4-(trifluoromethoxy)phenyl]amino}-carbonyl)amino]-1H-imidazole-2-carboxamide

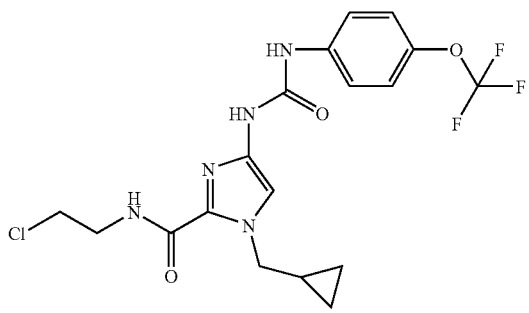

Preparation takes place in analogy to Example 21A from 1-(cyclopropylmethyl)-4-[({[4-(trifluoromethoxy)phenyl]amino}carbonyl)amino]-1H-imidazole-2-carboxylic acid (Example 5A).

Yield: 668 mg (75% of theory)
LC-MS (Method 4): R$_t$=2.45 min.
MS (ESI$^+$): m/z=446 [M+H]$^+$
$^1$H-NMR (300 MHz, DMSO-d$_6$): δ=9.05 (s, 1H), 8.7 (s, 1H), 8.3 (tr, 1H), 7.55 (d, 2H), 7.3 (d, 1H), 7.25 (d, 2H), 4.3 (d, 2H), 3.7 (tr, 2H), 3.55 (q, 2H), 1.35 (m, 1H), 0.5 (m, 2H), 0.35 (m, 2H) ppm.

Example 24A

2-[(2-Bromoacetyl)oxy]ethyl-4-({[(4-chloro-2-methylphenyl)amino]carbonyl}amino)-1-[4-(trifluoromethyl)benzyl]-1H-imidazole-2-carboxylate

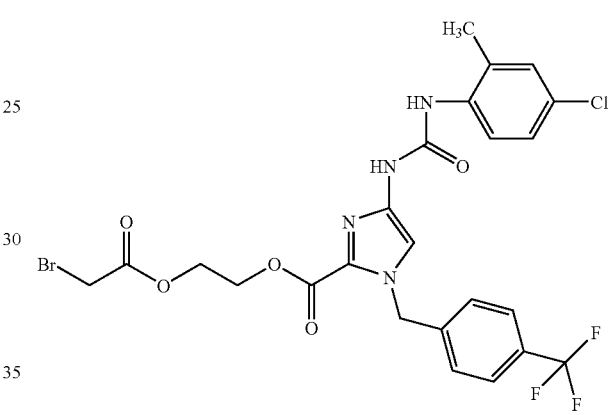

1 g (2 mmol) of 2-hydroxyethyl-4-({[(4-chloro-2-methylphenyl)amino]carbonyl}amino)-1-[4-(trifluoromethyl)benzyl]-1H-imidazole-2-carboxylate (Example 125) are dissolved in a mixture of 25 ml of dichloromethane and 12 ml of DMF, and 1570 μl (1.14 g, 11.2 mmol) of triethylamine are added. While cooling in ice, 804 μl (1.52 g, 9.6 mmol) of bromoacetyl chloride and a catalytic amount of DMAP are added. After stirring at RT for 16 h, a further 0.57 g (5.6 mmol) of triethylamine, 0.76 g (4.8 mmol) of bromoacetyl chloride and a few crystals of DMAP are added while cooling in ice. The reaction mixture is stirred at RT for 2.5 h, poured into saturated sodium bicarbonate solution and extracted twice with ethyl acetate. The combined extracts are washed twice with water and once with saturated sodium chloride solution, dried with magnesium sulphate and evaporated in vacuo. The residue from evaporation is purified by chromatography on silica gel with dichloromethane/methanol as eluent.

Yield: 733 mg (59% of theory)
LC-MS (Method 4): R$_t$=2.69 min.
MS (ESI$^+$): m/z=617 [M+H]$^+$
$^1$H-NMR (300 MHz, DMSO-d$_6$): δ=9.55 (s, 1H), 8.5 (s broad, 1H), 7.95 (d, 1H), 7.7 (d, 2H), 7.45 (s, 1H), 7.4 (d, 2H), 7.25 (d, 1H), 7.15 (dd, 1H), 5.7 (s, 2H), 4.4 (m, 4H), 4.35 (s, 2H), 2.25 (s, 3H) ppm.

Example 25A

2-[({4-[({[2-Methyl-4-(trifluoromethoxy)phenyl]amino}carbonyl)amino]-1-[4-(trifluoromethyl)benzyl]-1H-imidazol-2-yl}carbonyl)amino]ethyl Chloroacetate

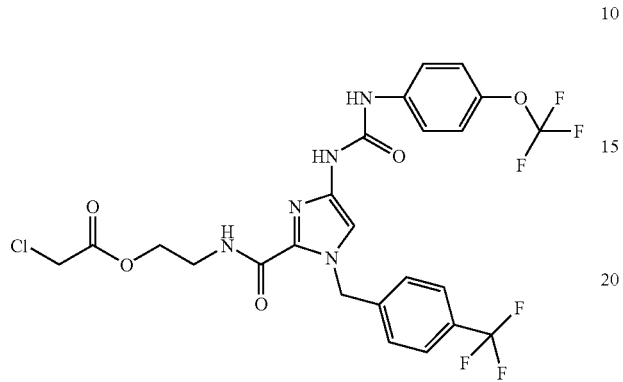

850 mg (1.6 mmol) of N-(2-hydroxyethyl)-4-[({[4-(trifluoromethoxy)phenyl]amino}-carbonyl)amino]-1-[4-(trifluoromethyl)benzyl]-1H-imidazole-2-carboxamide (Example 124) are dissolved in 3.2 ml of absolute DMF under argon, and a few crystals of DMAP and 647 mg (892 µl, 6.4 mmol) of triethylamine are added. While cooling in ice, 755 mg (400 µl, 4.8 mmol) of bromoacetyl chloride are added dropwise. The reaction mixture is stirred at RT for 1.5 h and then poured into cold saturated sodium bicarbonate solution and extracted twice with ethyl acetate. The combined extracts are washed once with water and three times with saturated sodium chloride solution, dried with magnesium sulphate and evaporated in vacuo.

Yield: 1 g (100% of theory)
LC-MS (Method 5): $R_t$=2.86 min.
MS (ESI$^+$): m/z=608 [M+H]$^+$
$^1$H-NMR (300 MHz, DMSO-d$_6$): δ=9.15 (s, 1H), 8.75 (s, 1H), 8.35 (tr, 1H), 7.7 (d, 2H), 7.55 (d, 2H), 7.45 (s, 2H), 7.35 (d, 1H), 7.25 (d, 2H), 5.75 (s, 2H), 4.3 (s, 2H), 4.35 (tr, 2H), 3.5 (q, 2H) ppm.

Example 26A

2-[({4-({[(4-Chloro-2-methylphenyl)amino]carbonyl}amino)-1-[4-(trifluoromethyl)-benzyl]-1H-imidazol-2-yl}carbonyl)amino]ethyl Chloroacetate

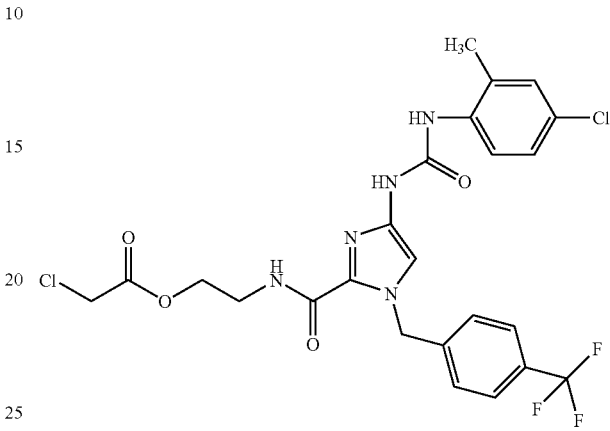

Preparation takes place in analogy to Example 25A from 4-({[(4-chloro-2-methylphenyl)amino]carbonyl}amino)-N-(2-hydroxyethyl)-1-[4-(trifluoromethyl)benzyl]-1H-imidazole-2-carboxamide (Example 123). Yield: 937 mg (100% of theory)
LC-MS (Method 4): $R_t$=2.80 min.
MS (ESI$^+$): m/z=572 [M+H]$^+$
$^1$H-NMR (300 MHz, DMSO-d$_6$): δ=9.25 (s, 1H), 8.35 (s broad, 2H), 7.9 (d, 1H), 7.7 (d, 2H), 7.4 (d, 2H), 7.3 (s, 1H), 7.25 (d, 1H), 7.15 (dd, 1H), 5.75 (s, 2H), 4.3 (s, 2H), 4.25 (tr, 2H), 3.5 (q, 2H), 2.25 (s, 3H) ppm.

Example 27A

2-[(2-Bromoacetyl)oxy]ethyl 4-[({[4-(trifluoromethoxy)phenyl]amino}carbonyl)amino]-1-[4-(trifluoromethyl)benzyl]-1H-imidazole-2-carboxylate

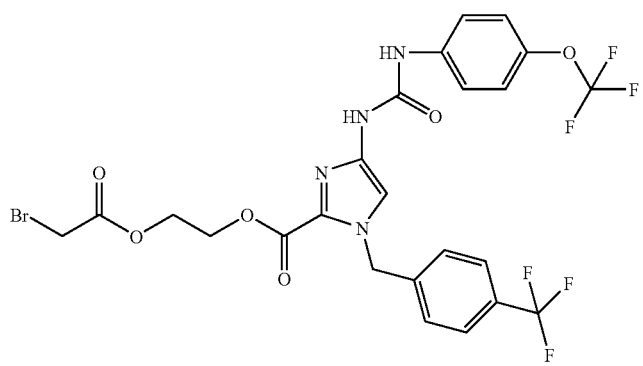

Preparation takes place in analogy to Example 24A from 2-hydroxyethyl-4-[({[4-(trifluoromethoxy)phenyl]amino}carbonyl)amino]-1-[4-(trifluoromethyl)benzyl]-1H-imidazole-2-carboxylate (Example 126). Yield: 834 mg (85% of theory)

LC-MS (Method 4): $R_t$=2.69 min.
MS (ESI$^+$): m/z=653 [M+H]$^+$
$^1$H-NMR (300 MHz, DMSO-d$_6$): δ=9.15 (s, 1H), 8.95 (s, 1H), 7.7 (d, 2H), 7.55 (s, 1H), 7.55 (d, 2H), 7.4 (d, 2H), 7.25 (d, 2H), 5.7 (s, 2H), 4.4 (m, 4H), 4.35 (s, 2H) ppm.

Example 28A

Ethyl 1-methyl-4-[({[4-(trifluoromethoxy)phenyl]amino}carbonyl)amino]-1H-imidazole-2-carboxylate

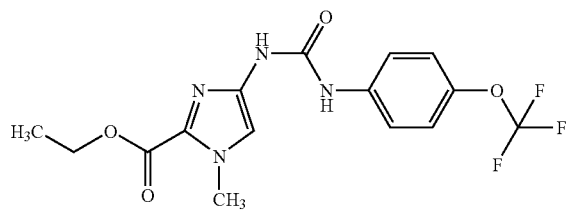

1.22 g (3.61 mmol) of ethyl 4-amino-1-methyl-1H-imidazole-2-carboxylate (synthesis analogous to Example 4A, stage 3, or else according to Tetrahedron Lett. 2003, 44, 1607 and literature cited therein) in 50 ml of THF are mixed with 1.46 g (7.21 mmol) of 4-(trifluoromethoxy)phenyl isocyanate under argon and stirred at room temperature overnight. The reaction mixture is filtered, and the filtrate is concentrated in vacuo and purified by chromatography.

Yield: 860 mg (62% of theory)
LC-MS (Method 5): $R_t$=2.41 min.
MS (ESI$^+$): m/z=373 [M+H]$^+$ Example 29A 1-Methyl-4-[({[4-(trifluoromethoxy)phenyl]amino}carbonyl)amino]-1H-imidazole-2-carboxylic Acid

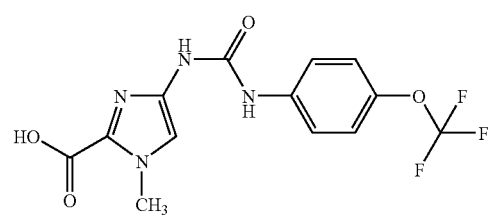

835 mg (2.13 mmol) of ethyl 1-methyl-4-[({[4-(trifluoromethoxy)phenyl]amino}carbonyl)amino]-1H-imidazole-2-carboxylate (Example 28A) are suspended in 5 ml of ethanol and 12 ml of tetrahydrofuran. While cooling in ice, 2 ml (25 mmol) of 50% strength aqueous sodium hydroxide solution are added. The reaction mixture is stirred at room temperature overnight and then, while cooling in ice, acidified with 1N hydrochloric acid. The solution is extracted with dichloromethane. The organic phase is concentrated in vacuo. The residue is purified by preparative HPLC.

Yield: 346 mg (44% of theory).
LC-MS (Method 4): $R_t$=1.62 min.
MS (ESI$^+$): m/z=345 [M+H]$^+$ Example 30A 1-Butyl-4-[({[4-(trifluoromethyl)phenyl]amino}carbonyl)amino]-1H-imidazole-2-carboxylic Acid

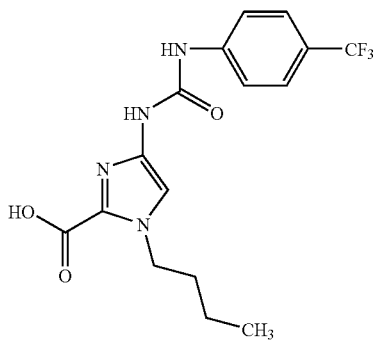

Preparation takes place in analogy to Example 4A.
Yield: 1.71 g (98% of theory)
LC-MS (Method 2): $R_t$=2.13 min.
MS (ESI$^+$): m/z=371 [M+H]$^+$
1H-NMR (300 MHz, DMSO-d$_6$): δ=9.30 (bs, 1H), 9.03 (bs, 1H), 7.64 (m, 4H), 7.36 (s, 1H), 4.35 (t, 2H), 1.68 (quint, 2H), 1.26 (sext, 2H), 0.89 (t, 3H).

Example 31A

1-Ethyl-4-[({[4-(trifluoromethoxy)phenyl]amino}carbonyl)amino]-1H-imidazole-2-carboxylic Acid

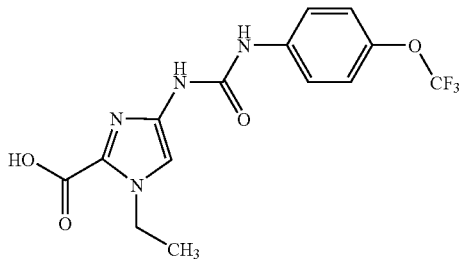

Preparation took place in analogy to Example 4A.
LC-MS (Method 5): $R_t$=1.94 min.
MS (ESI$^+$): m/z=359 [M+H]$^+$
$^1$H-NMR (300 MHz, DMSO-d$_6$): δ=10.3 (bs, 1H), 7.67 (m, 2H), 7.24 (s, 1H), 7.20 (m, 2H), 4.45 (q, 2H), 1.33 (t, 3H).

Example 32A 1-(Ethyl)-4-[({[4-(trifluoromethoxy)phenyl]amino}carbonyl)amino]-1H-imidazole-2-carboxylic Acid

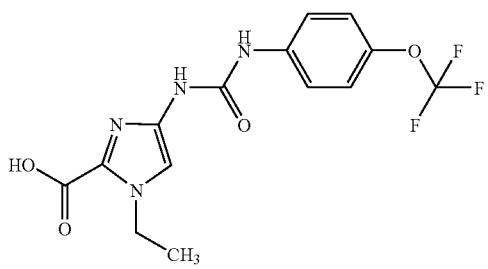

Preparation takes places in analogy to Example 4A.
Yield: 2 g (91% of theory)
LC-MS (Method 11): $R_t$=4.00 min.
MS (ESI$^+$): m/z=359 [M+H]$^+$
$^1$H-NMR (300 MHz, DMSO-$d_6$): δ=10.5 (s, broad, 1H), 7.65 (d, 2H), 7.2 (s, 1H), 7.15 (d, 2H), 4.45 (q, 2H), 1.35 (t, 3H) ppm.

Example 33A 1-(Butyl)-4-[({[4-(difluoromethoxy)phenyl]amino}carbonyl)amino]-1H-imidazole-2-carboxylic Acid

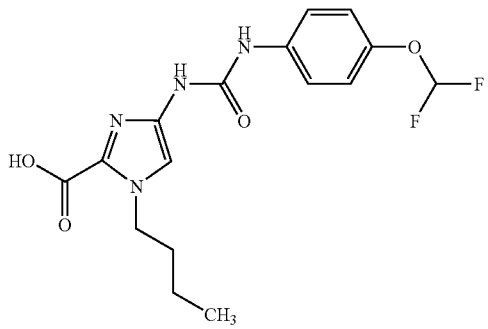

Preparation takes place in analogy to Example 4A.
Yield: 1.06 g (71% of theory).
LC-MS (Method 11): $R_t$=4.05 min.
MS (ESI$^+$): m/z=369 [M+H]$^+$
$^1$H-NMR (300 MHz, DMSO-$d_6$): δ=11.1 (s broad, 1H), 7.7 (d, 2H), 7.1 (t, 1H $J_{HF}$=75 Hz), 7.05 (m, 3H), 4.5 (t, 2H), 1.7 (m, 2H), 1.3 (m, 2H), 0.9 (t, 3H) ppm.

EXEMPLARY EMBODIMENTS

Example 1

4-({[(3-Fluoro-4-methylphenyl)amino]carbonyl}amino)-1-methyl-N-(pyridin-3-ylmethyl)-1H-imidazole-2-carboxamide

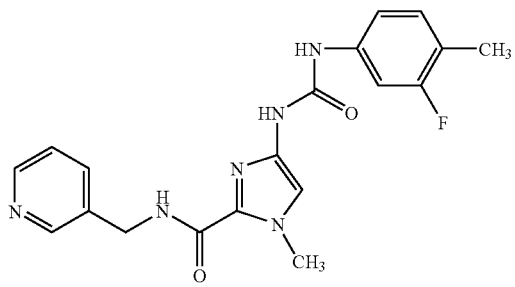

60 mg (0.2 mmol) of 4-({[(4-methyl-3-fluorophenyl)amino]carbonyl}amino)-1-methyl-1H-imidazole-2-carboxylic acid (Example 18A) are dissolved in 4 ml of DMF and, after addition of 150 mg (0.39 mmol) of HATU and 36 mg (0.3 mmol) of DMAP, stirred at room temperature for 15 minutes. 43 mg (0.39 mmol) of (pyridin-3-ylmethyl)amine are added dropwise to this solution, and the mixture is stirred overnight. The reaction mixture is purified by preparative HPLC.

Yield: 61 mg (81% of theory)
LC-MS (Method 8): $R_t$=2.04 min.
MS (ESI$^+$): m/z=383 [M+H]$^+$
$^1$H-NMR (300 MHz, DMSO-$d_6$): δ=9.82 (s, 1H), 9.00 (t, 1H), 8.87 (s, 1H), 8.81 (d, 1H), 8.51 (d, 1H), 8.01 (dd, 1H), 7.45 (dd, 1H), 7.27 (s, 1H), 7.14 (t, 1H), 7.02 (dd, 1H), 4.60 (d, 2H), 3.91 (s, 3H), 2.15 (s, 3H) ppm.

Example 2

4-({[(3-Fluoro-4-methylphenyl)amino]carbonyl}amino)-N-[1-(6-methoxypyridin-3-yl)ethyl]-1-methyl-1H-imidazole-2-carboxamide

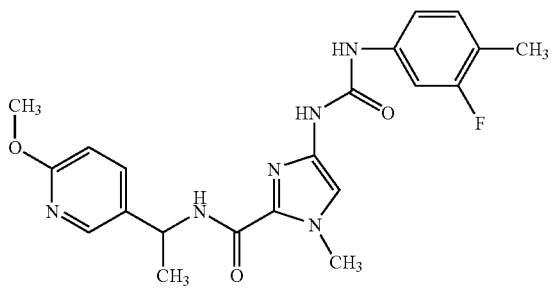

60 mg (0.2 mmol) of 4-({[(4-methyl-3-fluorophenyl)amino]carbonyl}amino)-1-methyl-1H-imidazole-2-carboxylic acid (Example 18A) are dissolved in 4 ml of DMF and, after addition of 150 mg (0.39 mmol) of HATU and 36 mg (0.3 mmol) of DMAP, stirred at room temperature for 15 minutes. 60 mg (0.39 mmol) of [1-(6-methoxypyridin-3-yl)ethyl]amine are added to this solution and the mixture is stirred overnight. The reaction mixture is purified by preparative HPLC. The correct fractions are evaporated in vacuo.

Yield: 71 mg (85% of theory)
LC-MS (Method 8): $R_t$=2.88 min.
MS (ESI$^+$): m/z=427 [M+H]$^+$
$^1$H-NMR (300 MHz, DMSO-d$_6$): δ=9.20 (s, 1H), 8.70 (s, 1H), 8.48 (d, 1H), 8.17 (d, 1H), 7.84 (dd, 1H), 7.44 (dd, 1H), 7.20 (s, 1H), 7.16 (dd, 1H), 7.01 (dd, 1H), 6.79 (d, 1H), 5.07 (m, 1H), 3.88 (s, 3H), 3.83 (s, 3H), 2.16 (s, 3H), 1.49 (d, 3H) ppm.

Example 3

4-({[(4-Chloro-2-methylphenyl)amino]carbonyl}amino)-1-(cyclopropylmethyl)-N-(3-morpholin-4-ylpropyl)-1H-imidazole-2-carboxamide

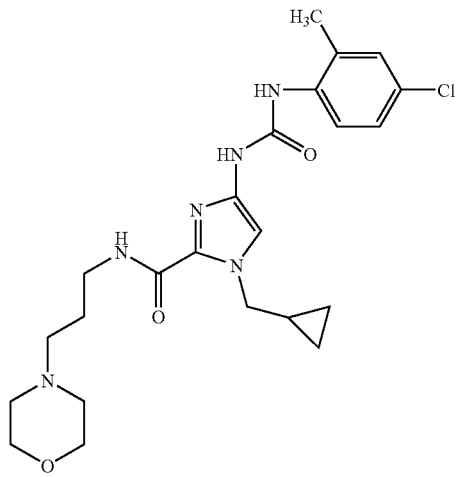

34.8 mg (0.1 mmol) of 4-({[(4-chloro-2-methylphenyl)amino]carbonyl}amino)-1-(cyclopropylmethyl)-1H-imidazole-2-carboxylic acid (Example 4A) are dissolved in 0.3 ml of DMF and, after addition of 39.7 mg (0.1 mmol) of HBTU and 10.12 mg (14 μl; 0.1 mmol) of triethylamine, stirred at room temperature for 30 minutes. This solution is added to a solution of 28.8 mg (0.2 mmol) of (3-morpholin-4-ylpropyl)amine in 0.1 ml of DMF and shaken overnight. After filtration, the reaction mixture is purified by preparative HPLC (column: Macherey-Nagel VP 50/21 Nucleodur C18 gravity, 5 μm; flow rate: 25 ml/min; eluent A: acetonitrile, eluent B: water+0.1% conc. aqueous ammonia solution, gradient: 0 min 10% A, 2.00 min 10% A, 6.00 min 90% A, 7.00 min 90% A, 7.10 min 10% A, 8 min 10% A; running time: ca. 10 min per separation; wave length: 220 nm). The correct fractions are evaporated in vacuo.

Yield: 32 mg (67% of theory)
LC-MS (Method 2): $R_t$=1.66 min.
MS (ESI$^+$): m/z=475 [M+H]$^+$
$^1$H-NMR (400 MHz, DMSO-d$_6$): δ=9.1 (s, 1H), 8.7-8.0 (s very broad, 1H), 8.2 (s, 1H), 7.9 (d, 1H), 7.25 (s, 1H), 7.2 (m, 2H), 4.25 (d, 2H), 3.6 (tr, 4H), 3.25 (q, 2H), 2.3 (m, 6H), 2.25 (s, 3H), 1.65 (quintet, 2H), 1.25 (m, 1H), 0.5 (q, 2H), 0.35 (q, 2H) ppm.

Example 4

1-(2-Methoxyethyl)-N-(pyridin-3-ylmethyl)-4-[({[4-(trifluoromethoxy)phenyl]amino}-carbonyl)amino]-1H-imidazole-2-carboxamide

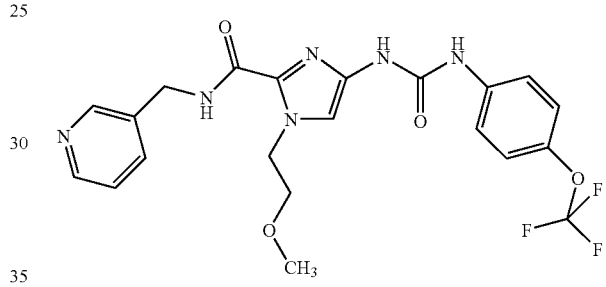

38.8 mg (0.1 mmol) of 1-(2-methoxyethyl)-4-[({[4-(trifluoromethoxy)phenyl]amino}-carbonyl)amino]-1H-imidazole-2-carboxylic acid (Example 9A) are dissolved in 0.4 ml of DMF and, after addition of 81 mg (0.5 mmol) of N,N-carbonyldiimidazole, stirred at room temperature for 50 minutes. Then 18 μl (18 mg; 1 mmol) of water are added, and the mixture is stirred at room temperature for 30 minutes. Addition of 21.6 mg (0.2 mmol) of 3-picolylamine is followed by stirring at room temperature for 90 minutes. After filtration, the reaction mixture is purified by preparative HPLC (column: Macherey-Nagel VP 50/21 Nucleodur C18 gravity, 5 μm; flow rate: 25 ml/min; eluent A: acetonitrile, eluent B: water+0.1% conc. aqueous ammonia solution, gradient: 0 min 10% A, 2.00 min 10% A, 6.00 min 90% A, 7.00 min 90% A, 7.10 min 10% A, 8 min 10% A; running time: ca. 10 min per separation; wave length: 220 nm). The correct fractions are evaporated in vacuo.

Yield: 15.8 mg (33% of theory)
LC-MS (Method 5): $R_t$=1.87 min.
MS (ESI$^+$): m/z=479 [M+H]$^+$
$^1$H-NMR (400 MHz, DMSO-d$_6$): δ=9.1 (s, 1H), 8.8 (tr, 1H), 8.7 (s, 1H), 8.55 (s, 1H), 8.45 (d, 1H), 7.7 (d, 1H), 7.55 (d, 2H), 7.35 (dd, 1H), 7.3 (m, 3H), 4.55 (tr, 2H), 4.4 (d, 2H), 3.6 (tr, 2H), 3.25 (s, 3H) ppm.

Example 5 to 121 listed in Table 1 are prepared in analogy to Examples 3 and 4.

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 5 | 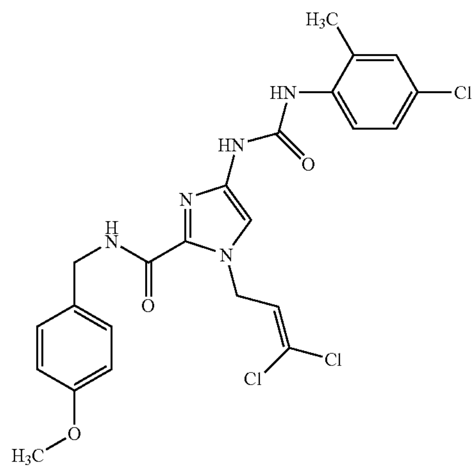 | 522.82 | 522 | 2.85 (2) | Example 16A | 3 | 26 (50) |
| 6 | 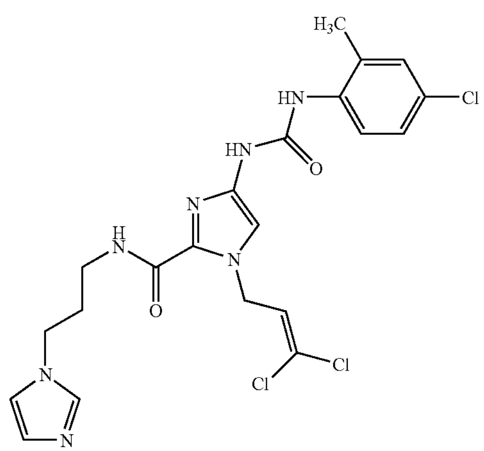 | 510.81 | 510 | 1.82 (2) | Example 16A | 3 | 22 (43) |
| 7 | 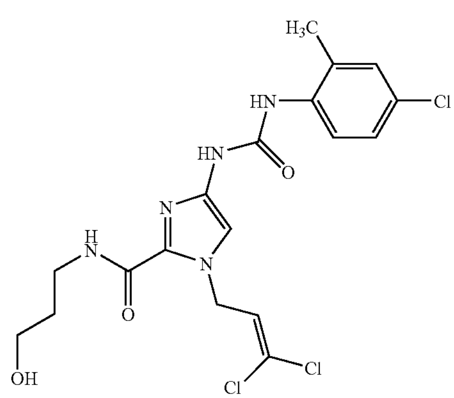 | 460.75 | 460 | 2.29 (2) | Example 16A | 3 | 20 (43) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 8 | 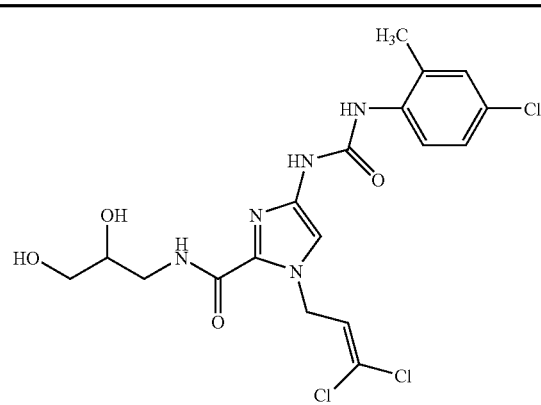 | 476.75 | 476 | 2.13 (2) | Example 16A | 3 | 2.7 (6) |
| 9 | 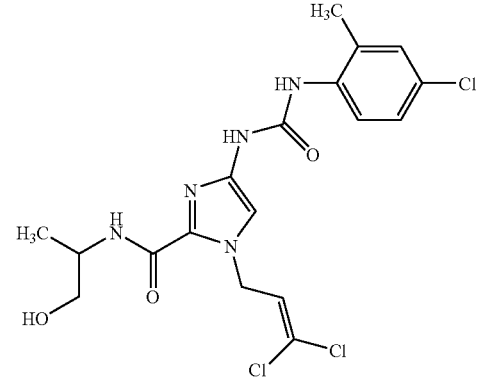 | 460.75 | 460 | 2.35 (2) | Example 16A | 3 | 18 (39) |
| 10 | 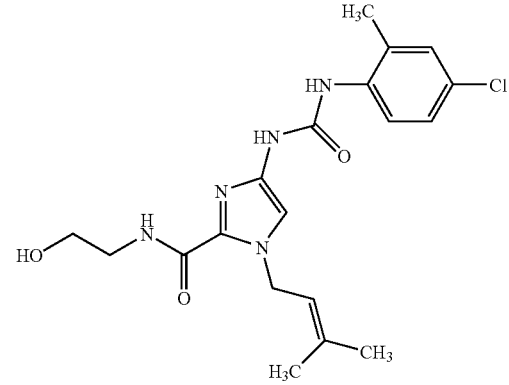 | 405.88 | 406 | 2.22 (2) | Example 12A | 3 | 33 (81) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 11 | 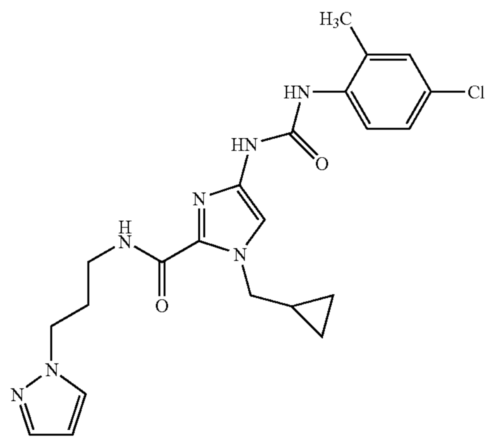 | 455.95 | 456 | 2.35 (2) | Example 4A | 3 | 21 (46) |
| 12 | 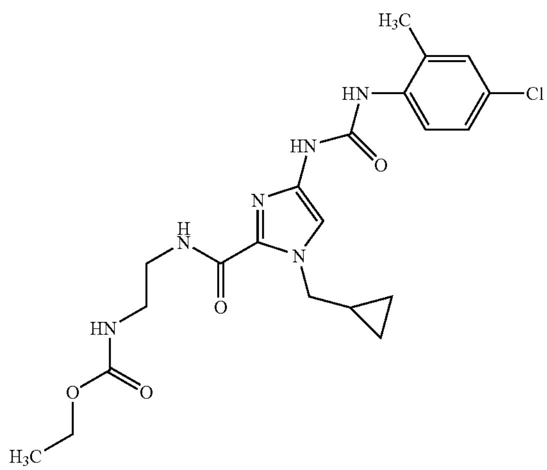 | 462.94 | 463 | 2.31 (2) | Example 4A | 3 | 21 (45) |
| 13 | 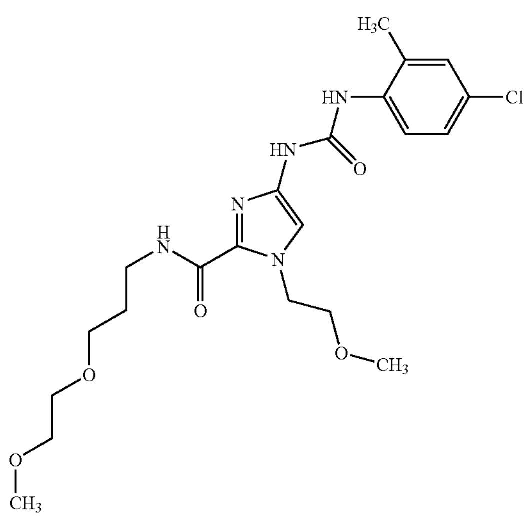 | 467.95 | 468 | 2.12 (2) | Example 8A | 3 | 29(62) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 14 | 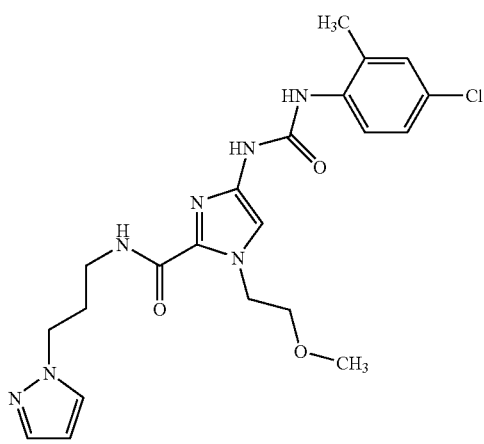 | 459.94 | 460 | 2.13 (2) | Example 8A | 3 | 22 (48) |
| 15 | 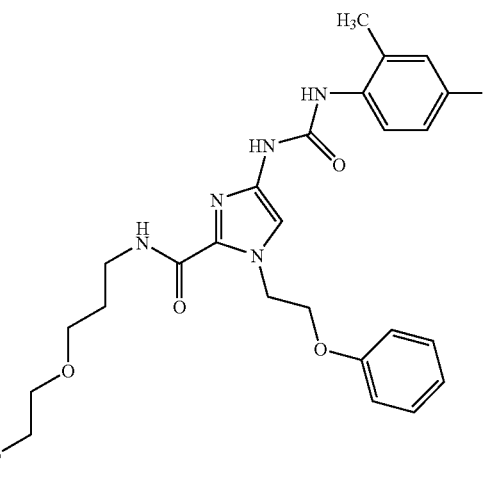 | 530.02 | 531 | 2.54 (2) | Example 14A | 3 | 19 (36) |
| 16 | 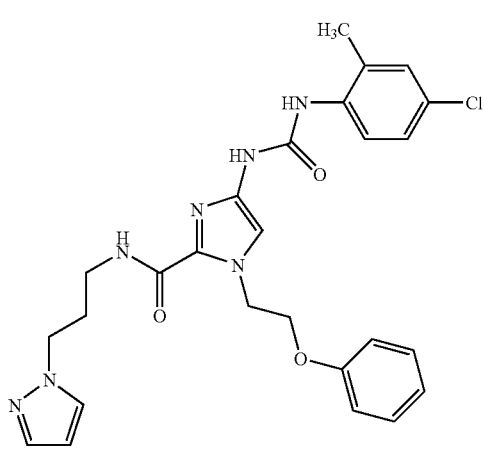 | 522.01 | 523 | 2.53 (2) | Example 14A | 3 | 17 (33) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 17 | 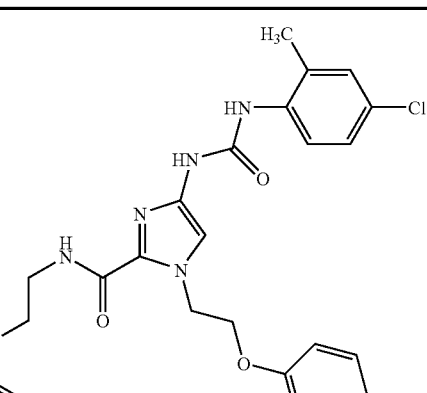 | 528.99 | 529 | 2.49 (2) | Example 14A | 3 | 16 (30) |
| 18 | 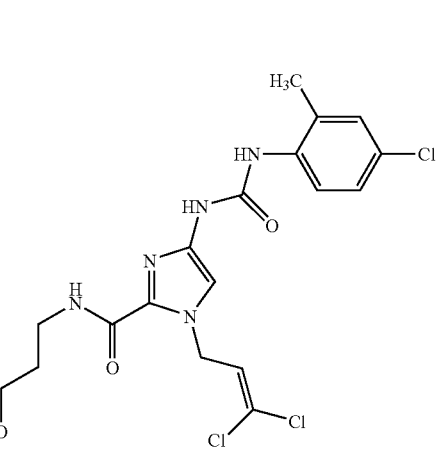 | 518.83 | 518 | 2.57 (2) | Example 16A | 3 | 8 (15) |
| 19 | 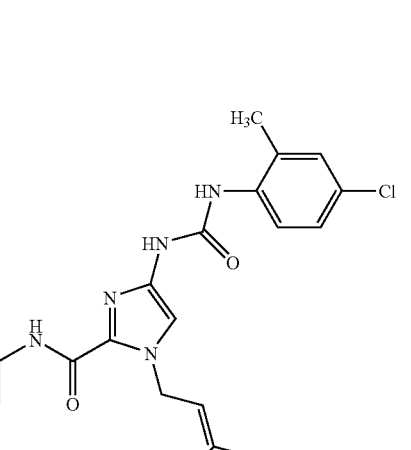 | 510.81 | 510 | 2.55 (2) | Example 16A | 3 | 28 (55) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 20 | 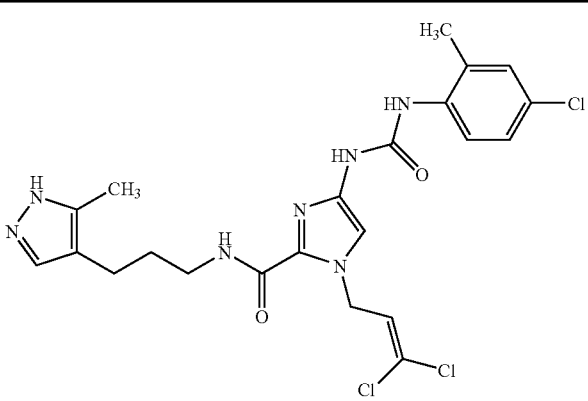 | 524.84 | 524 | 1.84 (2) | Example 16A | 3 | 25 (48) |
| 21 | 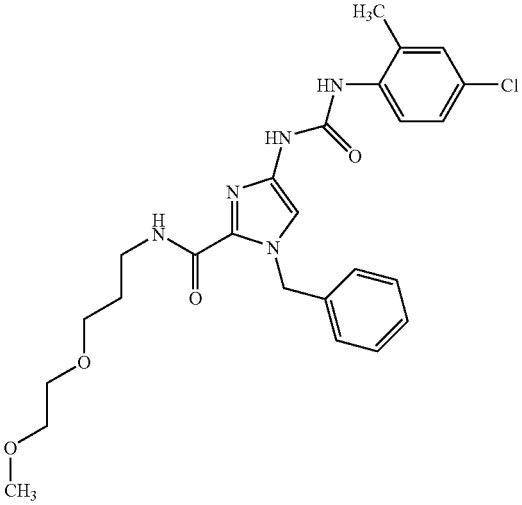 | 500.00 | 500 | 2.49 (2) | Example 10A | 3 | 21(42) |
| 22 | 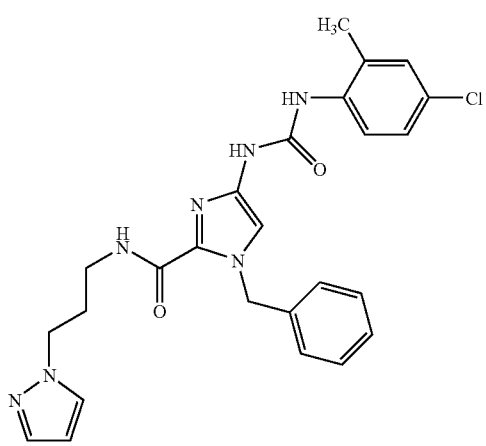 | 491.98 | 492 | 2.48 (2) | Example 10A | 3 | 15 (30) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 23 | 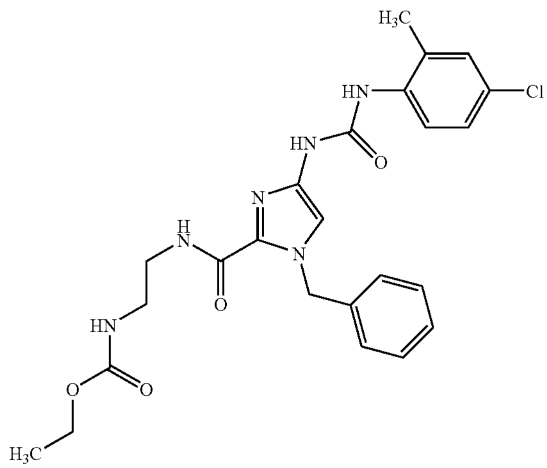 | 498.97 | 499 | 2.45 (2) | Example 10A | 3 | 3.3 (7) |
| 24 | 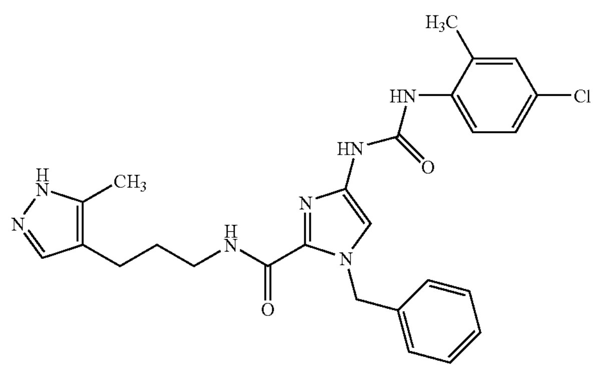 | 506.01 | 507 | 2.33 (2) | Example 10A | 3 | 26 (51) |
| 25 | 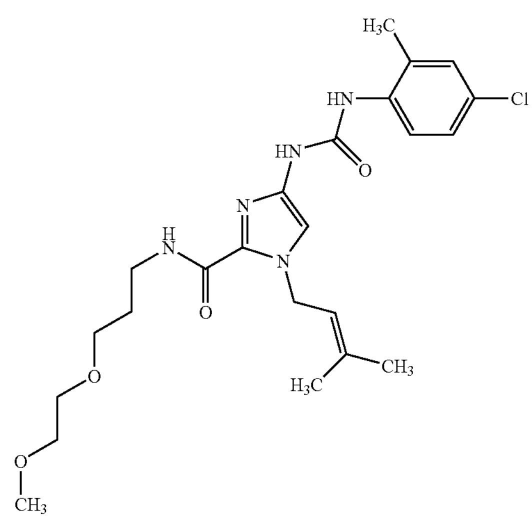 | 477.99 | 478 | 2.52 (2) | Example 12A | 3 | 21 (44) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 26 | 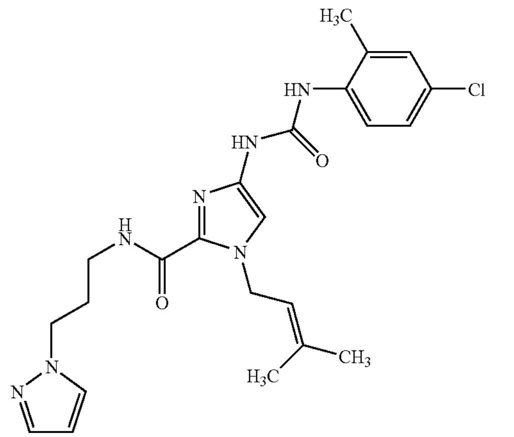 | 469.97 | 470 | 2.52 (2) | Example 12A | 3 | 24 (51) |
| 27 | 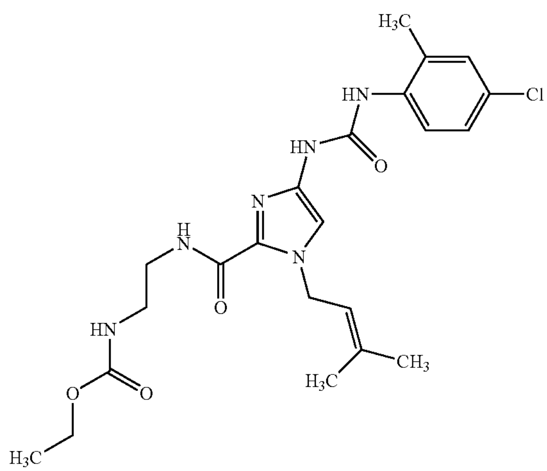 | 476.96 | 477 | 2.47 (2) | Example 12A | 3 | 22 (46) |
| 28 | 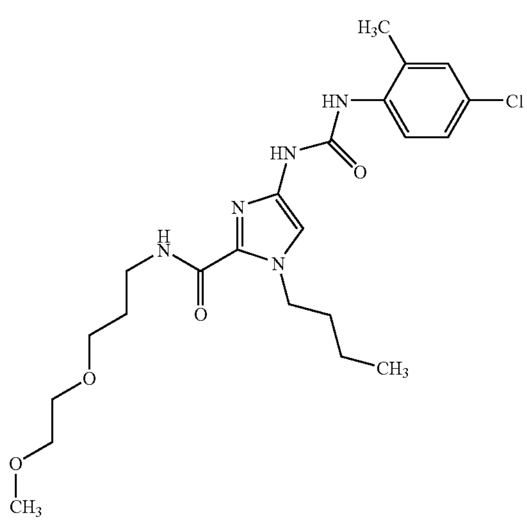 | 465.98 | 466 | 2.47 (2) | Example 6A | 3 | 26 (56) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 29 | 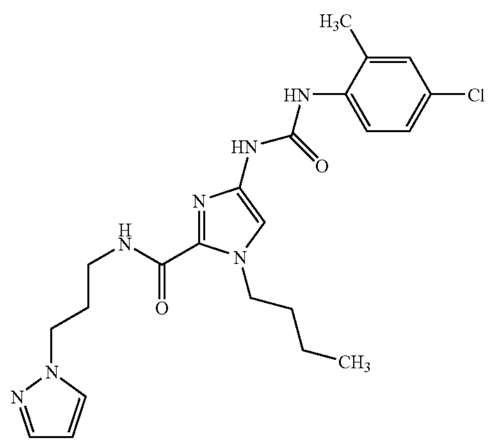 | 457.96 | 458 | 2.47 (2) | Example 6A | 3 | 29 (63) |
| 30 | 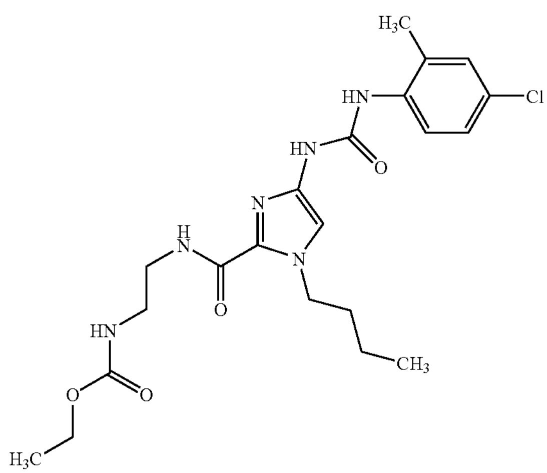 | 464.95 | 465 | 2.42 (2) | Example 6A | 3 | 13 (28) |
| 31 | 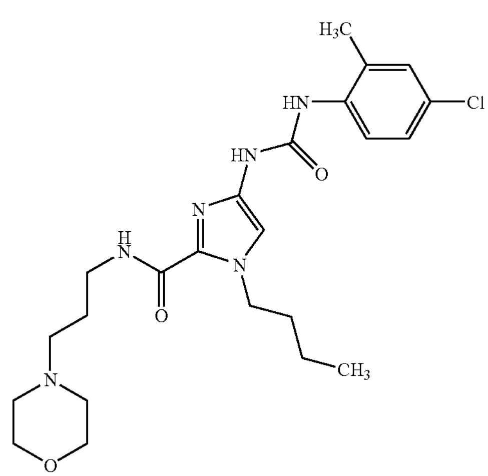 | 477.01 | 478 | 1.78 (2) | Example 6A | 3 | 34 (71) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 32 | 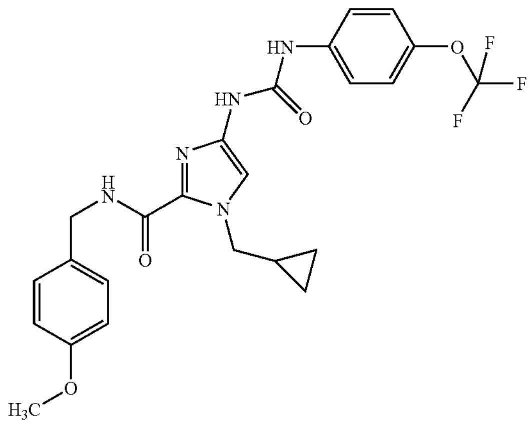 | 503.48 | 504 | 2.75 (2) | Example 5A | 3 | 11 (22) |
| 33 | 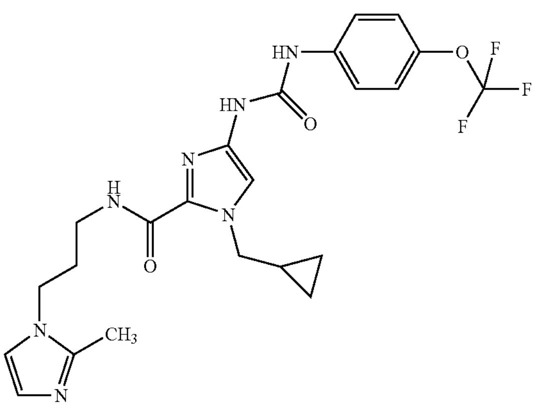 | 505.50 | 506 | 1.93 (2) | Example 5A | 3 | 12 (24) |
| 34 | 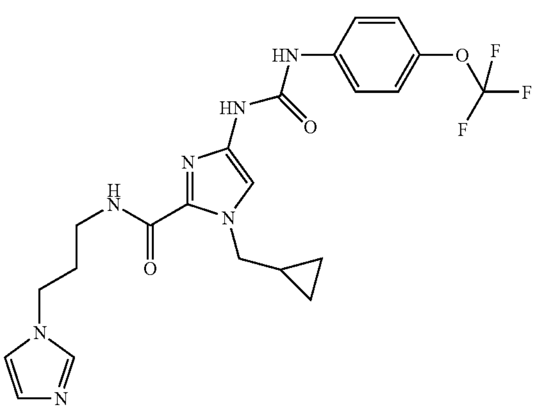 | 491.47 | 492 | 1.90 (2) | Example 5A | 3 | 11 (22) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 35 | 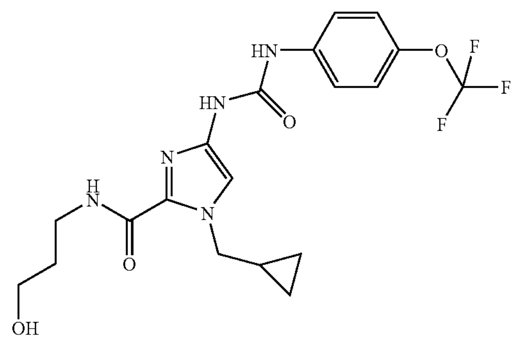 | 441.41 | 442 | 2.22 (2) | Example 5A | 3 | 12 (27) |
| 36 | 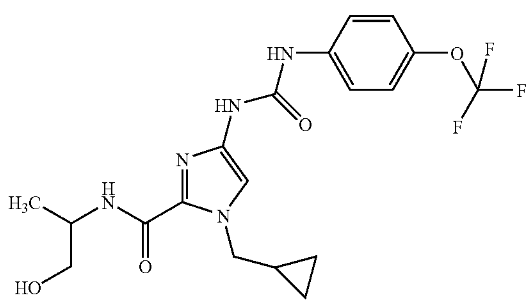 | 441.41 | 442 | 2.28 (2) | Example 5A | 3 | 12 (27) |
| 37 | 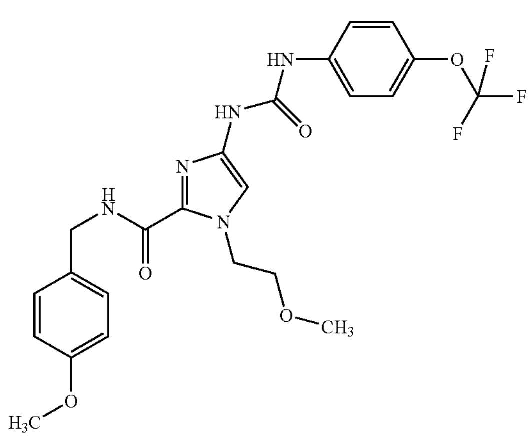 | 507.47 | 508 | 2.54 (2) | Example 9A | 3 | 28 (55) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 38 | 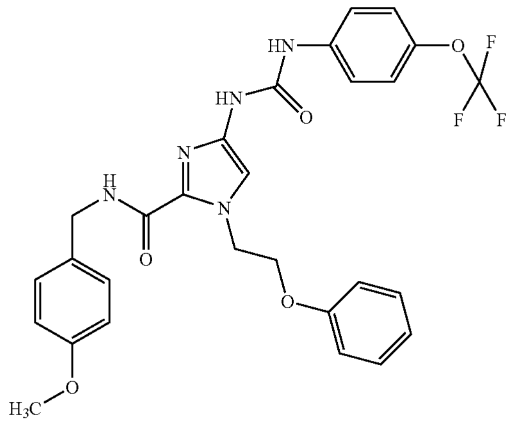 | 569.54 | 570 | 2.90 (1) | Example 15A | 3 | 28 (49) |
| 39 | 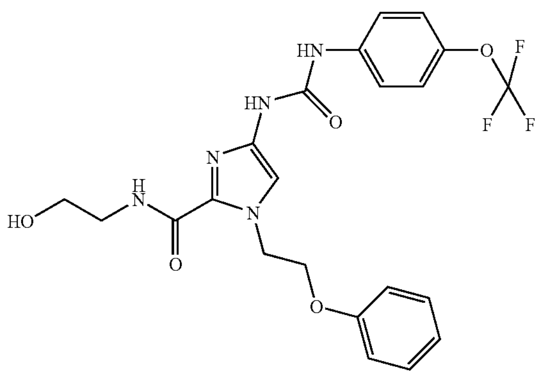 | 493.44 | 494 | 2.38 (2) | Example 15A | 3 | 23 (47) |
| 40 | 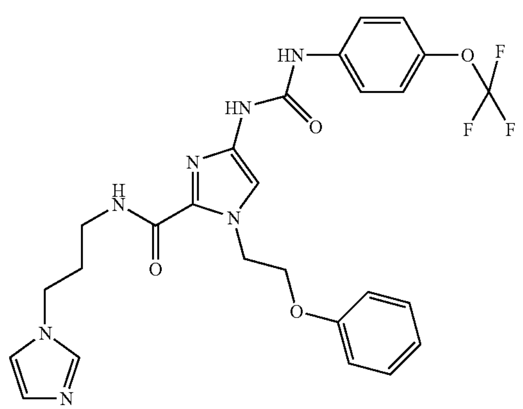 | 557.53 | 558 | 2.07 (2) | Example 15A | 3 | 25 (45) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 41 | 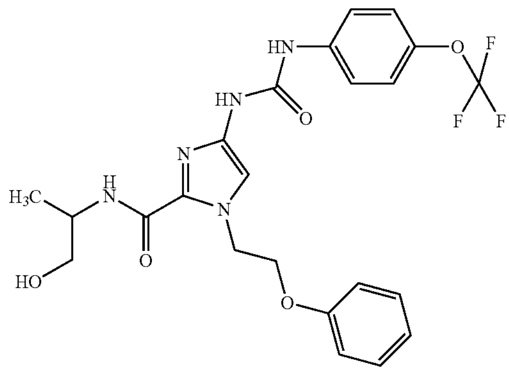 | 507.47 | 508 | 2.45 (2) | Example 15A | 3 | 26 (51) |
| 42 | 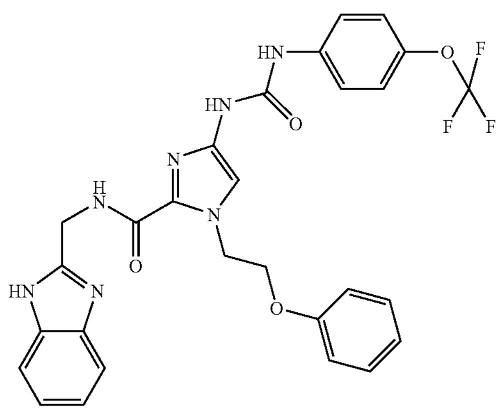 | 579.54 | 580 | 2.22 (1) | Example 15A | 3 | 33 (57) |
| 43 | 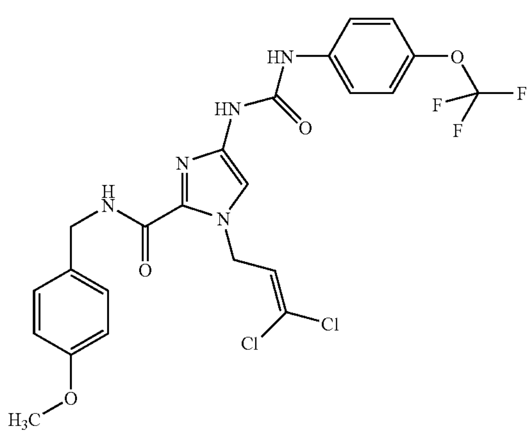 | 558.34 | 558 | 2.97 (1) | Example 17A | 3 | 12 (21) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 44 | 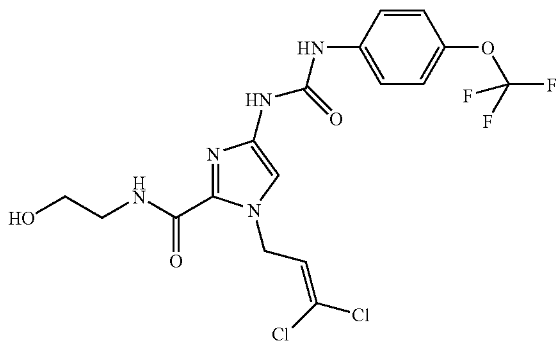 | 482.24 | 482 | 2.38 (2) | Example 17A | 3 | 22 (46) |
| 45 | 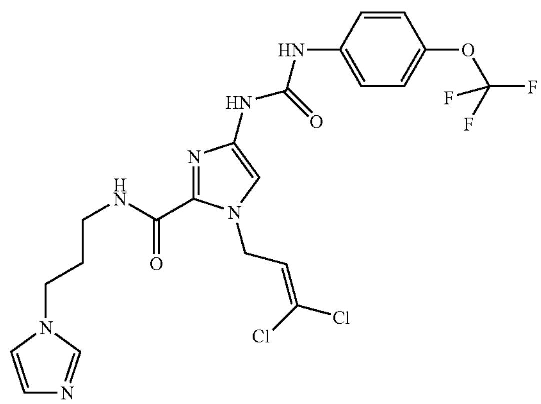 | 546.34 | 546 | 2.09 (2) | Example 17A | 3 | 14 (26) |
| 46 | 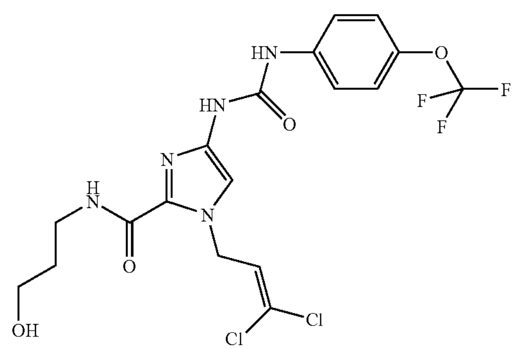 | 496.27 | 496 | 2.41 (2) | Example 17A | 3 | 11 (22) |
| 47 | 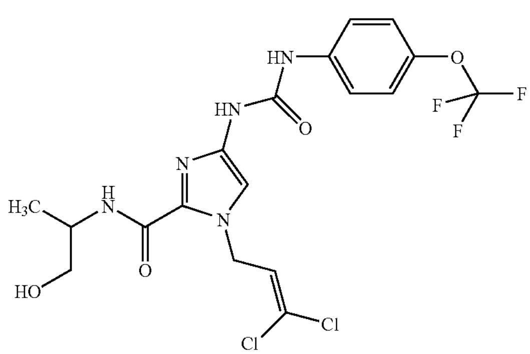 | 496.27 | 496 | 2.46 (2) | Example 17A | 3 | 13 (26) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 48 | 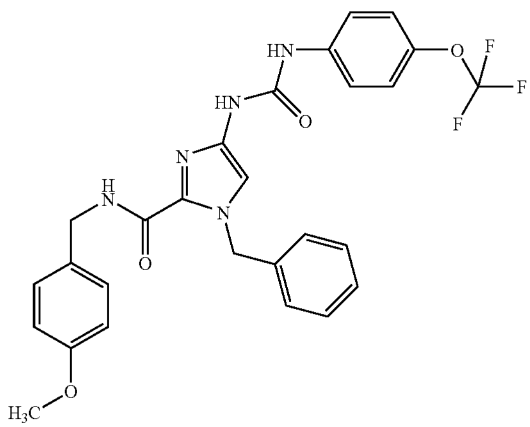 | 539.51 | 540 | 2.87 (1) | Example 11A | 3 | 21 (39) |
| 49 | 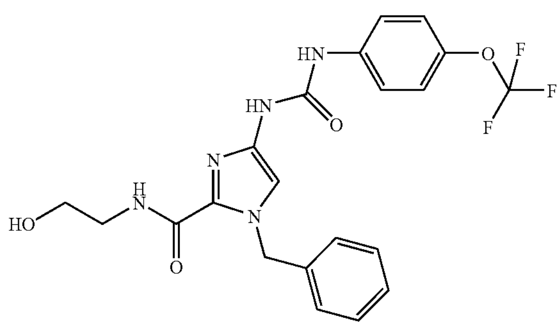 | 463.41 | 464 | 2.32 (2) | Example 11A | 3 | 21 (45) |
| 50 | 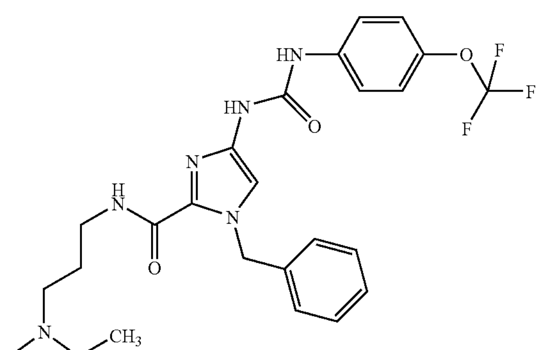 | 541.53 | 542 | 2.10 (2) | Example 11A | 3 | 14 (26) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 51 | 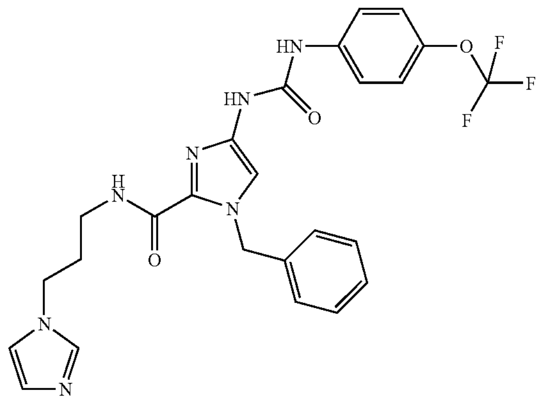 | 527.51 | 528 | 2.07 (2) | Example 11A | 3 | 20 (38) |
| 52 | 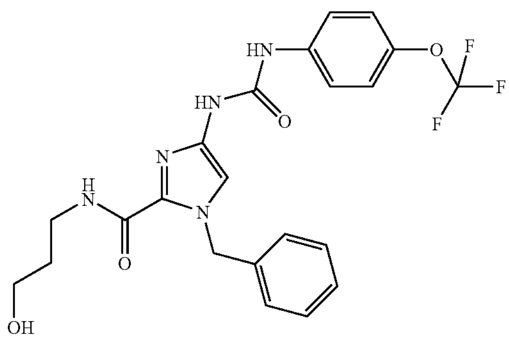 | 477.44 | 478 | 2.35 (2) | Example 11A | 3 | 21 (44) |
| 53 | 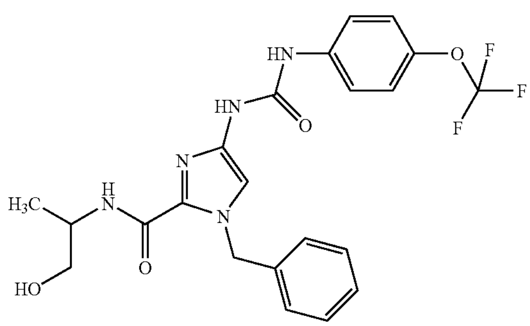 | 477.44 | 478 | 2.40 (2) | Example 11A | 3 | 25 (52) |
| 54 | 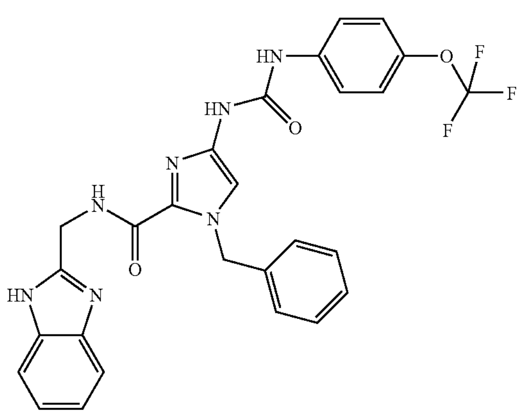 | 549.51 | 550 | 2.25 (2) | Example 11A | 3 | 34 (62) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 55 | 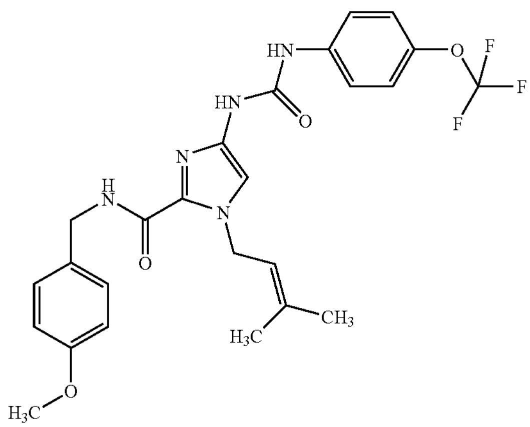 | 517.51 | 518 | 2.93 (1) | Example 13A | 3 | 27 (52) |
| 56 | 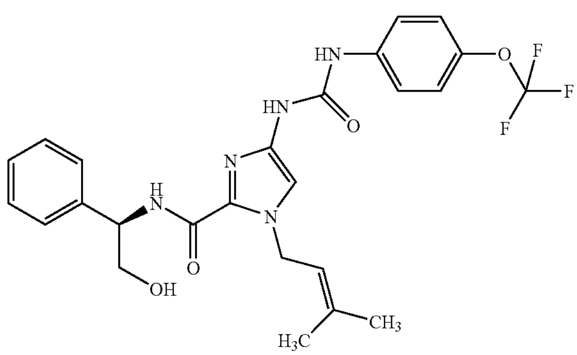 | 517.51 | 518 | 2.68 (2) | Example 13A | 3 | 30 (58) |
| 57 | 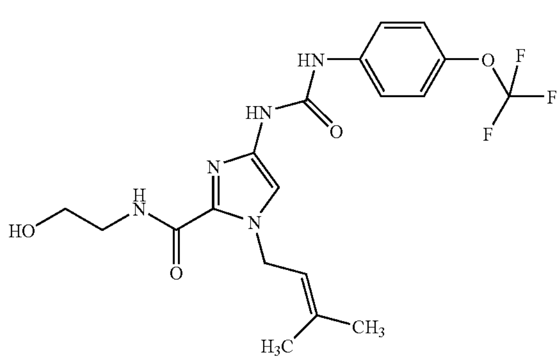 | 441.41 | 442 | 2.34 (2) | Example 13A | 3 | 12 (27) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 58 | 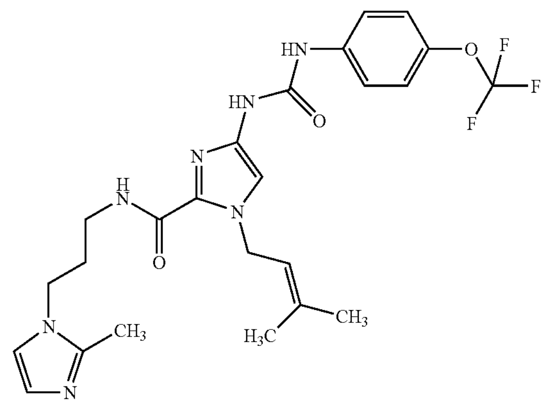 | 519.53 | 520 | 2.09 (2) | Example 13A | 3 | 22 (42) |
| 59 | 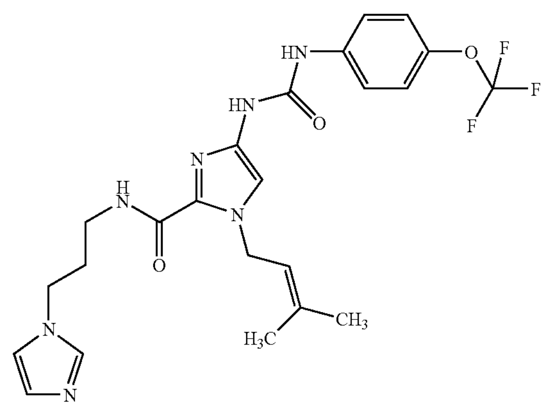 | 505.50 | 506 | 1.99 (2) | Example 13A | 3 | 34 (67) |
| 60 | 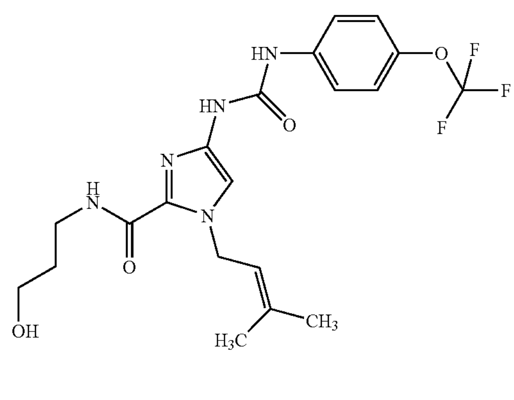 | 455.44 | 456 | 2.40 (1) | Example 13A | 3 | 38 (83) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 61 | 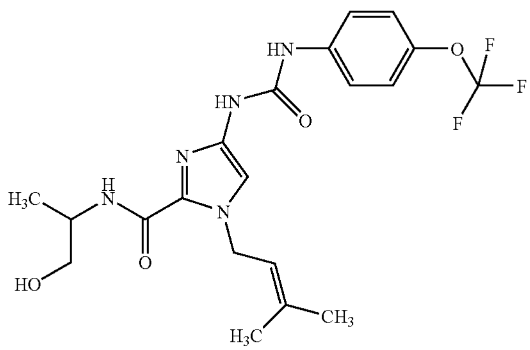 | 455.44 | 456 | 2.46 (1) | Example 13A | 3 | 32 (70) |
| 62 | 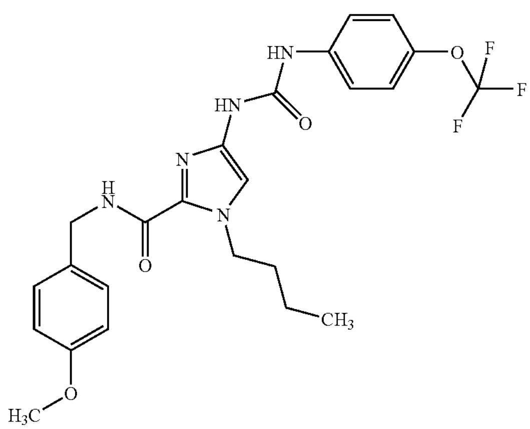 | 505.49 | 506 | 2.88 (1) | Example 7A | 3 | 23 (46) |
| 63 | 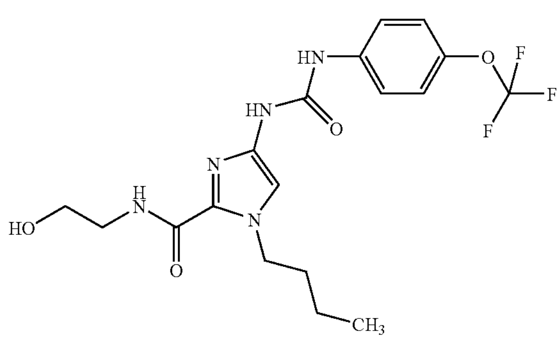 | 429.40 | 430 | 2.32 (1) | Example 7A | 3 | 24 (56) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 64 | 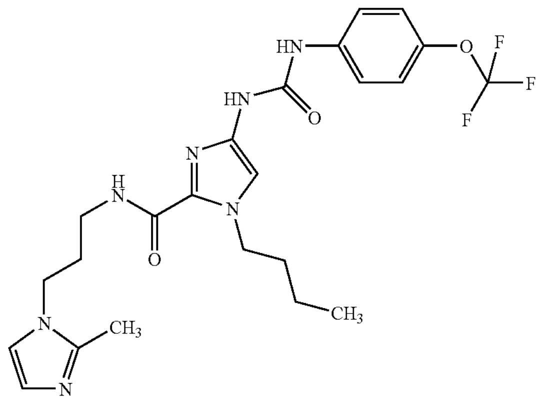 | 507.51 | 508 | 1.95 (1) | Example 7A | 3 | 23 (45) |
| 65 | 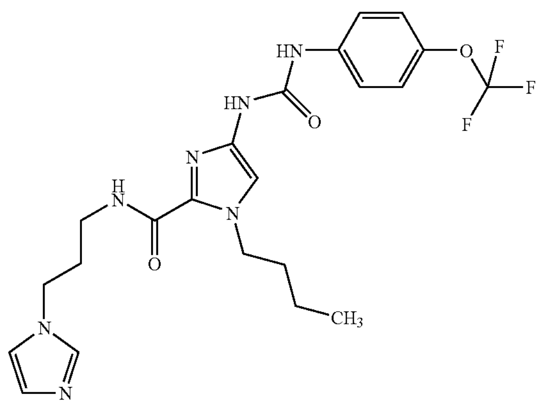 | 493.49 | 494 | 1.91 (1) | Example 7A | 3 | 27 (55) |
| 66 | 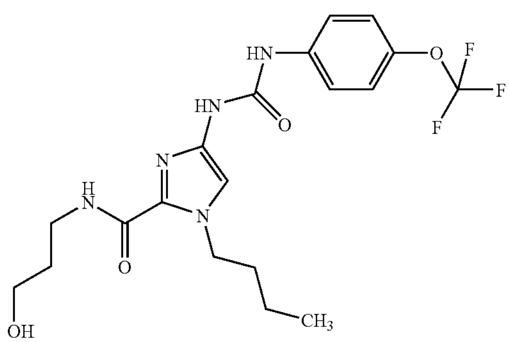 | 443.42 | 444 | 2.35 (1) | Example 7A | 3 | 20 (45) |
| 67 | 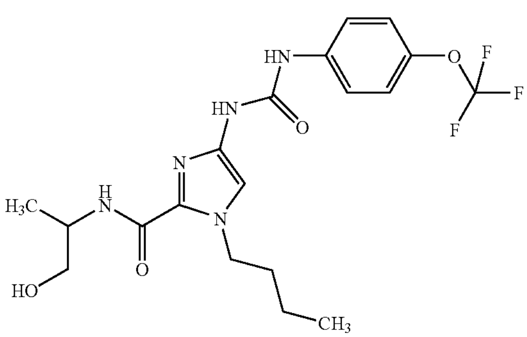 | 443.42 | 444 | 2.41 (1) | Example 7A | 3 | 28 (63) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 68 | 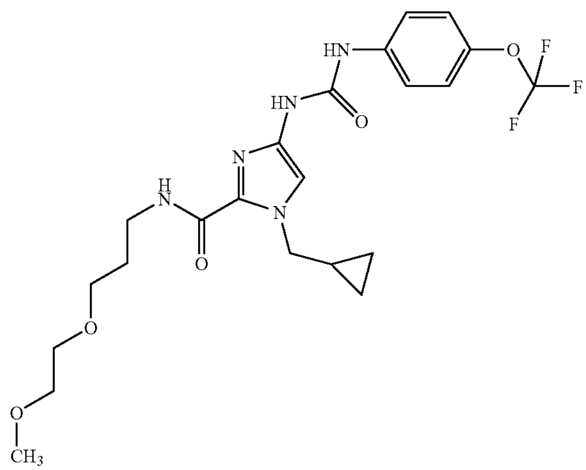 | 499.49 | 500 | 2.49 (1) | Example 5A | 3 | 13 (26) |
| 69 | 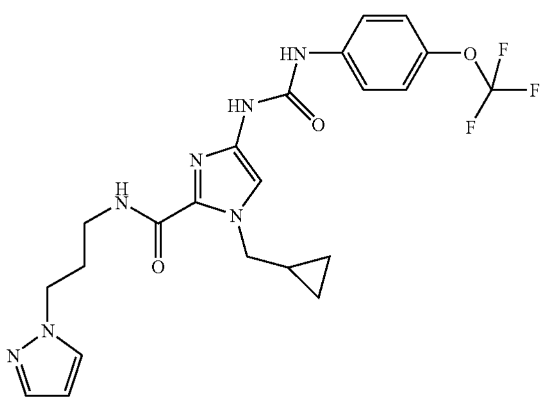 | 491.47 | 492 | 2.49 (1) | Example 5A | 3 | 14 (28) |
| 70 | 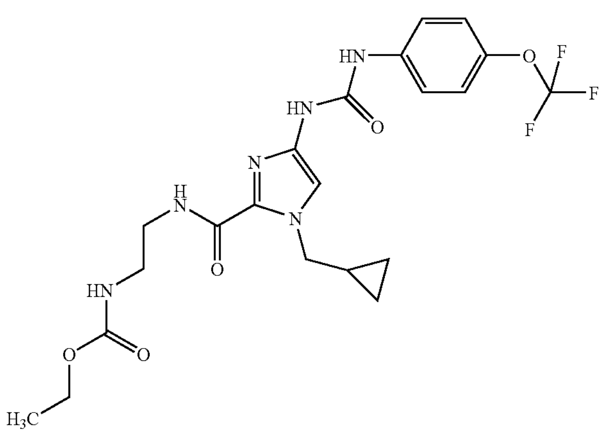 | 498.46 | 499 | 2.46 (1) | Example 5A | 3 | 11 (22) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 71 | 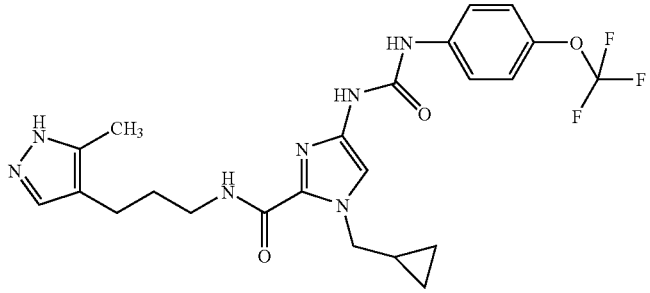 | 505.50 | 506 | 2.34 (1) | Example 5A | 3 | 16 (32) |
| 72 | 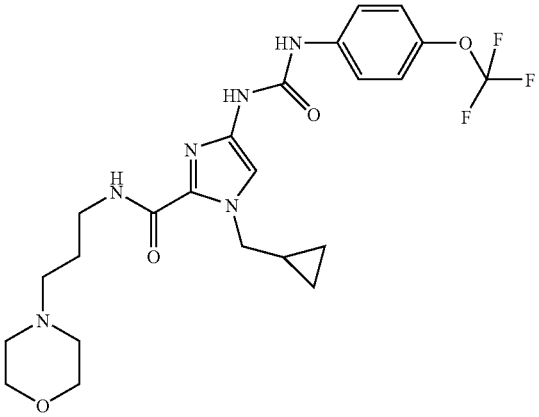 | 510.51 | 511 | 1.84 (1) | Example 5A | 3 | 13 (25) |
| 73 | 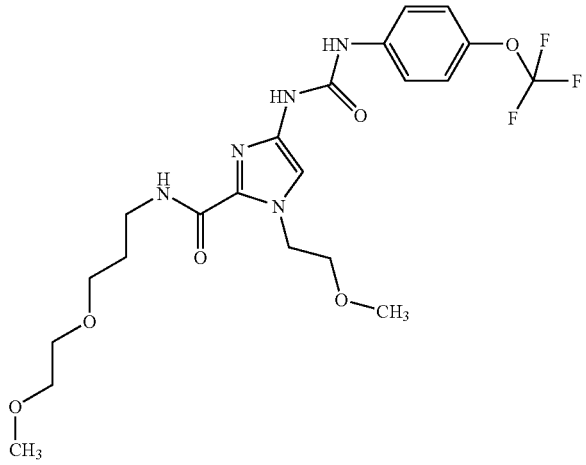 | 503.48 | 504 | 2.26 (1) | Example 9A | 3 | 31 (62) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 74 | 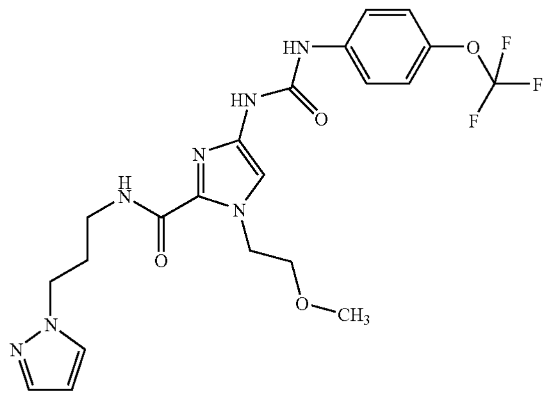 | 495.46 | 496 | 2.28 (1) | Example 9A | 3 | 30 (61) |
| 75 | 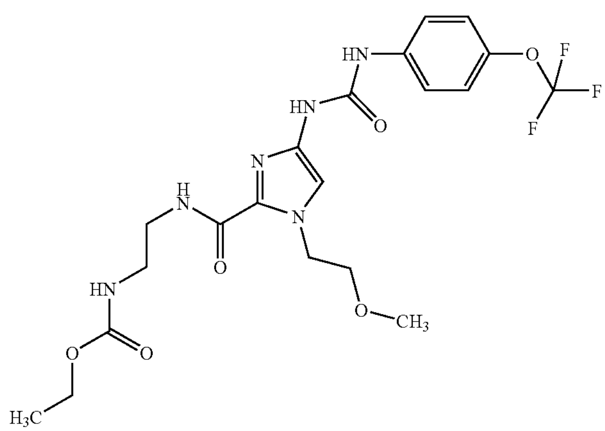 | 502.45 | 503 | 2.25 (1) | Example 9A | 3 | 22 (44) |
| 76 | 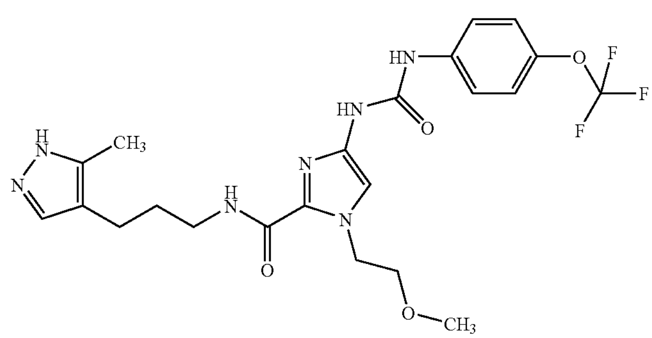 | 509.49 | 510 | 2.12 (1) | Example 9A | 3 | 27 (53) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 77 | 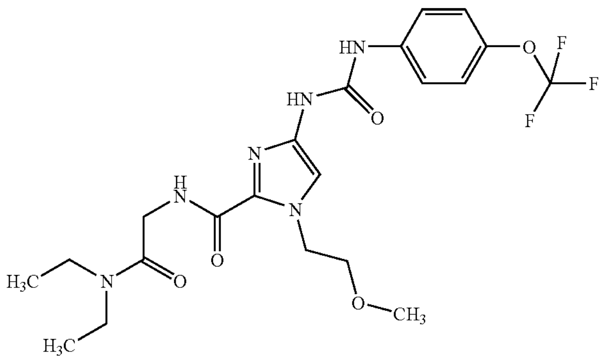 | 500.48 | 501 | 2.38 (1) | Example 9A | 3 | 21 (42) |
| 78 | 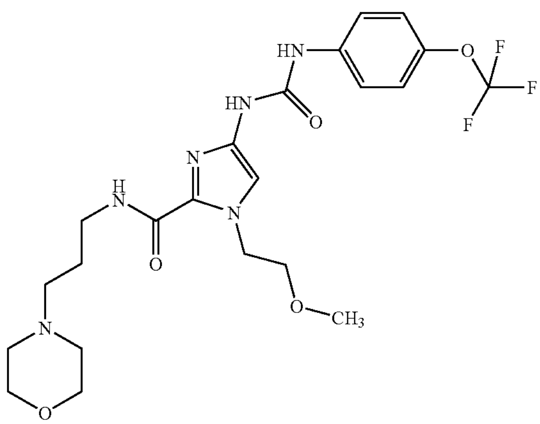 | 514.50 | 515 | 1.67 (1) | Example 9A | 3 | 34 (66) |
| 79 | 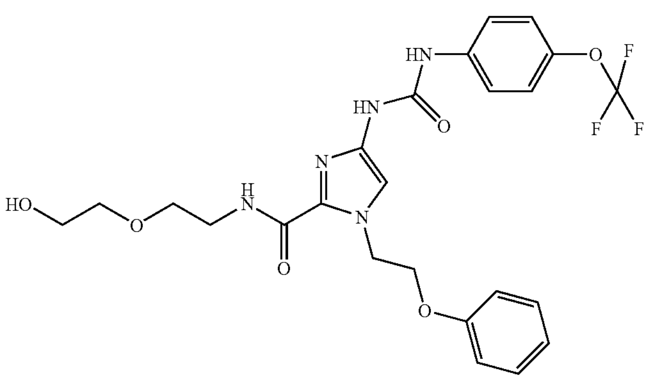 | 537.49 | 538 | 2.42 (1) | Example 15A | 3 | 30 (56) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 80 | 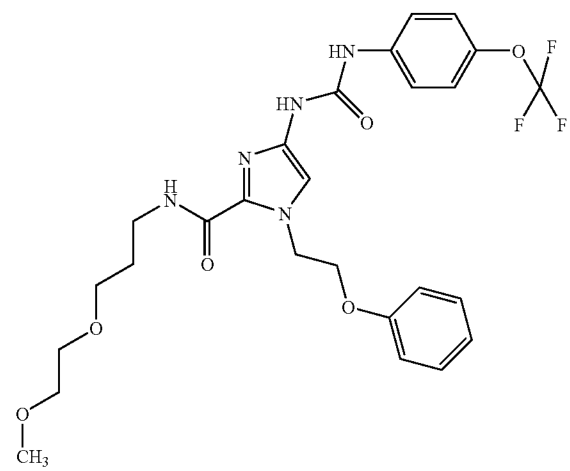 | 565.55 | 566 | 2.65 (1) | Example 15A | 3 | 11 (19) |
| 81 | 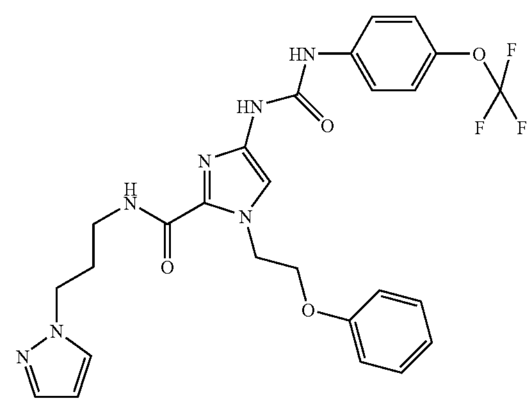 | 557.53 | 558 | 2.64 (1) | Example 15A | 3 | 3.5 (6) |
| 82 | 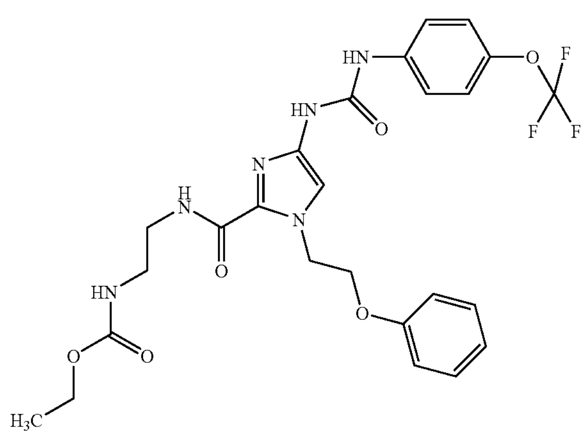 | 564.52 | 565 | 2.62 (1) | Example 15A | 3 | 5.2 (9) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 83 | 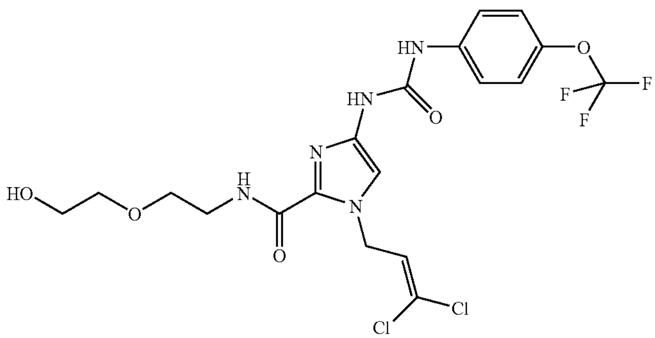 | 526.30 | 526 | 2.43 (1) | Example 17A | 3 | 23 (44) |
| 84 | 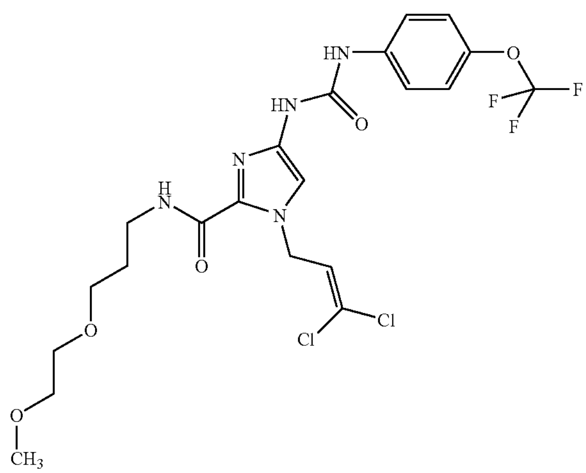 | 554.35 | 554 | 2.69 (1) | Example 17A | 3 | 22 (40) |
| 85 | 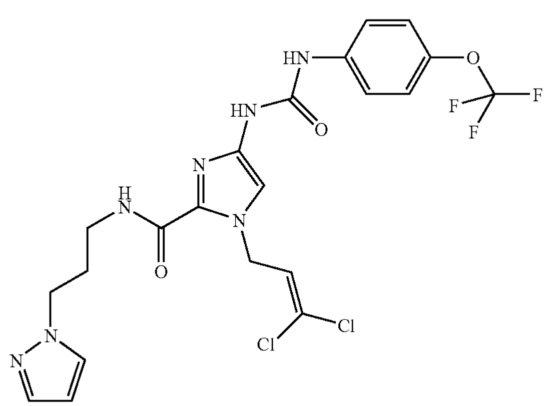 | 546.34 | 546 | 2.67 (1) | Example 17A | 3 | 18 (33) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 86 | 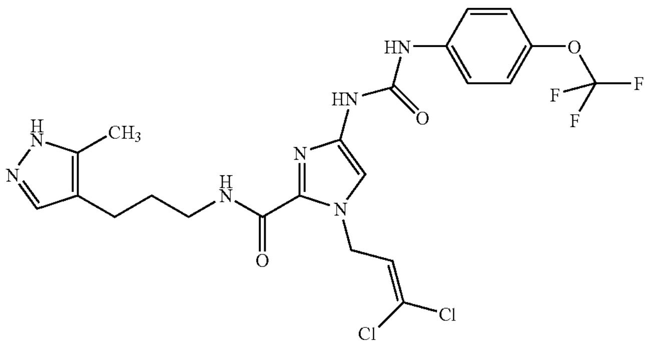 | 560.36 | 560 | 2.53 (1) | Example 17A | 3 | 29 (52) |
| 87 | 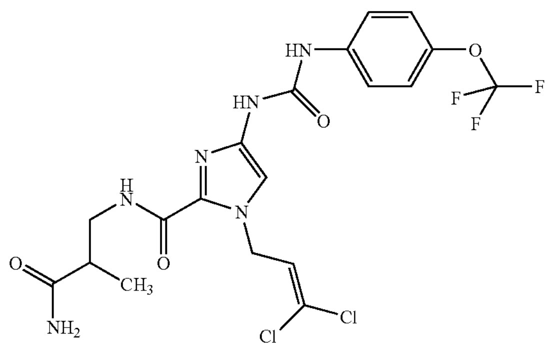 | 523.30 | 523 | 2.40 (1) | Example 17A | 3 | 14 (27) |
| 88 | 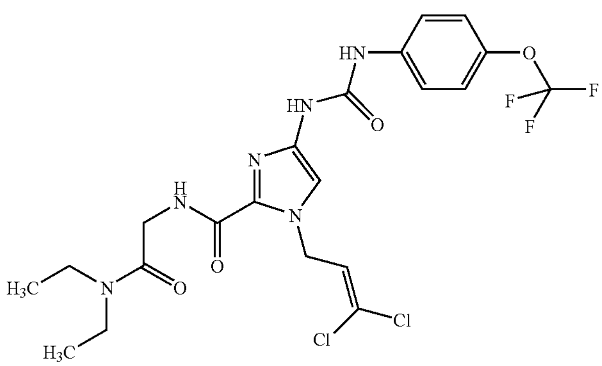 | 551.35 | 551 | 2.79 (1) | Example 17A | 3 | 26 (47) |
| 89 | 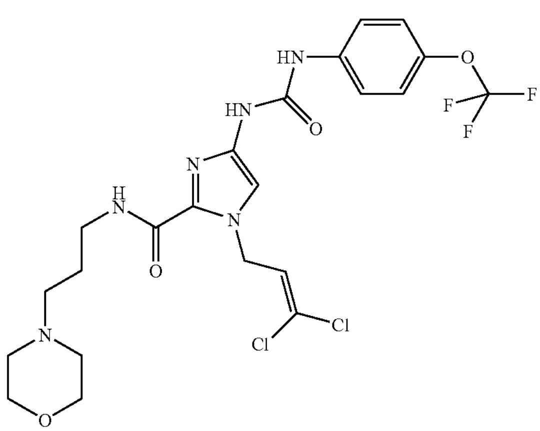 | 565.38 | 565 | 1.96 (1) | Example 17A | 3 | 22 (39) |

-continued

| Example No. | Structure | Mol. mass | MS (EI) [M + H]⁺ | LC-MS retention time [min] (method) | Starting compound | Preparation in analogy to Example No. | Yield [mg] % of theory |
|---|---|---|---|---|---|---|---|
| 90 | 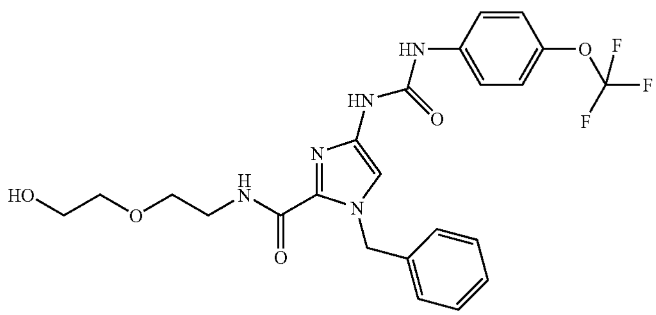 | 507.47 | 508 | 2.37 (1) | Example 11A | 3 | 19 (37) |
| 91 | 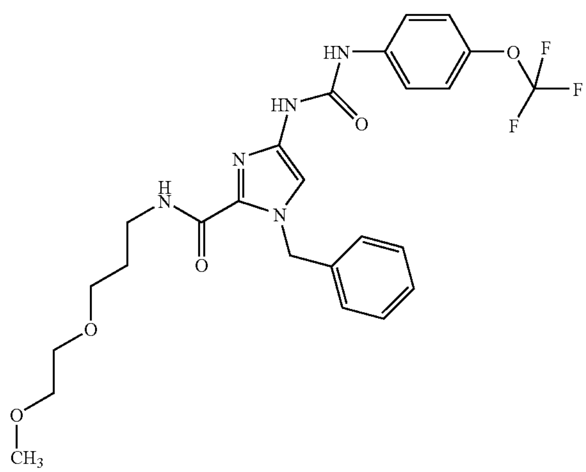 | 535.52 | 536 | 2.61 (1) | Example 11A | 3 | 22 (41) |
| 92 | 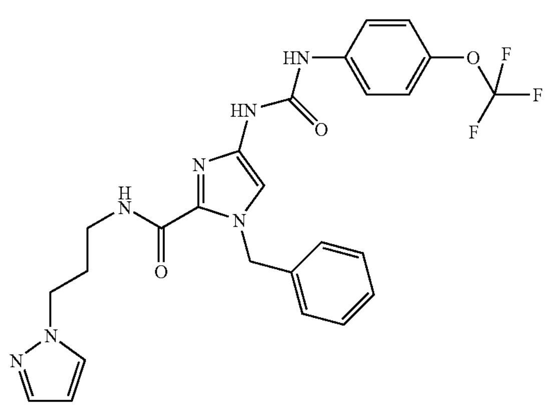 | 527.51 | 528 | 2.60 (1) | Example 11A | 3 | 10 (19) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 93 | 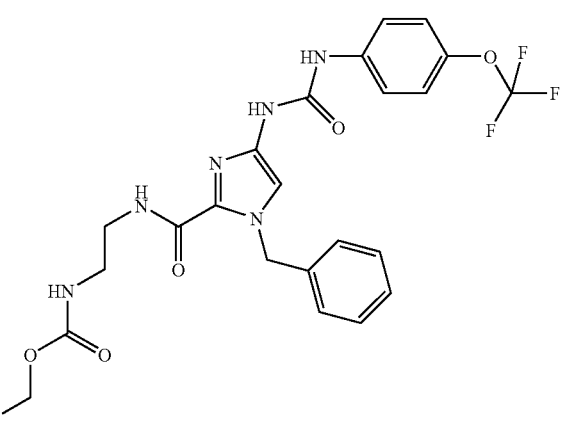 | 534.49 | 535 | 2.57 (1) | Example 11A | 3 | 15 (28) |
| 94 | 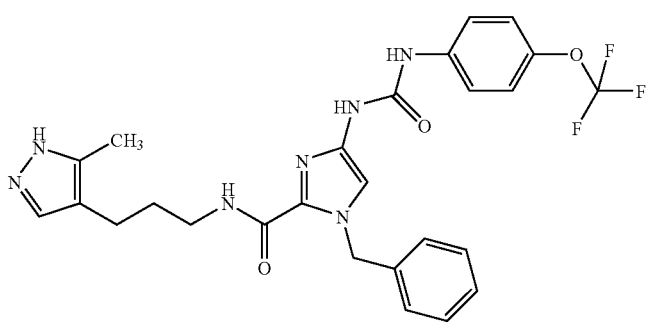 | 541.53 | 542 | 2.46 (1) | Example 11A | 3 | 23 (42) |
| 95 | 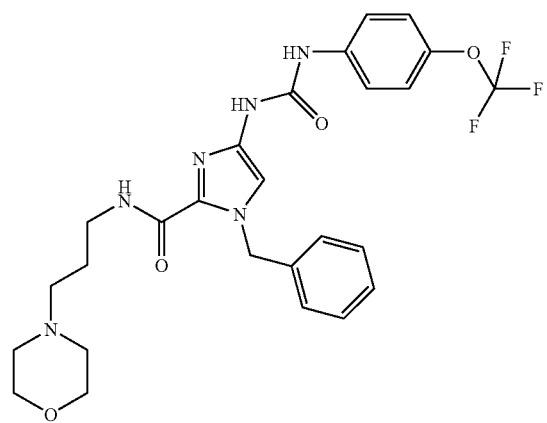 | 546.55 | 547 | 1.94 (1) | Example 11A | 3 | 14 (26) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 96 | 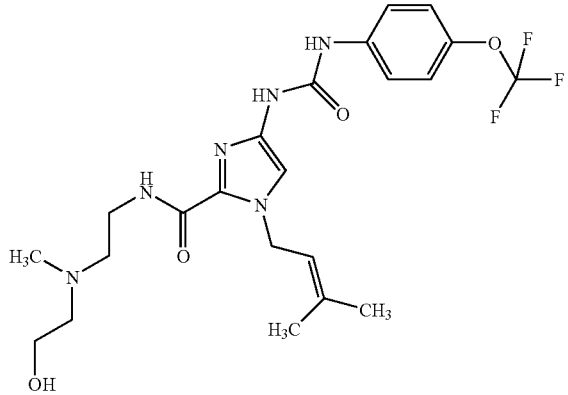 | 498.50 | 499 | 1.90 (1) | Example 13A | 3 | 19 (38) |
| 97 | 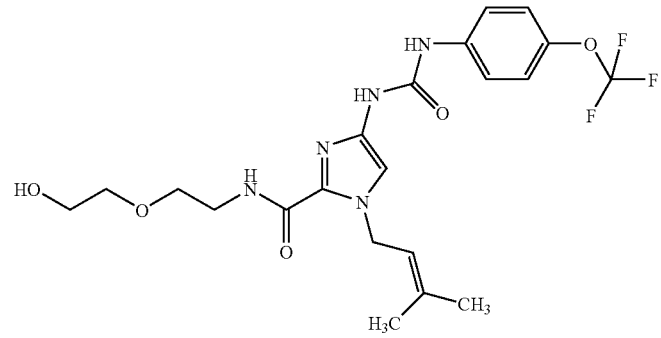 | 485.46 | 486 | 2.39 (1) | Example 13A | 3 | 14 (29) |
| 98 | 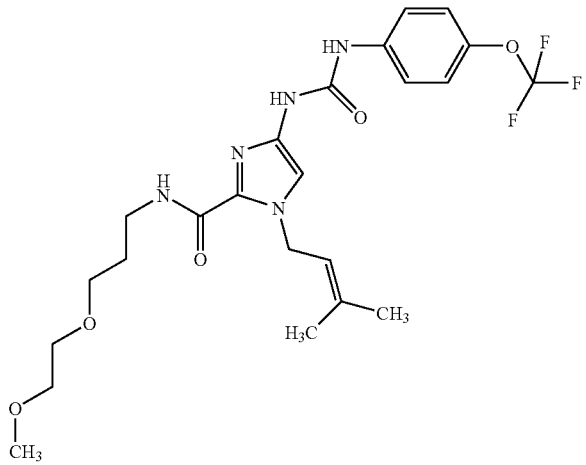 | 513.51 | 514 | 2.64 (1) | Example 13A | 3 | 31 (60) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 99 | 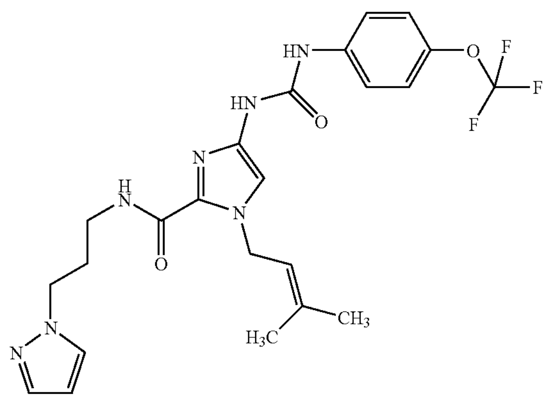 | 505.50 | 506 | 2.64 (1) | Example 13A | 3 | 27 (53) |
| 100 | 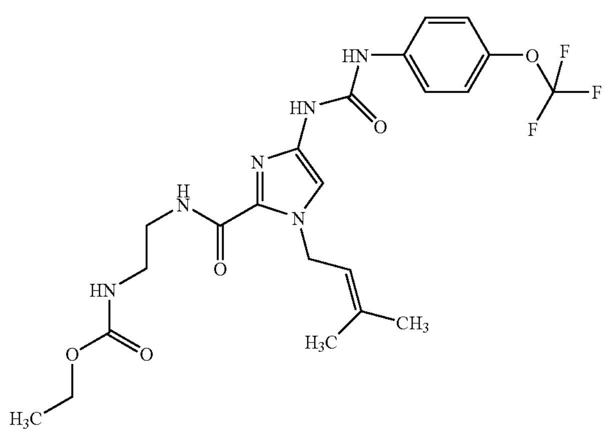 | 512.49 | 513 | 2.60 (1) | Example 13A | 3 | 10 (20) |
| 101 | 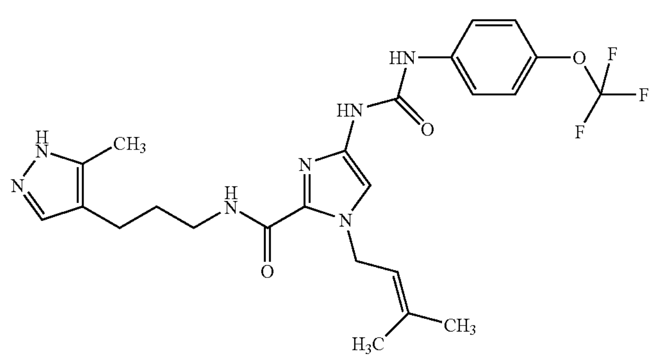 | 519.53 | 520 | 2.49 (1) | Example 13A | 3 | 14 (27) |

-continued
| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 102 | 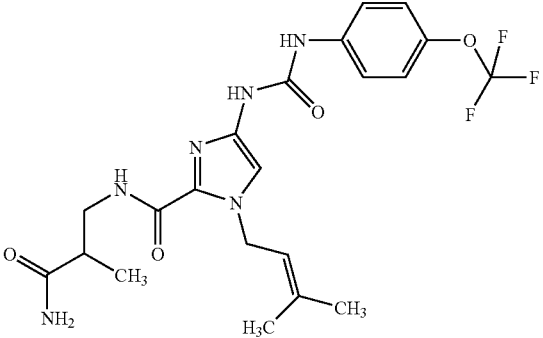 | 482.46 | 483 | 2.37 (1) | Example 13A | 3 | 5 (10) |
| 103 | 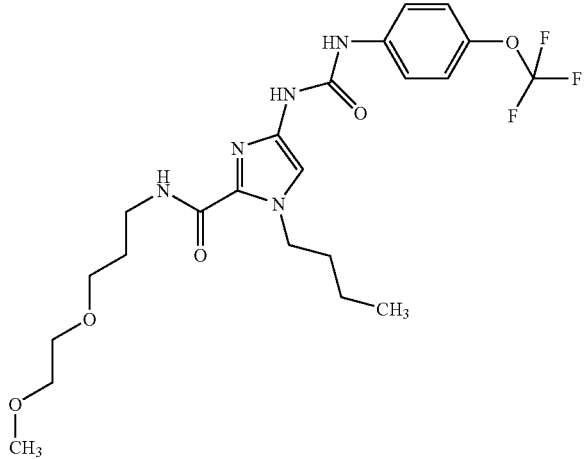 | 501.50 | 502 | 2.59 (1) | Example 7A | 3 | 32 (64) |
| 104 | 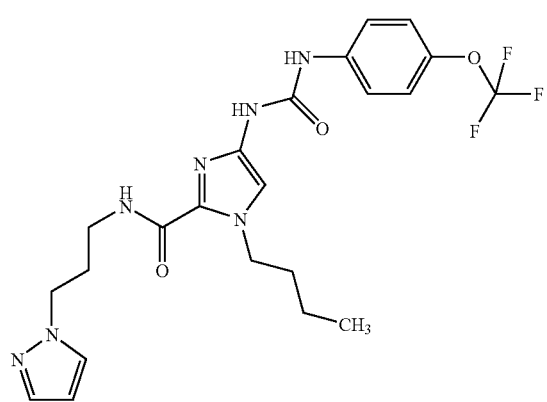 | 493.49 | 494 | 2.59 (1) | Example 7A | 3 | 27 (55) |

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 105 | 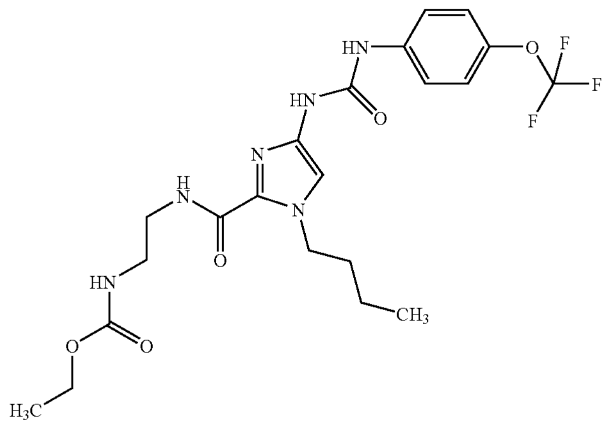 | 500.48 | 501 | 2.55 (1) | Example 7A | 3 | 15 (30) |
| 106 | 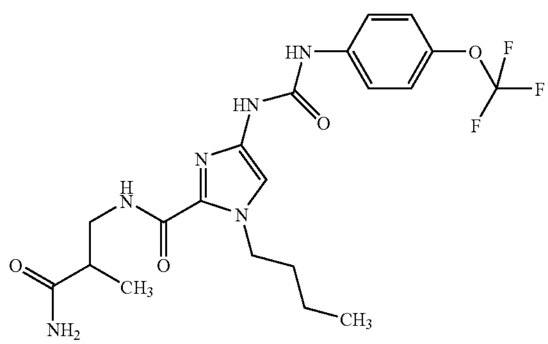 | 470.45 | 471 | 2.32 (1) | Example 7A | 3 | 19 (40) |
| 107 | 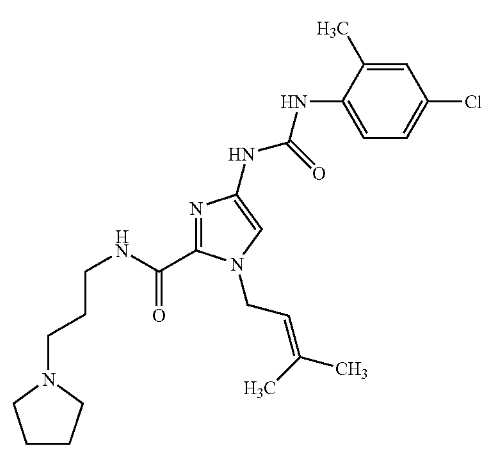 | 473.02 | 473 | 2.00 (5) | Example 12A | 3 | 10 (21) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 108 | 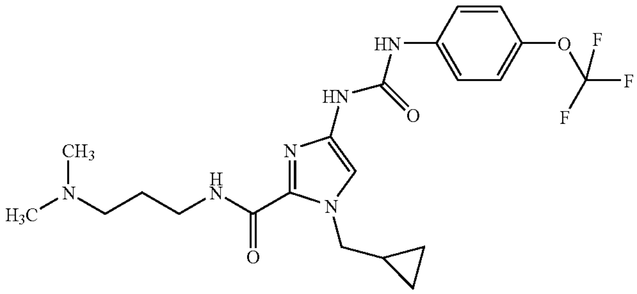 | 468.48 | 469 | 1.95 (5) | Example 5A | 3 | 4.1 (9) |
| 109 | 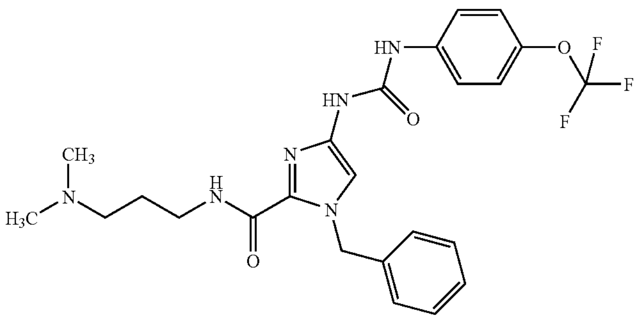 | 504.51 | 505 | 2.03 (5) | Example 11A | 3 | 16 (32) |
| 110 | 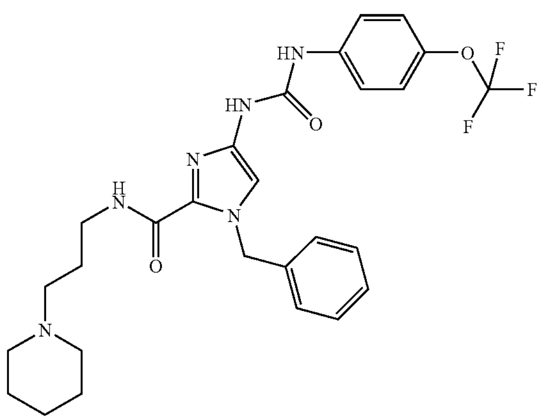 | 544.58 | 545 | 2.09 (5) | Example 11A | 3 | 17 (31) |
| 111 | 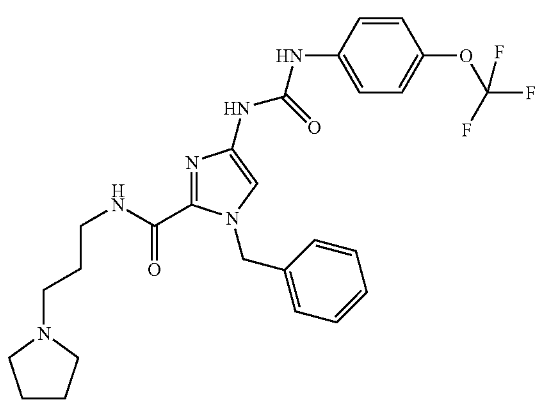 | 530.55 | 531 | 2.11 (5) | Example 11A | 3 | 8 (15) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 112 | 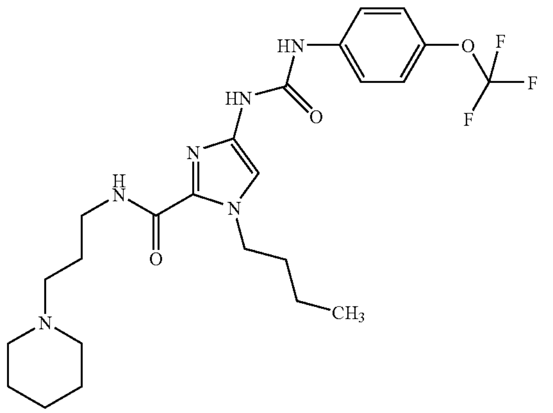 | 510.56 | 511 | 2.05 (5) | Example 7A | 3 | 18 (35) |
| 113 | 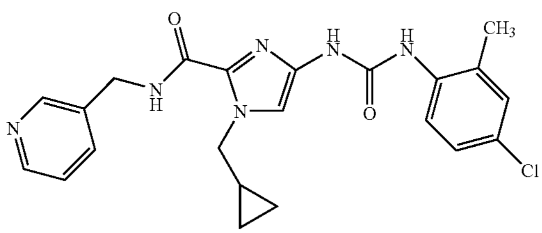 | 438.92 | 439 | 1.97 (5) | Example 4A | 3 | 17.1 (85) |
| 114 | 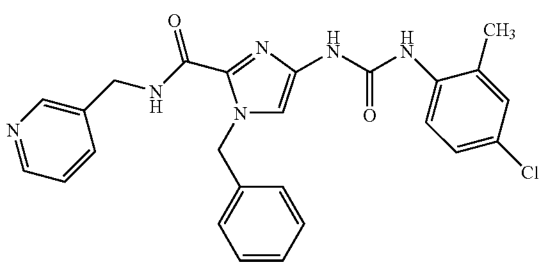 | 474.95 | 475 | 2.09 (1) | Example 10A | 3 | 19.5 (41) |
| 115 | 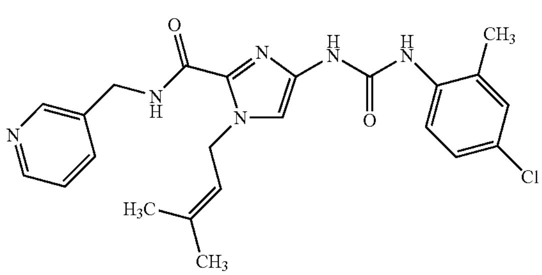 | 452.94 | 453 | 2.15 (5) | Example 12A | 3 | 23.6 (52) |
| 116 | 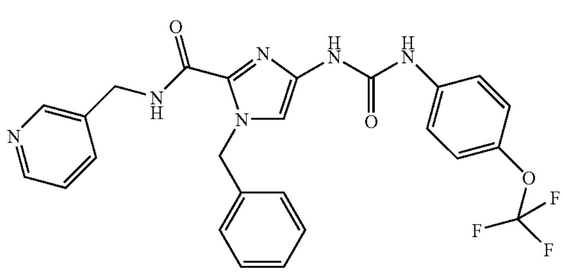 | 510.47 | 511 | 2.02 (4) | Example 11A | 3 | 32.1 (63) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 117 | 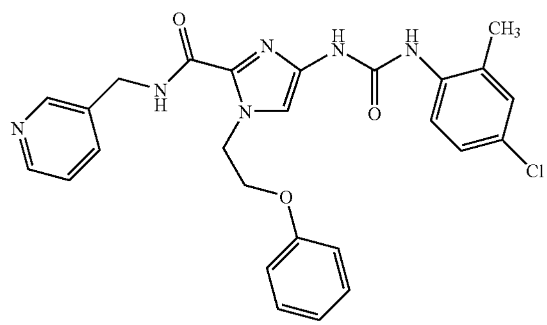 | 504.98 | 505 | 2.18 (5) | Example 14A | 3 | 24 (48) |
| 118 | 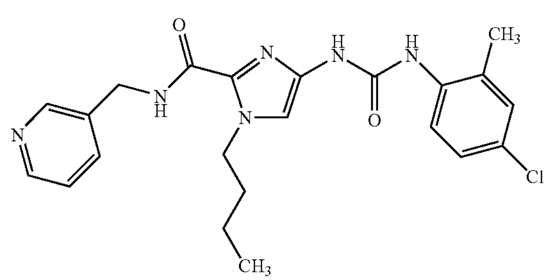 | 440.93 | 441 | 1.87 (4) | Example 6A | 3 | 26.5 (60) |
| 119 | 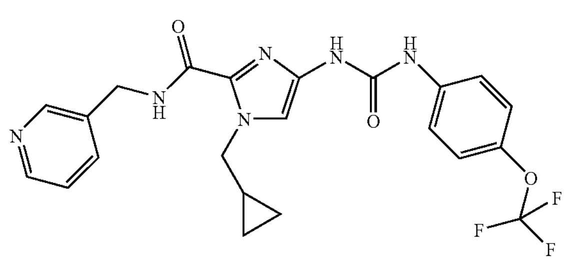 | 474.44 | 475 | 2.03 (2) | Example 5A | 3 | 11 (20) |

-continued

| Example No. | Structure | Mol. mass | MS (EI) [M + H]+ | LC-MS retention time [min] (method) | Starting compound | Preparation in analogy to Example No. | Yield [mg] % of theory |
|---|---|---|---|---|---|---|---|
| 120 | 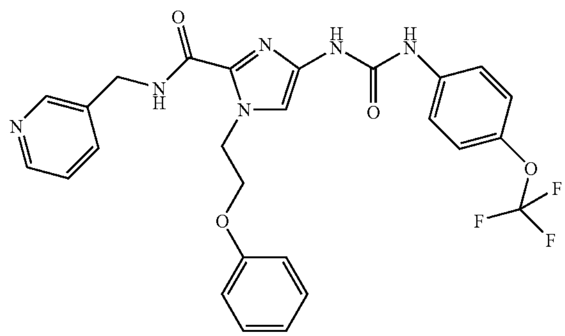 | 540.50 | 541 | 2.28 (5) | Example 15A | 3 | 4.2 (8) |
| 121 | 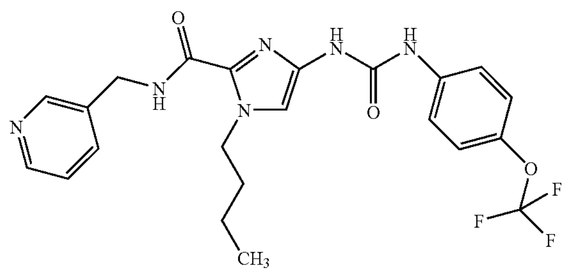 | 476.46 | 477 | 2.15 (5) | Example 7A | 3 | 10.3 (22) |

Example 122

Ethyl 4-[({[4-(trifluoromethoxy)phenyl]amino}carbonyl)amino]-1-[4-(trifluoromethyl)benzyl]-1H-imidazole-2-carboxylate

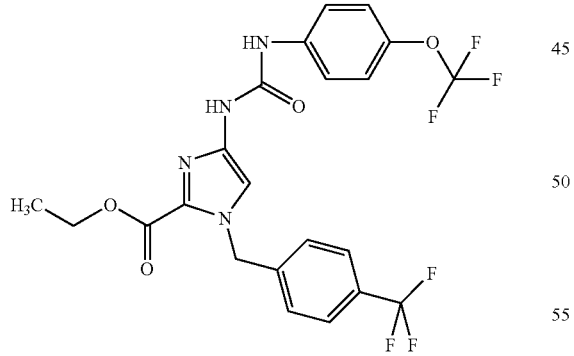

Preparation analogous to Example 4A Stage 3.
Yield: 19.8 mg (38% of theory)
LC-MS (Method 2): $R_t$=2.89 min.
MS (ESI+): m/z=517 [M+H]+
$^1$H-NMR (300 MHz, DMSO-$d_6$): δ=9.1 (s, 1H), 8.95 (s, 1H), 7.75 (d, 2H), 7.55 (d, 2H), 7.5 (s, 1H), 7.4 (d, 2H), 7.25 (d, 2H), 5.7 (s, 2H), 4.25 (q, 2H), 1.35 (tr, 3H) ppm.

Example 123

4-({[(4-Chloro-2-methylphenyl)amino]carbonyl}amino)-N-(2-hydroxyethyl)-1-[4-(trifluoromethyl)benzyl]-1H-imidazole-2-carboxamide

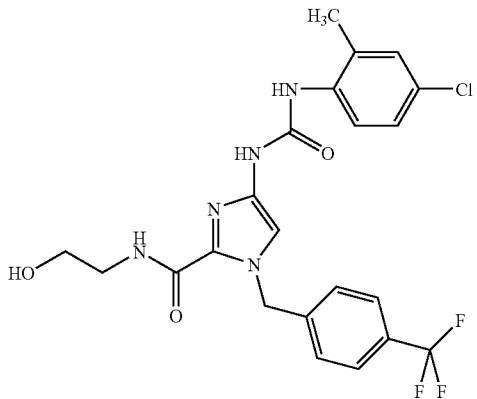

1.81 g (4 mmol) of 4-({[(4-chloro-2-methylphenyl)amino]carbonyl}amino)-1-[4-(trifluoromethyl)benzyl]-1H-imidazole-2-carboxylic acid (Example 20A) are dissolved in 16 ml of absolute DMF, and 1.94 g (12 mmol) of N,N-carbonyldiimidazole are added. The reaction mixture is stirred at RT for 1.5 h and, after addition of 144 µl of water, stirred at RT for 10 min. Then 366 mg (6 mmol) of 2-aminoethanol are added, and the mixture is stirred at RT for 1 h. The reaction mixture is mixed with saturated sodium chloride solution and extracted twice with ethyl acetate. The combined extracts are washed once each with 10% strength citric acid, saturated sodium bicarbonate solution, water and saturated sodium chloride solution, dried with magnesium sulphate and concentrated in vacuo. The residue from evaporation is purified by chromatography on silica gel with dichloromethane/methanol as eluent.

Yield: 0.9 g (45.8% of theory)

LC-MS (Method 2): $R_t$=2.48 min.

MS (ESI$^+$): m/z=496 [M+H]$^+$ $^1$H-NMR (300 MHz, DMSO-d$_6$): δ=9.25 (s, 1H), 8.3 (s broad, 1H), 8.0 (tr, 1H), 7.9 (d, 1H), 7.7 (d, 2H), 7.45 (d, 2H), 7.3 (s, 1H), 7.25 (d, 1H), 7.15 (dd, 1H), 5.75 (s, 2H), 4.75 (tr, 1H), 3.5 (q, 2H), 3.3 (q, 2H), 2.25 (s, 3H) ppm.

Example 124

N-(2-Hydroxyethyl)-4-[({[4-(trifluoromethoxy)phenyl]amino}carbonyl)amino]-1-[4-(trifluoromethyl)benzyl]-1H-imidazole-2-carboxamide

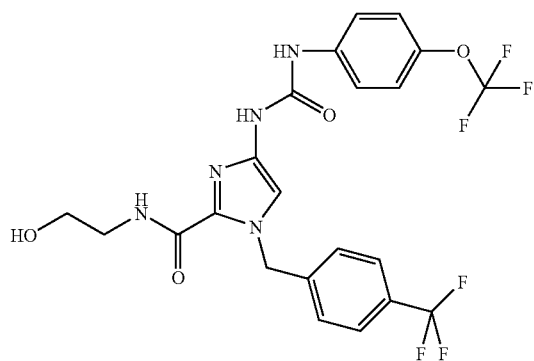

Preparation takes place in analogy to Example 123 from 4-[({[4-(trifluoromethoxy)phenyl]amino}carbonyl)amino]-1-[4-(trifluoromethyl)benzyl]-1H-imidazole-2-carboxylic acid (Example 19A); the residue from evaporation was purified by recrystallization from dichloromethane.

Yield: 1.66 g (78% of theory)

LC-MS (Method 2): $R_t$=2.57 min.

MS (ESI$^+$): m/z=532 [M+H]$^+$ $^1$H-NMR (300 MHz, DMSO-d$_6$): δ=9.05 (s, 1H), 8.8 (s, 1H), 8.05 (tr, 1H), 7.7 (d, 2H), 7.55 (d, 2H), 7.45 (s, 2H), 7.35 (d, 1H), 7.25 (d, 2H), 5.75 (s, 2H), 4.75 (tr, 1H), 3.5 (q, 2H), 3.3 (q, 2H) ppm.

Example 125

2-Hydroxyethyl 4-({[(4-chloro-2-methylphenyl)amino]carbonyl}amino)-1-[4-(trifluoromethyl)benzyl]-1H-imidazole-2-carboxylate

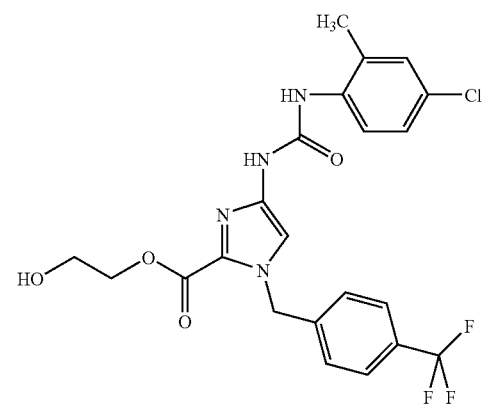

1.36 g (3 mmol) of 4-({[(4-chloro-2-methylphenyl)amino]carbonyl}amino)-1-[4-(trifluoromethyl)benzyl]-1H-imidazole-2-carboxylic acid (Example 20A) are dissolved in 6 ml of absolute DMF, and 0.58 g (3.6 mmol) of N,N-carbonyldiimidazole is added. The reaction mixture is stirred at RT for 3 h. Then 18.4 g (16.5 ml, 297 mmol) of 1,2-ethanediol and 303 mg (418 µl, 3 mmol) of triethylamine are added. The reaction mixture is stirred at 50° C. for 1.5 h and at RT overnight. Dilution with water is followed by extraction twice with ethyl acetate. The combined extracts are washed twice with saturated sodium bicarbonate solution, once with water and twice with saturated sodium chloride solution, dried over magnesium sulphate and concentrated in vacuo. The residue from evaporation is purified by chromatography on silica gel with cyclohexane/ethyl acetate as eluent.

Yield: 0.95 g (64% of theory)

LC-MS (Method 2): $R_t$=2.60 min.

MS (ESI$^+$): m/z=497 [M+H]$^+$ $^1$H-NMR (300 MHz, DMSO-d$_6$): δ=9.5 (s, 1H), 8.6 (s broad, 1H), 7.95 (d, 1H), 7.7 (d, 2H), 7.4 (d, 2H), 7.4 (s, 1H), 7.25 (d, 1H), 7.15 (dd, 1H), 5.7 (s, 2H), 4.85 (tr, 1H), 4.25 (tr, 2H), 3.65 (q, 2H), 2.3 (s, 3H) ppm.

Example 126

2-Hydroxyethyl 4-[({[4-(trifluoromethoxy)phenyl]amino}carbonyl)amino]-1-[4-(trifluoromethyl)benzyl]-1H-imidazole-2-carboxylate

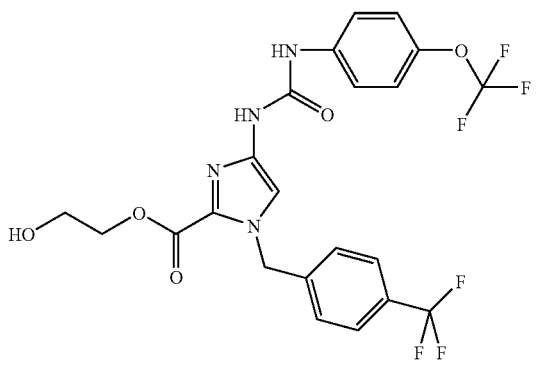

Preparation takes place in analogy to Example 125 from 4-[({[4-(trifluoromethoxy)phenyl]amino}carbonyl)amino]-1-[4-(trifluoromethyl)benzyl]-1H-imidazole-2-carboxylic acid (Example 19A); the residue from evaporation is purified by chromatography on silica gel with dichloromethane/methanol as eluent. Yield: 760 mg (48% of theory)

LC-MS (Method 4): $R_f$=2.64 min.
MS (ESI$^+$): m/z=533 [M+H]$^+$
$^1$H-NMR (300 MHz, DMSO-d$_6$): δ=9.05 (s, 1H), 8.95 (s, 1H), 7.75 (d, 2H), 7.55 (d, 2H), 7.5 (s, 1H), 7.4 (s, 2H), 7.25 (d, 2H), 5.7 (s, 2H), 4.85 (tr, 1H), 4.2 (tr, 2H), 3.5 (q, 2H) ppm.

Example 127

4-({[(4-Chloro-2-methylphenyl)amino]carbonyl}amino)-N-[2-(dimethylamino)ethyl]-1-[4-(trifluoromethyl)benzyl]-1H-imidazole-2-carboxamide

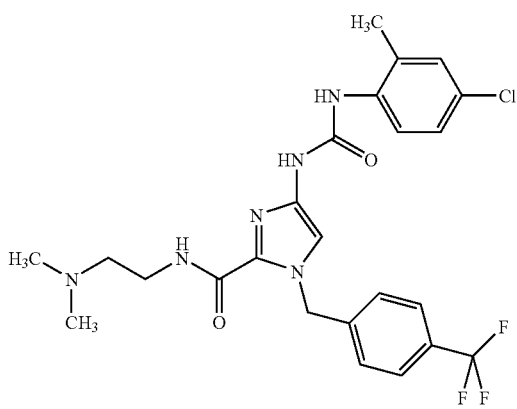

25.7 mg (0.05 mmol) of N-(2-chloroethyl)-4-({[(4-chloro-2-methylphenyl)amino]carbonyl}amino)-1-[4-(trifluoromethyl)benzyl]-1H-imidazole-2-carboxamide (Example 21A) are dissolved in 200 μl of a 2 molar solution of dimethylamine in THF, and 7.5 mg (0.05 mmol) of sodium iodide are added. The reaction mixture is stirred in a tightly closed reaction vessel at 55° C. for 16 h. The reaction solution is then evaporated in vacuo, and the residue from evaporation is dissolved in DMSO, filtered and purified by preparative HPLC (Method 10).

Yield: 10.4 mg (40% of theory)
LC-MS (Method 4): $R_f$=1.90 min.
MS (ESI$^+$): m/z=523 [M+H]$^+$
$^1$H-NMR (300 MHz, DMSO-d$_6$): δ=9.4 (s, 1H), 8.2 (s broad, 1H), 7.9 (s broad, 1H), 7.9 (d, 1H), 7.7 (d, 2H), 7.45 (d, 2H), 7.3 (s, 1H), 7.25 (s, 1H), 7.15 (d, 1H), 5.75 (s, 2H), 2.4 (tr, 2H), 2.25 (s, 3H), 2.2 (s, 6H) ppm.

Example 128

4-({[(4-Chloro-2-methylphenyl)amino]carbonyl}amino)-N-[2-(cyclopropylamino)ethyl]-1-[4-(trifluoromethyl)benzyl]-1H-imidazole-2-carboxamide

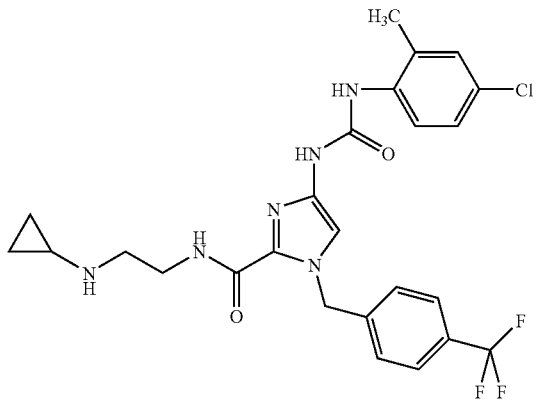

51.4 mg (0.1 mmol) of N-(2-chloroethyl)-4-({[(4-chloro-2-methylphenyl)amino]carbonyl}-amino)-1-[4-(trifluoromethyl)benzyl]-1H-imidazole-2-carboxamide (Example 21A) are dissolved together with 57.1 mg of cyclopropylamine in 0.4 ml of dimethoxyethane, and 15 mg (0.1 mmol) of sodium iodide are added. The reaction mixture is heated under reflux for 16 h. After cooling DMSO is added, and the solution is filtered and purified by preparative HPLC (Method 10).

Yield: 8.5 mg (16% of theory)
LC-MS (Method 4): $R_f$=1.92 min.
MS (ESI$^+$): m/z=535 [M+H]$^+$
$^1$H-NMR (300 MHz, DMSO-d$_6$): δ=9.3 (s, 1H), 8.35 (s broad, 1H), 8.05 (tr, 1H), 7.9 (d, 1H), 7.75 (d, 2H), 7.45 (d, 2H), 7.3 (s, 1H), 7.25 (s, 1H), 7.15 (d, 1H), 5.75 (s, 2H), 2.7 (tr, 2H), 2.25 (s, 3H), 2.05 (m, 1H), 0.35 (m, 2H), 0.2 (m, 2H) ppm.

Examples 129 to 132 listed in Table 2 are prepared from the compound from Example 22A in analogy to Example 128.

TABLE 2

| Ex. No. | Structure | Mol. mass | MS (EI) [M + H]+ | LC-MS R_t [min] (method) | Yield [mg] (% of theory) |
|---|---|---|---|---|---|
| 129 | 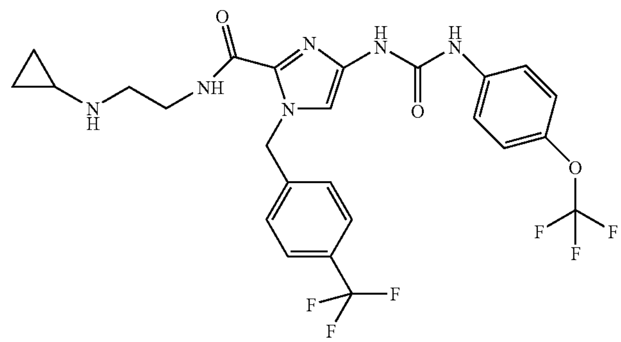 | 570.49 | 571 | 2.24 (2) | 10 (18) |
| 130 | 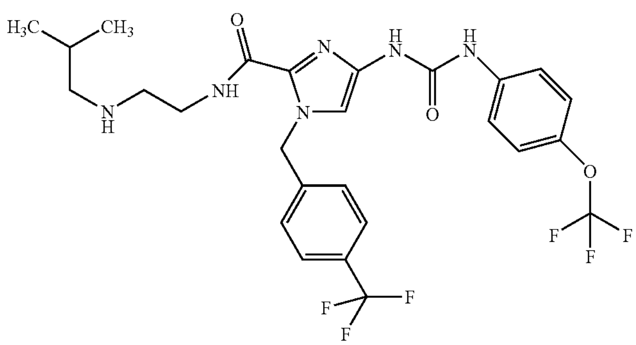 | 586.53 | 587 | 2.32 (2) | 26 (44) |
| 131 | 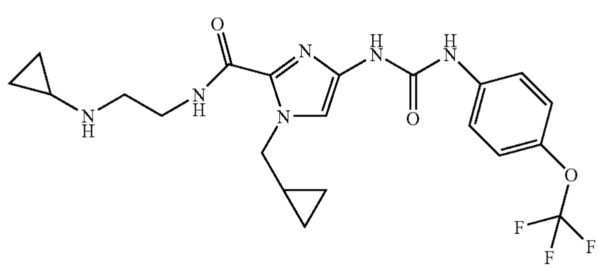 | 466.46 | 467 | 1.97 (2) | 4.2 (9) |
| 132 | 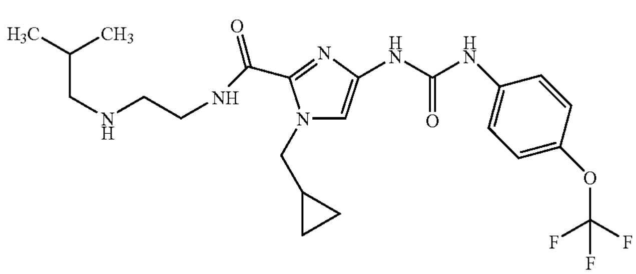 | 482.50 | 483 | 2.06 (2) | 15 (31) |

Example 133

2-[({4-({[(4-Chloro-2-methylphenyl)amino]carbonyl}amino)-1-[4-(trifluoromethyl)benzyl]-1H-imidazol-2-yl}carbonyl)amino]ethyl N,N-dimethylglycinate

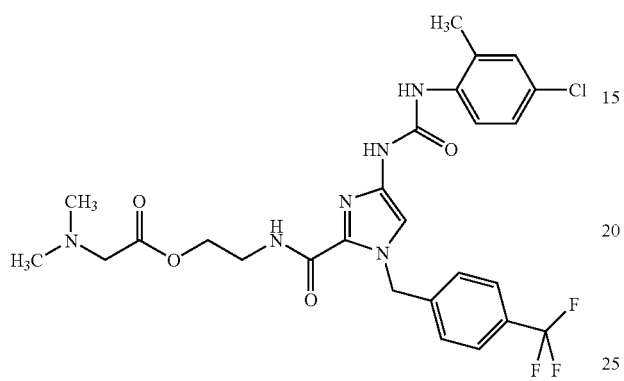

114.5 mg (0.2 mmol) of 2-[({4-({[(4-chloro-2-methylphenyl)amino]carbonyl}amino)-1-[4-(trifluoromethyl)benzyl]-1H-imidazol-2-yl}carbonyl)amino]ethyl chloroacetate (Example 26A) are dissolved in 2 ml of a 2 molar solution of dimethylamine in THF. The reaction mixture is shaken in a tightly closed reaction vessel at RT for 16 h and then left to stand at RT for 64 h. The reaction solution is then evaporated, and the residue from the evaporation is dissolved in DMF, filtered and purified by preparative HPLC (Method 9).

Yield: 16 mg (14% of theory)

LC-MS (Method 2): $R_f$=2.18 min.

MS (ESI$^+$): m/z=581 [M+H]$^+$ $^1$H-NMR (300 MHz, DMSO-d$_6$): δ=9.2 (s, 1H), 8.4 (s broad, 1H), 8.25 (tr, 1H), 7.9 (d, 1H), 7.7 (d, 2H), 7.4 (d, 2H), 7.3 (s, 1H), 7.25 (s, 1H), 7.15 (d, 1H), 5.75 (s, 2H), 4.15 (tr, 2H), 3.5 (q, 2H), 3.15 (s, 2H), 2.25 (s, 9H) ppm.

Example 134

2-[({4-[({[4-(Trifluoromethoxy)phenyl]amino}carbonyl)amino]-1-[4-(trifluoromethyl)benzyl]-1H-imidazol-2-yl}carbonyl)amino]ethyl N,N-dimethylglycinate

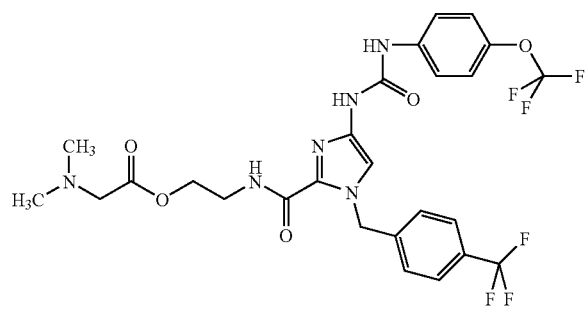

Preparation takes place in analogy to Example 133 from 2-[({4-[({[2-methyl-4-(trifluoromethoxy)phenyl]amino}carbonyl)amino]-1-[4-(trifluoromethyl)benzyl]-1H-imidazol-2-yl}carbonyl)amino]ethyl chloroacetate (Example 25A). Yield: 14 mg (11% of theory)

LC-MS (Method 2): $R_f$=2.27 min.

MS (ESI$^+$): m/z=617 [M+H]$^+$ $^1$H-NMR (300 MHz, DMSO-d$_6$): δ=9.1 (s, 1H), 8.7 (s, 1H), 8.3 (tr, 1H), 7.7 (d, 2H), 7.55 (d, 2H), 7.4 (d, 2H), 7.35 (s, 1H), 7.25 (s, 2H), 5.75 (s, 2H), 4.15 (tr, 2H), 3.5 (q, 2H), 3.15 (s, 2H), 2.25 (s, 9H) ppm.

Example 135

2-[({4-({[(4-Chloro-2-methylphenyl)amino]carbonyl}amino)-1-[4-(trifluoromethyl)benzyl]-1H-imidazol-2-yl}carbonyl)amino]ethyl N,N-diethylglycinate

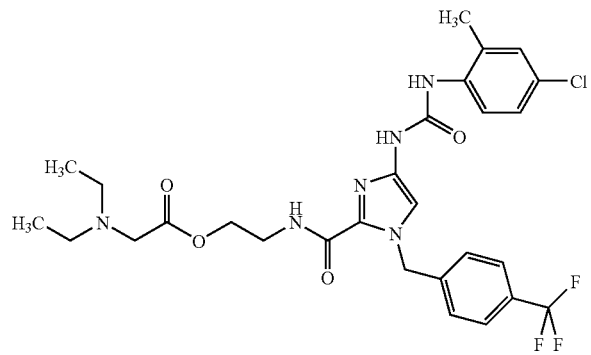

123.4 mg (0.2 mmol) of 2-[({4-({[(4-chloro-2-methylphenyl)amino]carbonyl}amino)-1-[4-(trifluoromethyl)benzyl]-1H-imidazol-2-yl}carbonyl)amino]ethyl chloroacetate (Example 26A) are dissolved in 0.8 ml of absolute DMF under argon, and 29.3 (0.4 mmol) of diethylamine are added. The reaction mixture is stirred at RT for 2.5 h, filtered and purified by preparative HPLC (Method 9).

Yield: 34.1 mg (28% of theory)

LC-MS (Method 4): $R_f$=2.29 min.

MS (ESI$^+$): m/z=496 [M+H]$^+$ $^1$H-NMR (300 MHz, DMSO-d$_6$): δ=9.25 (s, 1H), 8.3 (s broad, 1H), 8.15 (s, 1H), 7.9 (d, 1H), 7.7 (d, 2H), 7.4 (d, 2H), 7.3 (s, 1H), 7.25 (d, 1H), 7.15 (dd, 1H), 5.75 (s, 2H), 4.15 (tr, 2H), 3.5 (q, 2H), 2.5 (q, 4H), 2.25 (s, 3H), 0.9 (tr, 6H) ppm.

Examples 136 to 140 listed in Table 3 are prepared from the compound from Example 25A in analogy to Example 135.

TABLE 3

| Ex. No. | Structure | Mol. mass | MS (EI) [M + H]+ | LC-MS R_t [min] (method) | Yield [mg] (% of theory) |
|---|---|---|---|---|---|
| 136 | 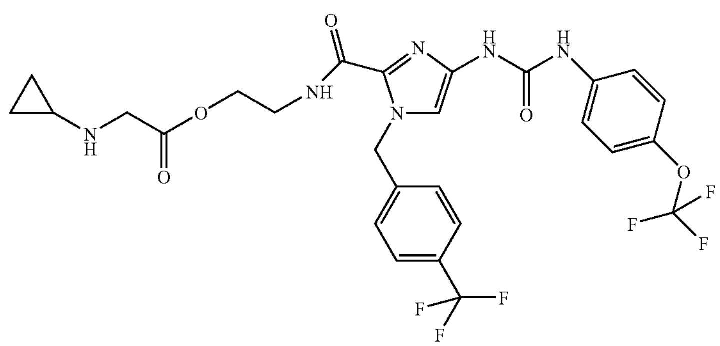 | 628.52 | 629 | 2.22 (2) | 40 (32) |
| 137 | 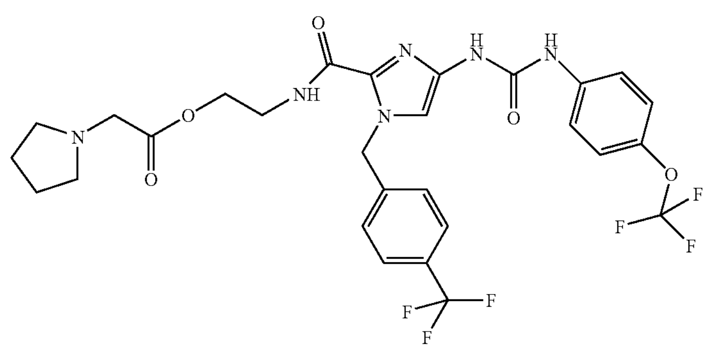 | 642.55 | 643 | 2.3 (2) | 46 (36) |
| 138 | 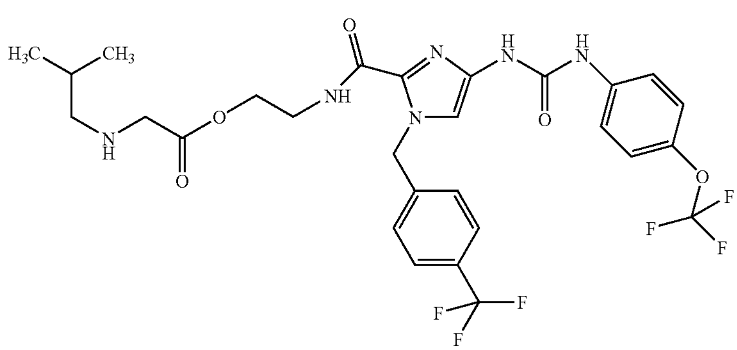 | 644.57 | 645 | 2.38 (2) | 42 (33) |
| 139 | 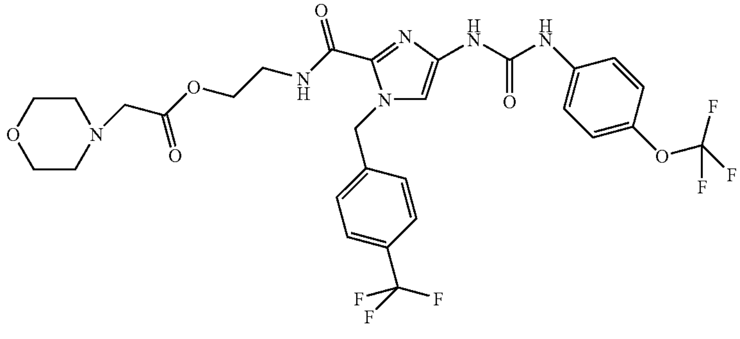 | 658.55 | 659 | 2.35 (2) | 15.2 (30) |

TABLE 3-continued

| Ex. No. | Structure | Mol. mass | MS (EI) [M + H]+ | LC-MS R_t [min] (method) | Yield [mg] (% of theory) |
|---|---|---|---|---|---|
| 140 | 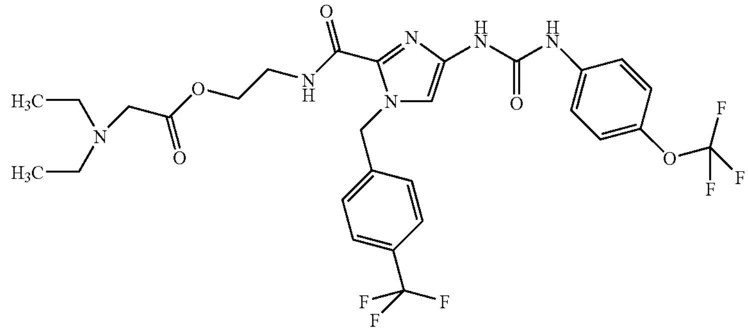 | 644.57 | 645 | 2.34 (2) | 26.6 (21) |

Example 141

2-[(2-Morpholin-4-ylacetyl)oxy]ethyl 4-({[(4-chloro-2-methylphenyl)amino]carbonyl}-amino)-1-[4-(trifluoromethyl)benzyl]-1H-imidazole-2-carboxylate

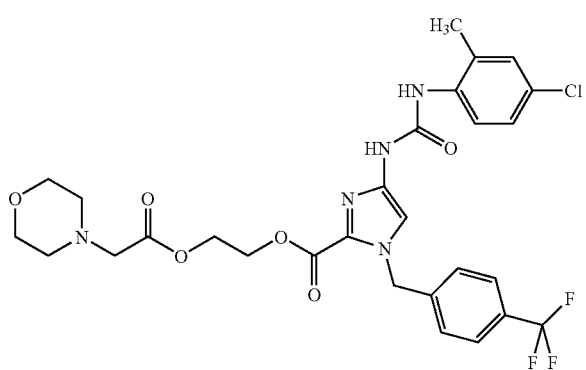

61.8 mg (0.1 mmol) of 2-[(2-bromoacetyl)oxy]ethyl 4-({[(4-chloro-2-methylphenyl)amino]carbonyl}amino)-1-[4-(trifluoromethyl)benzyl]-1H-imidazole-2-carboxylate (Example 24A) are dissolved in 0.4 ml of 1,2-dimethoxyethane under argon, and 15 mg (0.1 mmol) of sodium iodide and 43.6 mg (0.5 mmol) of morpholine are added. The reaction mixture is heated under reflux for 2 h and then mixed with 0.3 ml of DMSO, filtered and purified by preparative HPLC (Method 9).

Yield: 14.5 mg (23% of theory)

LC-MS (Method 2): R_t=2.38 min.

MS (ESI+): m/z=624 [M+H]+

$^1$H-NMR (300 MHz, DMSO-d$_6$): δ=9.55 (s, 1H), 8.6 (s broad, 1H), 7.95 (d, 1H), 7.7 (d, 2H), 7.45 (s, 1H), 7.4 (d, 2H), 7.25 (d, 1H), 7.15 (dd, 1H), 5.7 (s, 2H), 4.45 (m, 2H), 4.3 (m, 2H), 3.5 (tr, 4H), 3.2 (s, 2H), 2.45 (tr, 4H), 2.25 (s, 3H) ppm.

Examples 142 to 145 listed in Table 4 are prepared in analogy to Example 141.

TABLE 4

| Ex. No. | Structure | Mol. mass | MS (EI) [M + H]+ | LC-MS R_t [min] (method) | Starting compound Yield [mg] (% of theory) |
|---|---|---|---|---|---|
| 142 | 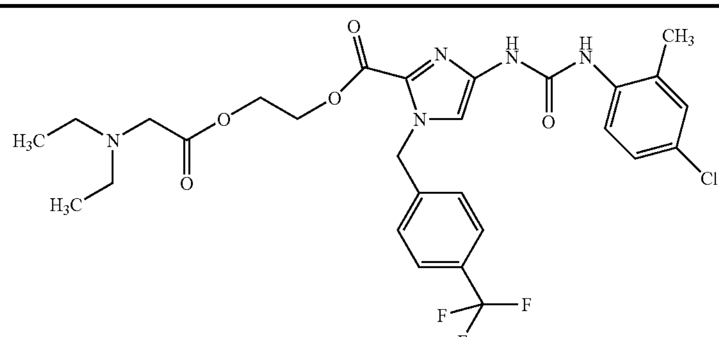 | 610.03 | 611 | 2.27 (2) | Example 24A 31.9 (52) |

TABLE 4-continued

| Ex. No. | Structure | Mol. mass | MS (EI) [M + H]+ | LC-MS R_t [min] (method) | Starting compound Yield [mg] (% of theory) |
|---|---|---|---|---|---|
| 143 | 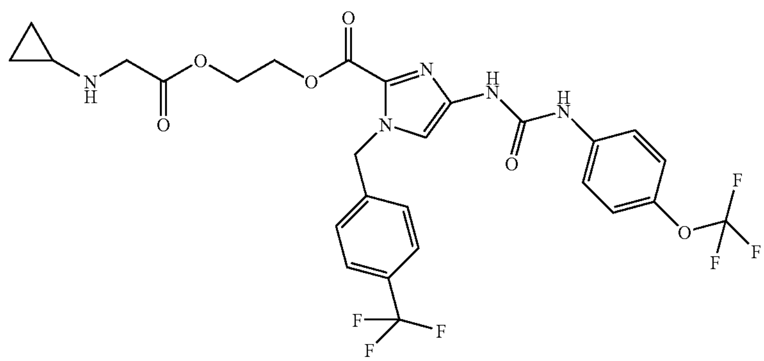 | 629.51 | 630 | 2.35 (2) | Example 27A 5.7 (9) |
| 144 | 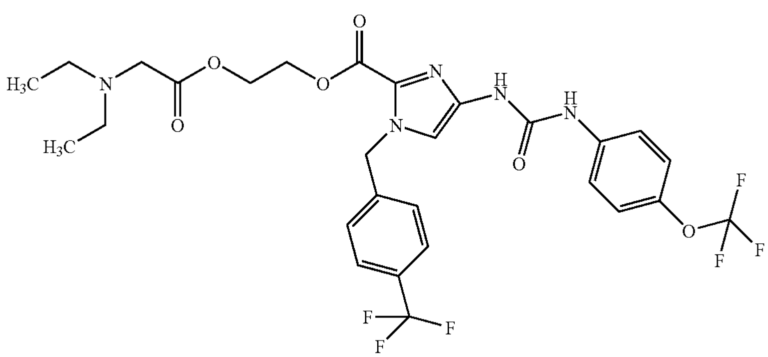 | 645.55 | 646 | 2.35 (2) | Example 27A 31.9 (49) |
| 145 | 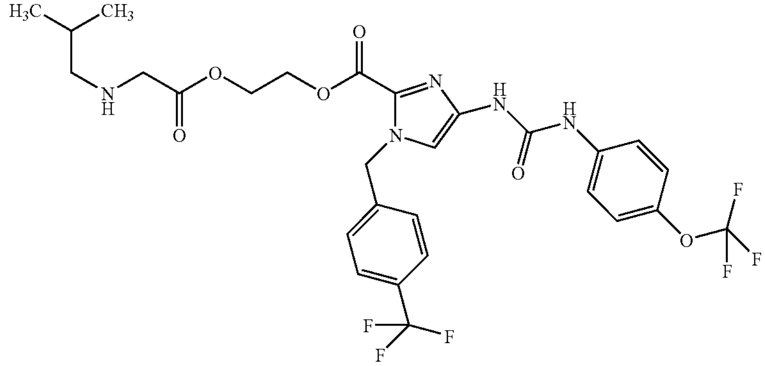 | 645.55 | 646 | 2.43 (2) | Example 27A 5.4 (8) |

Example 146

(4R)-4-Amino-5-{2-[({1-butyl-4-[({[4-(trifluoromethoxy)phenyl]amino}carbonyl)amino]-1H-imidazol-2-yl}carbonyl)amino]ethoxy}-5-oxopentanoic Acid Hydrochloride

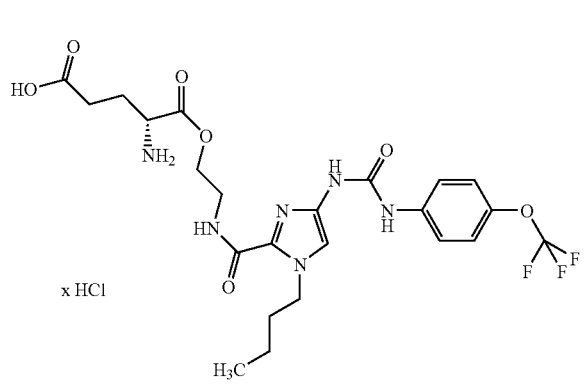

x HCl 91 mg (0.3 mmol) of (2R)-5-tert-butoxy-2-[(tert-butoxycarbonyl)amino]-5-oxopentanoic acid are dissolved in 1 ml of DMF and, after addition of 58 mg (0.3 mmol) of EDCI×HCl and 37 mg (0.30 mmol) of DMAP, stirred at room temperature for 10 minutes. Then 70 mg (0.15 mmol) of 1-butyl-N-(2-hydroxyethyl)-4-[({[4-(trifluoromethoxy)phenyl]amino}-carbonyl)amino]-1H-imidazole-2-carboxamide (Example 81) are added, and the mixture is stirred at room temperature overnight. The reaction mixture is purified by preparative HPLC. The product-containing fractions are evaporated in vacuo.

Yield: 41 mg (46% of theory)
LC-MS (Method 4): $R_t$=1.70 min.
MS (ESI⁺): m/z=559 [M+H]⁺
¹H-NMR (300 MHz, DMSO-d₆): δ=9.86 (s, 1H), 8.84 (s, 1H), 8.46 (d, 2H), 8.35 (t, 1H), 7.58 (d, 2H), 7.26 (m, 3H), 4.20-4.45 (m, 4H), 3.90-4.11 (m, 1H), 3.53 (q, 2H), 2.32-2.55 (m, 2H), 1.91-2.12 (m, 2H), 1.61-1.76 (quintet, 2H), 1.18-1.34 (m, 2H), 0.89 (t, 3H) ppm.

Example 147

(4S)-4-Amino-5-{2-[({1-butyl-4-[({[4-(trifluoromethoxy)phenyl]amino}carbonyl)amino]-1H-imidazol-2-yl}carbonyl)amino]ethoxy}-5-oxopentanoic Acid Hydrochloride

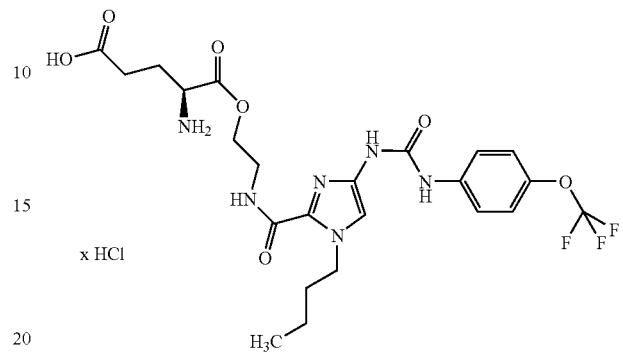

x HCl 91 mg (0.30 mmol) of (2S)-5-tert-butoxy-2-[(tert-butoxycarbonyl)amino]-5-oxopentanoic acid are dissolved in 5 ml of DMF and, after addition of 58 mg (0.3 mmol) of EDCI×HCl and 37 mg (0.30 mmol) of DMAP, stirred at room temperature for 10 minutes. Then 70 mg (0.15 mmol) of 1-butyl-N-(2-hydroxyethyl)-4-[({[4-(trifluoromethoxy)phenyl]amino}-carbonyl)amino]-1H-imidazole-2-carboxamide (Example 81) are added, and the mixture is stirred at room temperature overnight. The reaction mixture is purified by preparative HPLC. The product-containing fractions are evaporated in vacuo.

Yield: 35 mg (39% of theory)
LC-MS (Method 5): $R_t$=1.97 min.
MS (ESI⁺): m/z=559 [M+H]⁺
¹H-NMR (400 MHz, DMSO-d₆): δ=9.76 (s, 1H), 8.81 (s, 1H), 8.46 (d, 2H), 8.35 (t, 1H), 7.57 (d, 2H), 7.26 (m, 3H), 4.21-4.44 (m, 4H), 3.99-4.11 (m, 1H), 3.53 (m, 2H), 2.32-2.55 (m, 2H), 1.91-2.13 (m, 2H), 1.61-1.76 (quintet, 2H), 1.18-1.34 (m, 2H), 0.89 (t, 3H) ppm.

Examples 148 to 150 listed in Table 5 are prepared from the compound from Example 81 in analogy to Example 147.

TABLE 5

| Ex. No. | Structure | Mol. mass | MS (EI) [M+H]⁺ | LC-MS $R_t$ [min] (method) | Yield [mg] (% of theory) |
|---|---|---|---|---|---|
| 148 | (structure shown) | 564.99 | 529 | 1.71 (4) | 69 (73) |

TABLE 5-continued

| Ex. No. | Structure | Mol. mass | MS (EI) [M + H]+ | LC-MS R_t [min] (method) | Yield [mg] (% of theory) |
|---|---|---|---|---|---|
| 149 | 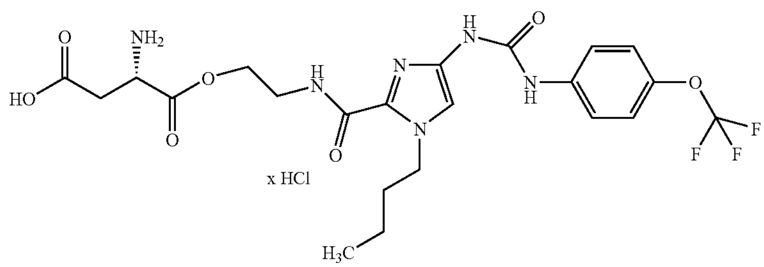 | 580.95 | 545 | 1.72 (4) | 34 (39) |
| 150 | 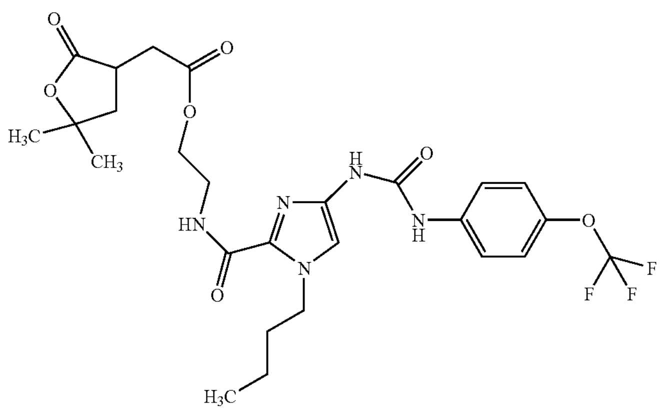 | 583.56 | 584 | 2.54 (4) | 27 (31) |

Example 151

N-(3-Chloropropyl)-1-methyl-4-[({[4-(trifluoromethoxy)phenyl]amino}carbonyl)amino]-1H-imidazol-2-carboxamide

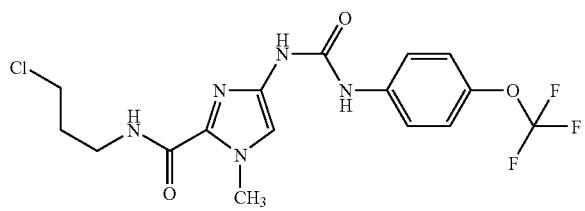

140 mg (0.36 mmol) of 1-methyl-4-[({[4-(trifluoromethoxy)phenyl]amino}carbonyl)amino]-1H-imidazole-2-carboxylic acid (Example 29A) are dissolved in 8 ml of DMF and, after addition of 204 mg (0.54 mmol) of HATU and 66 mg (0.54 mmol) of DMAP, stirred at room temperature for 15 minutes. Then a solution of 93 mg (0.72 mmol) of 3-chloropropan-1-amine hydrochloride and 80 mg (0.79 mmol) of triethylamine in 1 ml of DMF is added dropwise, and the reaction mixture is stirred overnight. The reaction mixture is purified by preparative HPLC. The product-containing fractions are evaporated in vacuo.

Yield: 144 mg (96% of theory)
LC-MS (Method 2): R_t=2.43 min.
MS (ESI+): m/z=420 [M+H]+

Example 152

1-Methyl-N-(4,4,4-trifluorobutyl)-4-[({[4-(trifluoromethoxy)phenyl]amino}carbonyl)amino]-1H-imidazole-2-carboxamide

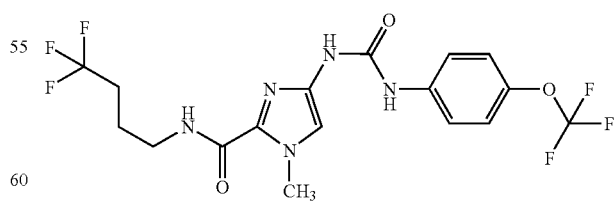

Preparation in analogy to Example 151.
Yield: 80 mg (99% of theory)
LC-MS (Method 2): R_t=2.54 min.
MS (ESI+): m/z=454 [M+H]+

Example 153

1-Butyl-N-(3-chloropropyl)-4-[({[4-(trifluoromethoxy)phenyl]amino}carbonyl)amino]-1H-imidazole-2-carboxamide

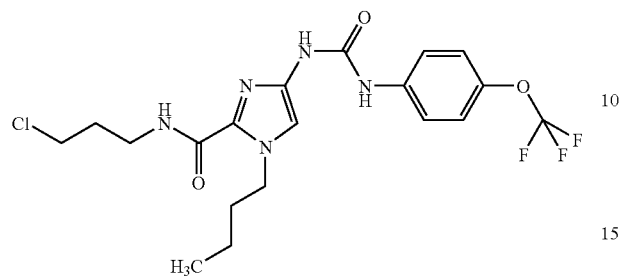

Preparation in analogy to Example 1.
Yield: 115 mg (83% of theory)
LC-MS (Method 5): $R_t$=2.78 min.
MS (ESI$^+$): m/z=462 [M+H]$^+$ Examples 154 to 171 listed in Table 6 are prepared from the compound from Example 7 in analogy to Example 1.

TABLE 6

| Example No. | Structure | Mol. mass | MS (EI) [M + H]$^+$ | LC-MS retention time [min] (method) | Synthesis of the amine starting compound | Yield [mg] (% of theory) |
|---|---|---|---|---|---|---|
| 154 | 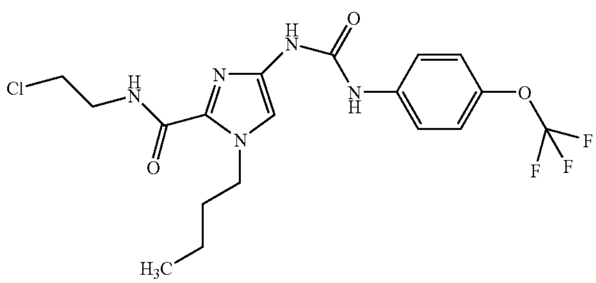 | 447.84 | 448 | 2.72 (5) | | 125 (89) |
| 155 | 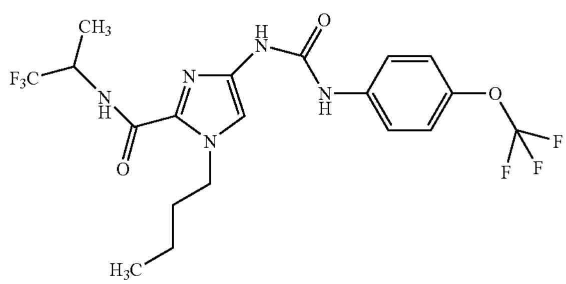 | 481.40 | 482 | 2.73 (4) | method of Soloshonok, Vadim A.; Ono, Taizo; J. Org. Chem.; 62; 10; 1997; 3030-3031 | 68 (93) |
| 156 | 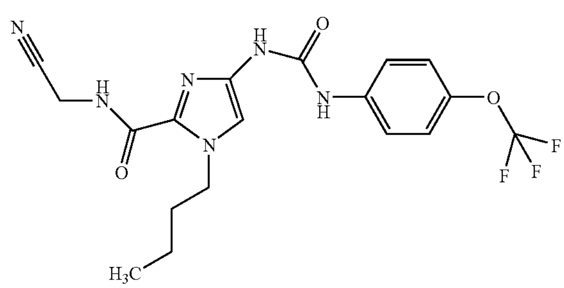 | 424.38 | 425 | 2.38 (4) | | 59 (90) |

TABLE 6-continued

| Example No. | Structure | Mol. mass | MS (EI) [M + H]+ | LC-MS retention time [min] (method) | Synthesis of the amine starting compound | Yield [mg] (% of theory) |
|---|---|---|---|---|---|---|
| 157 | 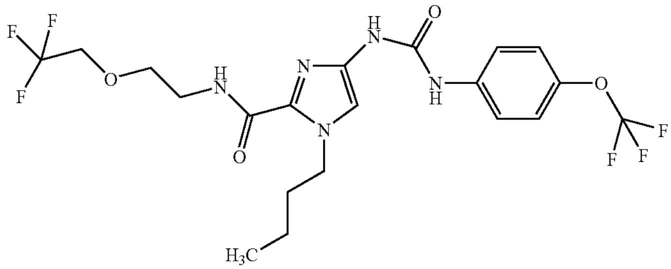 | 511.42 | 512 | 2.63 (4) | | 67 (84) |
| 158 | 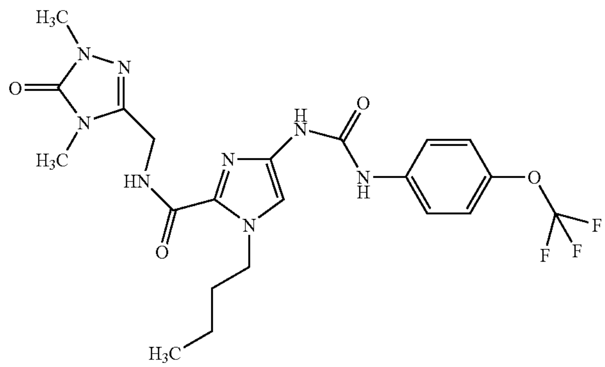 | 510.47 | 511 | 2.13 (4) | method of Gehlen; Blankenstein; Justus Liebigs Ann. Chem.; 651; 1962; 137, 139. | 76 (99) |
| 159 | 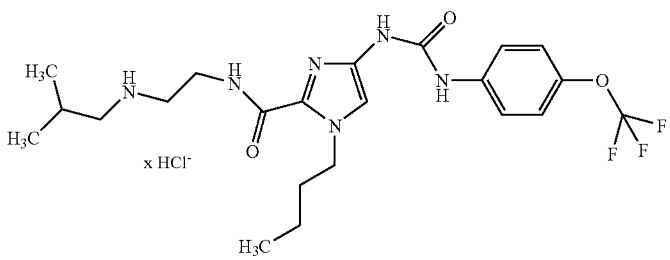 | 520.98 | 485 | 1.95 (2) | method of Yung, D. K. et al.; J. Pharm. Sci.; EN; 57; 1968; 2073-2080. | 76 (97) |
| 160 | 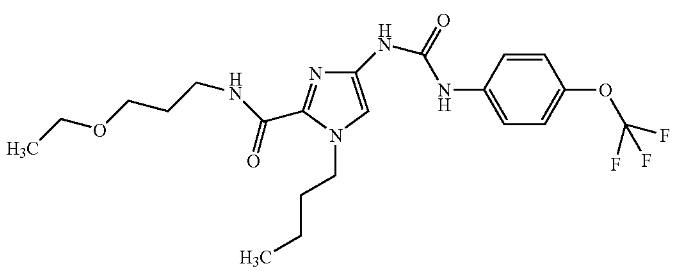 | 471.48 | 472 | 2.73 (2) | | 70 (99) |
| 161 | 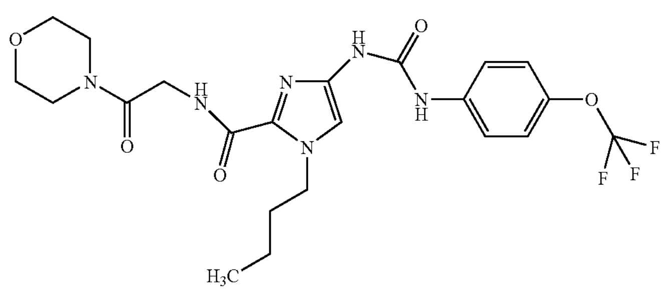 | 512.49 | 513 | 2.47 (2) | method of Venuti, Michael C.; Alvarez, Robert; Bruno, John J.; Strosberg, Arthur M.; Gu, Leo; J. Med. Chem.; 31; 11; 1988; 2145-2152. | 80 (quant.) |

TABLE 6-continued

| Example No. | Structure | Mol. mass | MS (EI) [M + H]+ | LC-MS retention time [min] (method) | Synthesis of the amine starting compound | Yield [mg] (% of theory) |
|---|---|---|---|---|---|---|
| 162 | 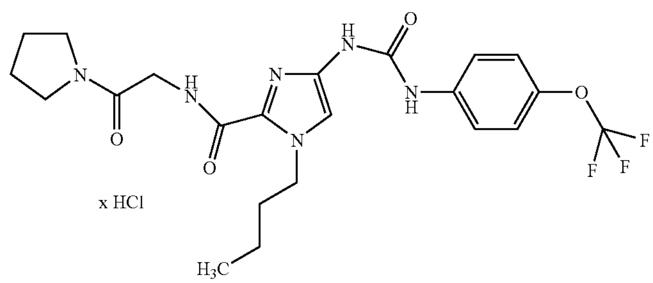 | 518.97 | 483 | 1.56 (4) | | 72 (92) |
| 163 | 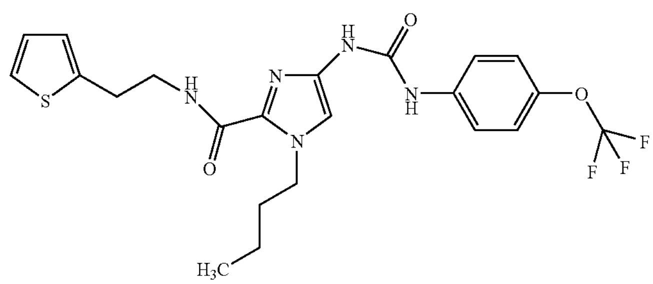 | 495.52 | 496 | 2.75 (4) | | 72 (97) |
| 164 | 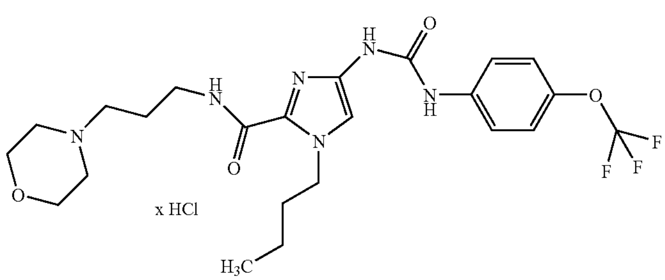 | 548.99 | 513 | 1.57 (4) | | 81 (98) |
| 165 | 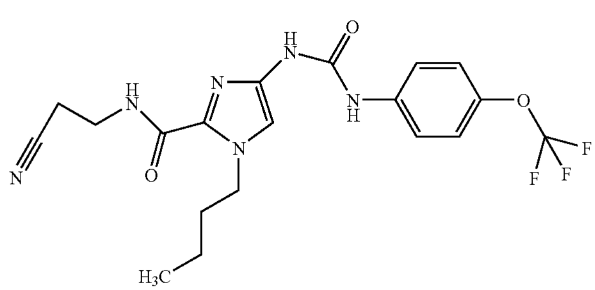 | 480.49 | 481 | 2.67 (5) | | 57 (79) |
| 166 | 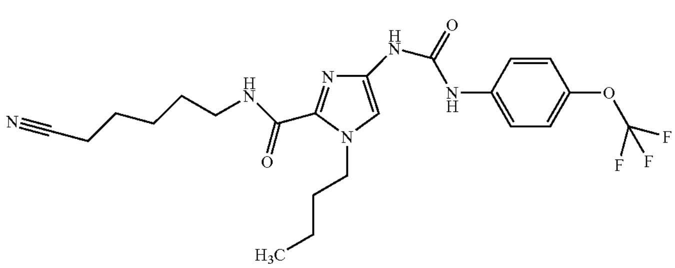 | 438.41 | 439 | 2.47 (4) | | 65 (98) |

TABLE 6-continued

| Example No. | Structure | Mol. mass | MS (EI) [M + H]+ | LC-MS retention time [min] (method) | Synthesis of the amine starting compound | Yield [mg] (% of theory) |
|---|---|---|---|---|---|---|
| 167 | 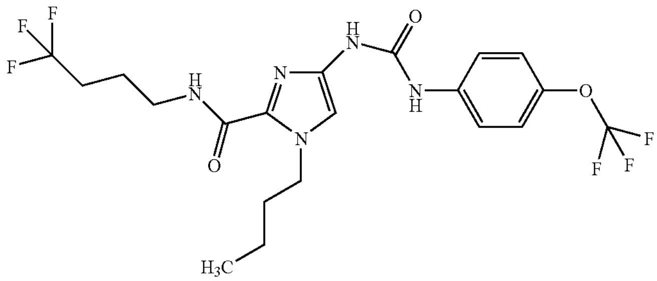 | 495.42 | 496 | 2.86 (5) | method of Raasch, M. S.; J. Org. Chem.; EN; 27; 1962; 1406-1409. | 65 (86) |
| 168 | 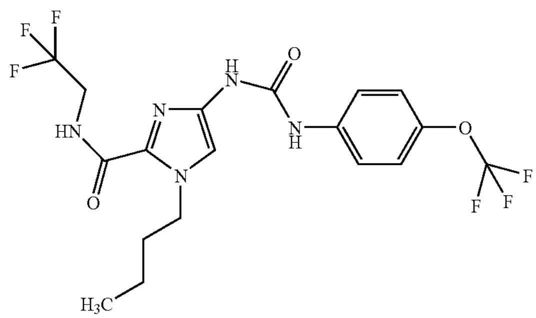 | 467.37 | 468 | 2.79 (5) | | 68 (97) |
| 169 | 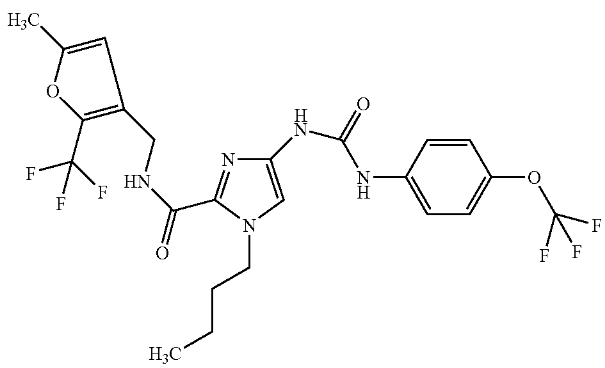 | 547.45 | 548 | 3.05 (2) | | 61 (84) |
| 170 | 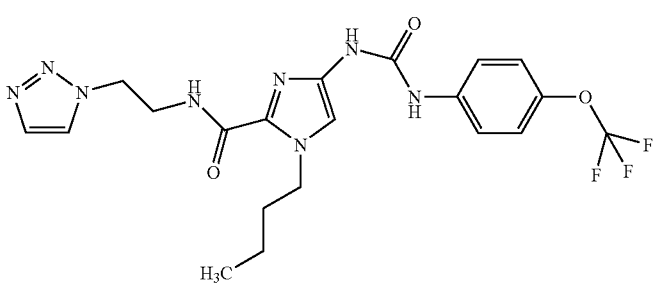 | 480.45 | 481 | 2.39 (5) | method of Sun, Li; Liang, Chris; Shirazian, Sheri; Zhou, Yong; Miller, Todd; Cui, Jean; Fukuda, Juri Y.; Chu, Ji-Yu; Nematalla, Asaad; Wang, Xueyan; Chen, Hui; et al. J. Med. Chem.; 46; 7; 2003; 1116-1119. | 61 (84) |

TABLE 6-continued

| Example No. | Structure | Mol. mass | MS (EI) [M + H]+ | LC-MS retention time [min] (method) | Synthesis of the amine starting compound | Yield [mg] (% of theory) |
|---|---|---|---|---|---|---|
| 171 | 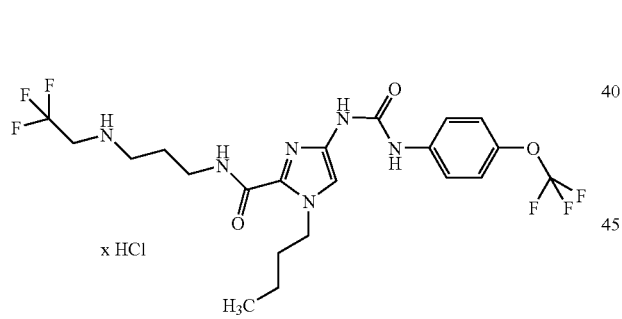 | 512.92 | 477 | 1.97 (5) | | 71 (92) |

Example 172

1-Butyl-N-{3-[(2,2,2-trifluoroethyl)amino]propyl}-4-[({[4-(trifluoromethoxy)phenyl]-amino}carbonyl)amino]-1H-imidazole-2-carboxamide Hydrochloride

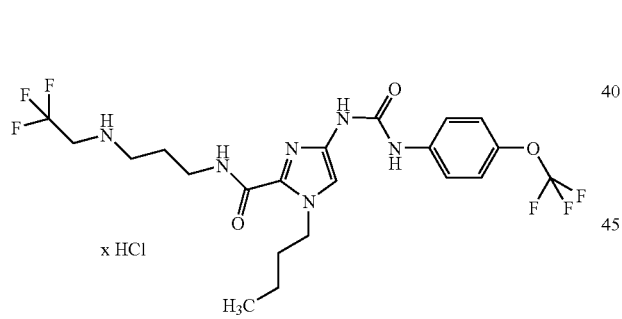

90 mg (0.19 mmol) of 1-butyl-N-(3-chloropropyl)-4-[({[4-(trifluoromethoxy)phenyl]-amino}carbonyl)amino]-1H-imidazole-2-carboxamide (Example 151) in 3 ml of 1,2-dimethoxyethane are mixed with 97 mg (0.97 mmol) of 2,2,2-trifluoroethylamine and 29 mg (0.19 mmol) of sodium iodide under argon and stirred at 90° C. overnight. The reaction mixture is concentrated in vacuo and purified by preparative HPLC.

Yield: 48 mg (40% of theory)

LC-MS (Method 2): $R_t$=2.15 min.

MS (ESI+): m/z=525 [M+H]+

Example 173

1-Butyl-N-[3-(1H-pyrazol-1-yl)propyl]-4-[({[4-(trifluoromethyl)phenyl]-amino}carbonyl)amino]-1H-imidazole-2-carboxamide

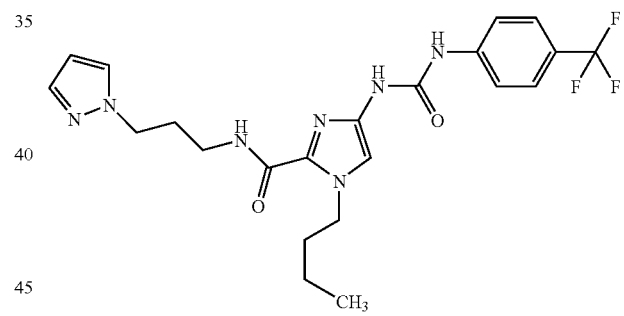

50 mg (0.14 mmol) of Example 30A are dissolved in 2 ml of DMF, and 65 mg (0.2 mmol) of O-(benzotriazol-1-yl)-N,N,N',N'-tetramethyluronium tetrafluoroborate (TBTU) and 25 mg (0.2 mmol) of 4-dimethylaminopyridine are added. Addition of 34 mg (0.27 mmol) of 3-(1H-pyrazol-1-yl)propylamine is followed by stirring at RT for 12 h. The reaction mixture is purified by RP-HPLC.

Yield: 38 mg (59% of theory)

LC-MS (Method 4): $R_t$=2.38 min.

MS (ESI+): m/z=478 [M+H]+

$^1$H-NMR (300 MHz, DMSO-$d_6$): δ=9.29 (bs, 1H), 8.79 (bs, 1H), 8.28 (t, 1H), 7.75 (d, 1H), 7.67 (d, 2H), 7.62 (d, 2H), 7.44 (d, 1H), 7.26 (s, 1H), 6.23 (t, 1H), 4.39 (t, 2H), 4.15 (t, 2H), 3.21 (q, 2H), 1.99 (quint, 2H), 1.68 (quint, 2H), 1.25 (sext, 2H), 0.88 (t, 3H).

The examples listed in Table 7 are prepared in analogy to Example 173.

TABLE 7

| Ex. No. | Structure | Mol. mass | MS (ESI) [M + H]+ | LC-MS R_t [min] (method) | Starting compound | Yield [mg] of (% theory) |
|---|---|---|---|---|---|---|
| 174 | 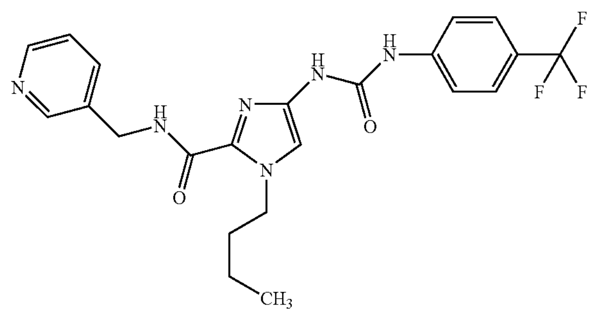 | 460.46 | 461 | 1.98 (4) | Example 30A | 38 (61) |
| 175 | 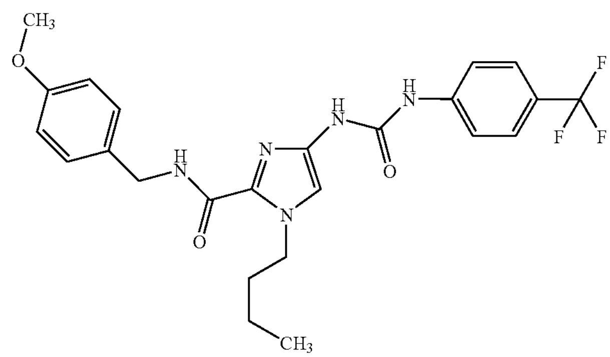 | 489.49 | 490 | 2.67 (4) | Example 30A | 38 (57) |
| 176 | 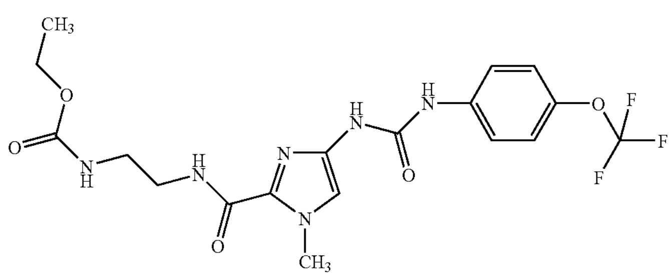 | 458.39 | 459 | 2.21 (2) | Example 29A | 51 (77) |
| 177 | 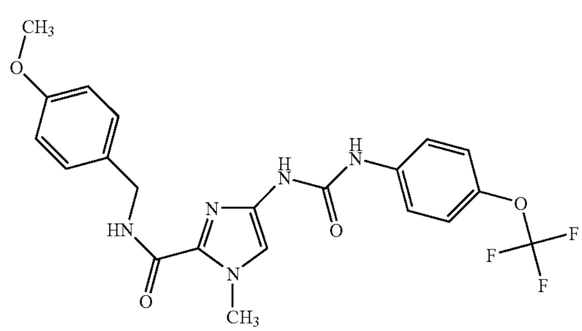 | 463.41 | 464 | 2.59 (2) | Example 29A | 66 (95) |

TABLE 7-continued

| Ex. No. | Structure | Mol. mass | MS (ESI) [M + H]+ | LC-MS R_t [min] (method) | Starting compound | Yield [mg] of (% theory) |
|---|---|---|---|---|---|---|
| 178 | 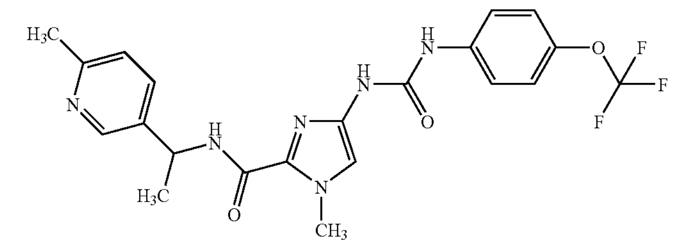 | 462.43 | 463 | 1.61 (4) | Example 29A | 75 (28) |
| 179 | 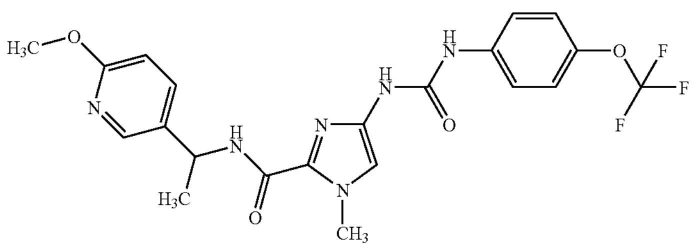 | 478.43 | 479 | 2.42 (2) | Example 29A | 62 (89) |
| 180 | 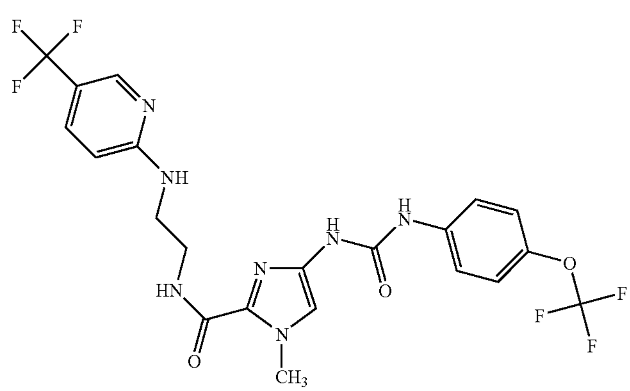 | 531.42 | 532 | 2.50 (2) | Example 29A | 72 (93) |
| 181 | 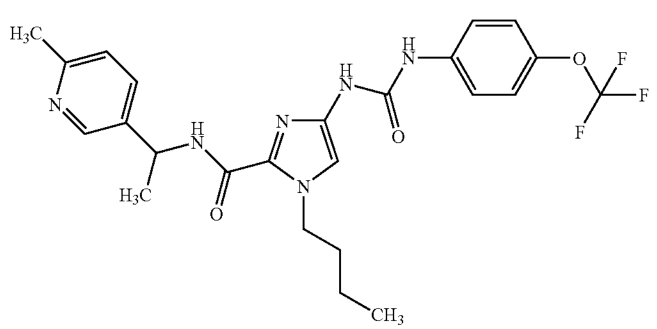 | 504.51 | 505 | 2.15 (5) | Example 7A | 33 (13) |

TABLE 7-continued

| Ex. No. | Structure | Mol. mass | MS (ESI) [M + H]+ | LC-MS R_t [min] (method) | Starting compound | Yield [mg] of (% theory) |
|---|---|---|---|---|---|---|
| 182 | 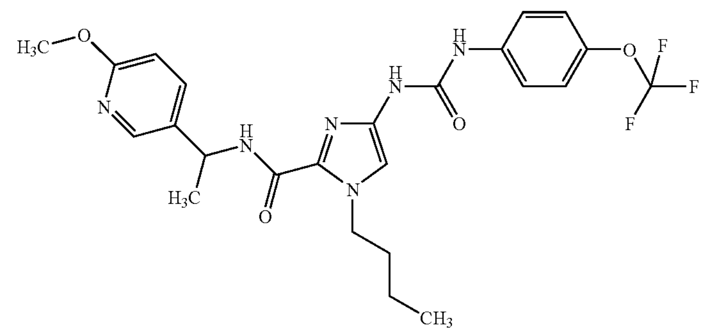 | 520.51 | 521 | 2.77 (2) | Example 7A | 45 (67) |
| 183 | 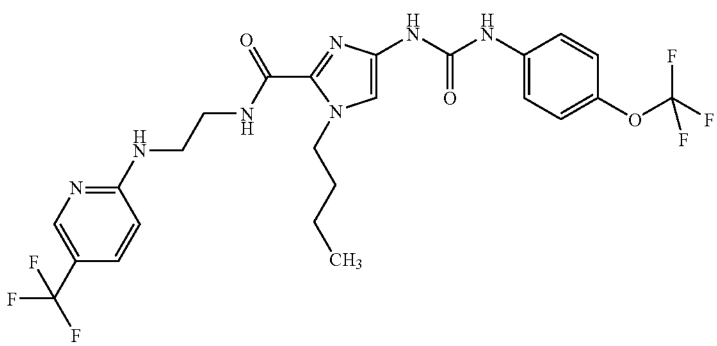 | 573.49 | 574 | 2.82 (2) | Example 7A | 64 (86) |
| 184 | 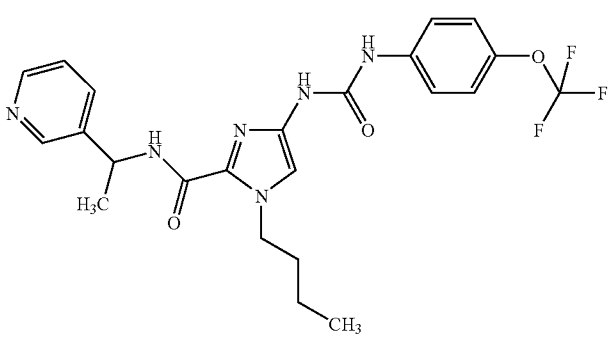 | 490.48 | 491 | 2.32 (5) | Example 7A | 20 (8) |

The examples in Table 8 are prepared in analogy to Example 1.

TABLE 8

| Ex. No. | Structure | Mol. mass | MS (ESI) [M + H]⁺ | HPLC $R_t$ [min] (method) | Starting compound | Yield [mg] (% of theory) |
|---|---|---|---|---|---|---|
| 185 | 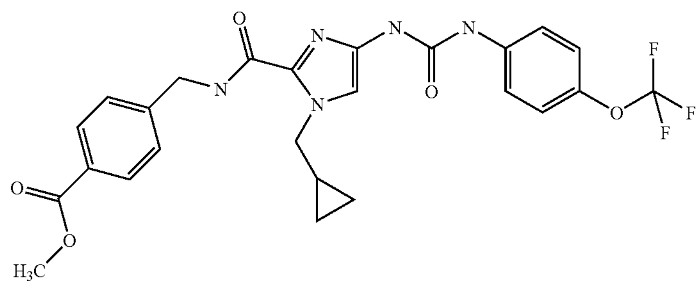 | 531.49 | 532 | 4.96 (11) | Example 5A | 64 (29) |
| 186 | 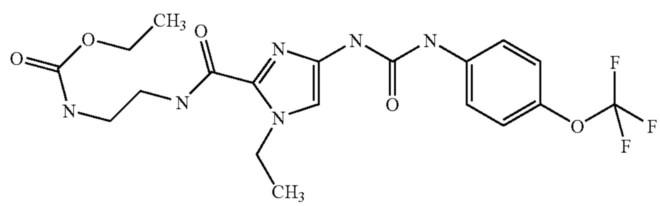 | 472.43 | 473 | 4.39 (11) | Example 31A | 23 (35) |
| 187 | 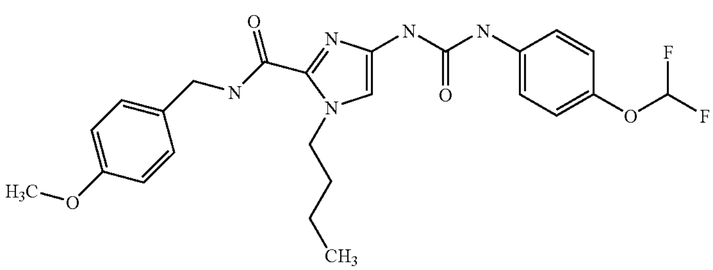 | 487.51 | 488 | 4.83 (11) | Example 33A | 35 (52) |
| 188 | 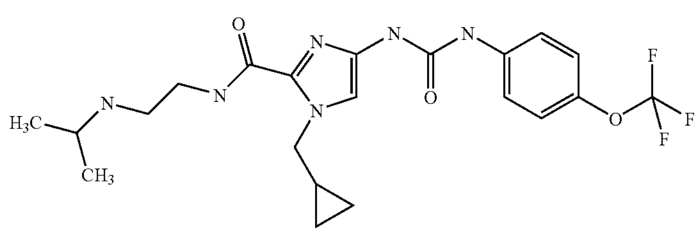 | 468.48 | 469 | 4.40 (11) | Example 5A | 13 (30) |
| 189 | 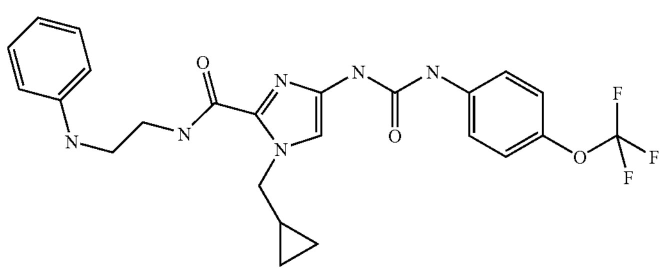 | 502.50 | 503 | 4.54 (11) | Example 5A | 20 (38) |

TABLE 8-continued

| Ex. No. | Structure | Mol. mass | MS (ESI) [M + H]+ | HPLC Rt [min] (method) | Starting compound | Yield [mg] (% of theory) |
|---|---|---|---|---|---|---|
| 190 | 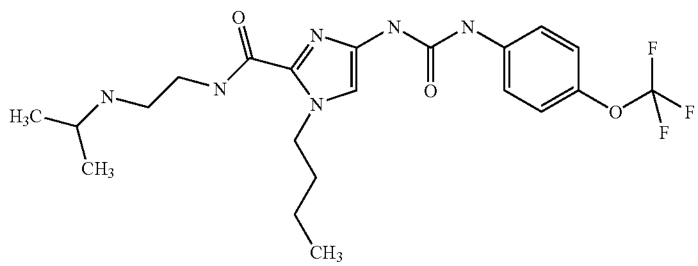 | 470.50 | 471 | 4.51 (11) | Example 7A | 12 (28) |
| 191 | 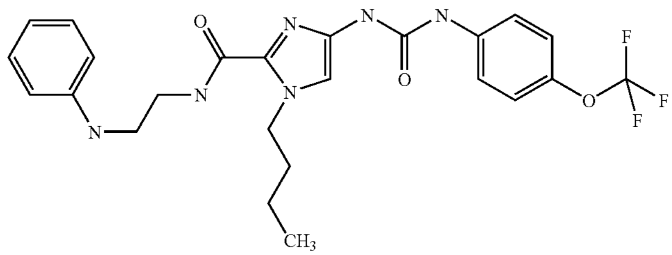 | 504.52 | 505 | 4.71 (11) | Example 7A | 20 (38) |
| 192 | 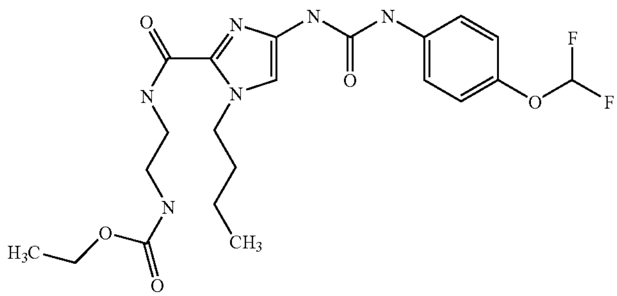 | 482.49 | 483 | 4.46 (11) | Example 33A | 49 (79) |
| 193 | 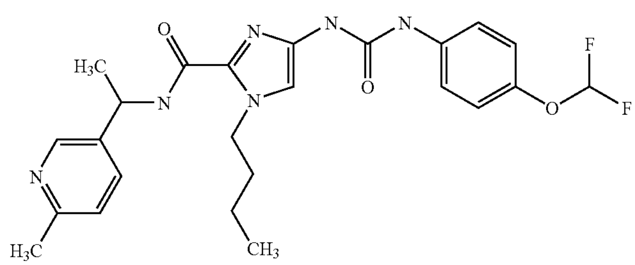 | 486.53 | 487 | 4.23 (11) | Example 33A | 26 (59) |
| 194 | 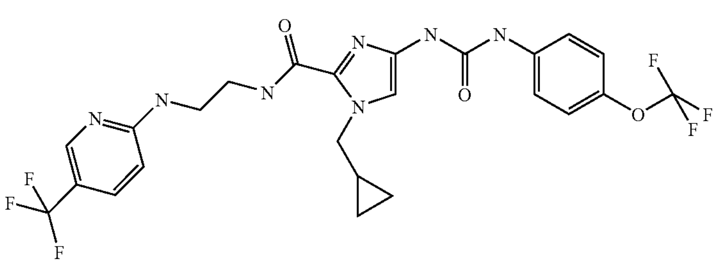 | 571.49 | 572 | 4.62 (11) | Example 5A | 42 (81) |

B. ASSESSMENT OF THE PHYSIOLOGICAL ACTIVITY

The in vitro effect of the compounds of the invention can be shown in the following assays:

Anti-HCMV (Anti-human Cytomegalovirus) Cytopathogenicity Tests

The test compounds are employed as 50 millimolar (mM) solutions in dimethyl sulphoxide (DMSO). Ganciclovir, foscarnet and cidofovir are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. 150 µl of a suspension of $1 \times 10^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% $CO_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (plaque multiplier from Technomara).

The following data can be acquired from the test plates:

$CC_{50}$ (NHDF)=substance concentration in µM at which no visible cytostatic effects on the cells are evident by comparison with the untreated cell control;

$EC_{50}$ (HCMV)=substance concentration in VM which inhibits the CPE (cytopathic effect) by 50% compared with the untreated virus control;

SI (selectivity index)=$CC_{50}$ (NHDF)/$EC_{50}$ (HCMV).

Representative in vitro data for the effects of the compounds of the invention are shown in Table A:

TABLE A

| Example-Nr. | NHDF $CC_{50}$ [nM] | HCMV $EC_{50}$ [nM] | SI HCMV |
|---|---|---|---|
| 2 | 94 000 | 0.5 | 188 000 |
| 3 | 25 000 | 3.0 | 8333 |
| 11 | 25 000 | 1.0 | 25 000 |
| 25 | 6250 | 1.0 | 6250 |
| 32 | 3130 | 1.0 | 3130 |
| 124 | 9400 | 1.4 | 6714 |
| 139 | 4700 | 2.8 | 1679 |
| 152 | 31 000 | 1.9 | 16 316 |

The suitability of the compounds of the invention for the treatment of HCMV infections can be shown in the following animal models:

HCMV Xenograft Gelfoam® Model

Animals:

3-4-week old female immunodeficient mice (16-18 g), Fox Chase SCID or Fox Chase SCID-NOD or SCID beige, are purchased from commercial breeders (Bomholtgaard, Jackson). The animals are housed under sterile conditions (including bedding and feed) in isolators.

Virus Growing:

Human cytomegalovirus (HCMV), Davis strain, is grown in vitro on human embryonic prepuce fibroblasts (NHDF cells). After the NHDF cells have been infected with a multiplicity of infection (M.O.I.) of 0.01, the virus-infected cells are harvested 5-7 days later and stored in the presence of minimal essential medium (MEM), 10% fetal calf serum (FCS) with 10% DMSO at −40° C. After serial ten-fold dilutions of the virus-infected cells, the titre is determined on 24-well plates of confluent NHDF cells after vital staining with neutral red or fixation and staining with a formalin-Giemsa mixture (as described above).

Preparation of the Sponges, Transplantation, Treatment and Evaluation:

Collagen sponges 1×1×1 cm in size (Gelfoam®; from Peasel & Lorey, order No. 407534; K. T. Chong et al., Abstracts of 39th Interscience Conference on Antimicrobial Agents and Chemotherapy, 1999, p. 439, P. M. Kraemer et al., Cancer Research 1983, (43): 4822-4827) are initially wetted with phosphate-buffered saline (PBS), the trapped air bubbles are removed by degassing, and then stored in MEM+10% FCS. $1 \times 10^6$ virus-infected NHDF cells (infection with HCMV Davis M.O.I.=0.01) are detached 3 hours after infection and added in a drop of 20 µl of MEM, 10% of FCS, to a moist sponge. Optionally, 12-13 hours later, the infected sponges are incubated with 25 µl of PBS/0.1% BSA/1 mM DTT with 5 ng/µl basic fibroblast growth factor (bFGF). For the transplantation, the immunodeficient mice are anaesthetized with Avertin or with a mixture of azepromazine-xylazine and ketamine, the fur on the back is removed using a dry shaver, the epidermis is opened 1-2 cm, unstressed and the moist sponges are transplanted under the dorsal skin. The surgical wound is closed with tissue glue. 24 hours after the transplantation, the mice are treated with substance orally three times a day (7.00 h and 14.00 h and 19.00 h), twice a day (8.00 h and 17.00 h) or once a day (14.00 h) for a period of 8 days. The dose is 3 or 10 or 30 or 100 mg/kg of body weight, the volume administered is 10 ml/kg of body weight. The substances are formulated in the form of a 0.5% strength Tylose suspension with 2% DMSO. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% fetal calf serum, 10% DMSO at −140° C. Evaluation takes place after serial ten-fold dilution of the virus-infected cells by determining the titre on 24-well plates of confluent NHDF cells after vital staining with neutral red or fixation and staining with a formalin-Giemsa mixture (as described above). The number of infectious virus particles after the substance treatment compared with the placebo-treated control group is determined.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of Example 1, 50 mg of lactose (monohydrate), 50 mg of maize starch (native), 10 mg of polyvinylpyrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension which can be Administered Orally:

Composition:

1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.

Production:

The Rhodigel is suspended in ethanol, and the active ingredient is added to the suspension. The water is added while stirring. The mixture is stirred for about 6 h until the swelling of the Rhodigel is complete.

Solution which can be Administered Intravenously:

Composition:

1 mg of the compound of Example 1, 15 g of polyethylene glycol 400 and 250 g of water for injections.

Production:

The compound of the invention is dissolved together with polyethylene glycol 400 in the water with stirring. The solution is sterilized by filtration (pore diameter 0.22 μm) and dispensed under aseptic conditions into heat-sterilized infusion bottles. These are closed with infusion stoppers and crimped caps.

The invention claimed is:

1. A compound of the formula

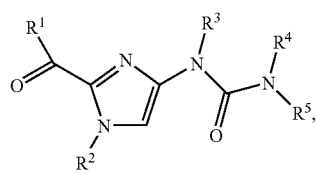

(I)

in which $R^1$ is $—OR^6$ or $—NR^7R^8$, $R^2$ is $C_1$-$C_6$-alkyl or $C_1$-$C_6$-alkenyl, where alkyl and alkenyl may be substituted by 1 to 3 substituents, where the substituents are selected independently of one another from the group consisting of halogen, $C_1$-$C_6$-alkoxy, $C_3$-$C_8$-cycloalkyl, 5- to 10-membered heterocyclyl, $C_6$-$C_{10}$-aryl, phenoxy and 5- to 10-membered heteroaryl, in which cycloalkyl, heterocyclyl, aryl, phenoxy and heteroaryl may be substituted by 1 to 3 substituents, where the substituents are selected independently of one another from the group consisting of halogen, hydroxy, oxo, nitro, cyano, trifluoromethyl, difluoromethyl, trifluoromethoxy, difluoromethoxy, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylaminocarbonyl and phenyl, $R^3$ and $R^4$ are independently of one another hydrogen or $C_1$-$C_6$-alkyl, $R^5$ is phenyl, where phenyl may be substituted by 1 to 3 substituents, where the substituents are selected independently of one another from the group consisting of halogen, hydroxy, trifluoromethyl, difluoromethyl, trifluoromethoxy, difluoromethoxy, $C_1$-$C_6$-alkyl and $C_1$-$C_6$-alkoxy, $R^6$ is $C_1$-$C_6$-alkyl, where alkyl may be substituted by 1 to 3 substituents, where the substituents are selected independently of one another from the group consisting of halogen, cyano, hydroxy, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclyl, 5- to 7-membered heterocyclylcarbonyl, $C_6$-$C_{10}$-aryl and 5- to 10-membered heteroaryl, in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, nitro, cyano, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_8$-cycloalkylamino and 5- to 7-membered heterocyclyl, in which heterocyclyl in turn may be substituted by 1 to 3 substituents, where the substituents are selected independently of one another from the group consisting of $C_1$-$C_4$-alkyl and oxo, $R^7$ is hydrogen or $C_1$-$C_6$-alkyl, and $R^8$ is $C_1$-$C_6$-alkyl, where alkyl may be substituted by 1 to 3 substituents, where the substituents are selected independently of one another from the group consisting of halogen, cyano, hydroxy, trifluoromethyl, $C_1$-$C_6$-alkoxy, hydroxycarbonyl, $C_1$-$C_6$-alkoxycarbonyl, amino, $C_1$-$C_6$-alkylamino, aminocarbonyl, $C_1$-$C_6$-alkylcarbonyloxy, $C_1$-$C_6$-alkylcarbonylamino, $C_1$-$C_6$-alkylaminocarbonyl, $C_1$-$C_6$-alkoxycarbonylamino, $C_3$-$C_8$-cycloalkyl, $C_3$-$C_8$-cycloalkylamino, 5- to 10-membered heterocyclyl, 5- to 7-membered heterocyclylcarbonyl, $C_6$-$C_{10}$-aryl, $C_6$-$C_{10}$-arylamino, 5- to 10-membered heteroaryl and 5- to 10-membered heteroarylamino, in which alkoxy and alkylamino may be substituted by 1 to 3 substituents, where the substituents are selected independently of one another from the group consisting of halogen, hydroxy and $C_1$-$C_6$-alkoxy, and in which cycloalkyl, cycloalkylamino, heterocyclyl, heterocyclylcarbonyl, aryl, arylamino, heteroaryl and heteroarylamino may be substituted by 1 to 3 substituents, where the substituents are selected independently of one another from the group consisting of halogen, hydroxy, oxo, nitro, cyano, trifluoromethyl, difluoromethyl, trifluoromethoxy, difluoromethoxy, $C_1$-$C_6$-alkyl, $C_1$-$C_6$-alkoxy, hydroxycarbonyl, $C_1$-$C_6$-alkoxycarbonyl, amino, $C_1$-$C_6$-alkylamino, aminocarbonyl and $C_1$-$C_6$-alkylaminocarbonyl, and in which alkylcarbonyloxy may be substituted by 1 to 3 substituents, Where the substituents are selected independently of one another from the group consisting of hydroxycarbonyl, amino, $C_1$-$C_6$-alkylamino, $C_3$-$C_8$-cycloalkylamino and 5- to 7-membered heterocyclyl,
in which heterocyclyl in turn may be substituted by 1 to 3 substituents, where the substituents are selected independently of one another from the group consisting of $C_1$-$C_4$-alkyl and oxo, or a salt thereof.

2. The compound according to claim 1, characterized in that $R^1$ is —$OR^6$ or —$NR^7R^8$, $R^2$ is $C_1$-$C_4$-alkyl or $C_1$-$C_5$-alkenyl,
where alkyl and alkenyl may be substituted by 1 to 2 substituents, where the substituents are selected independently of one another from the group consisting of halogen, $C_1$-$C_4$-alkoxy, $C_3$-$C_6$-cycloalkyl, phenyl and phenoxy,
in which cycloalkyl, phenyl and phenoxy may be substituted by 1 to 3 substituents, where the substituents are selected independently of one another from the group consisting of halogen, hydroxy, cyano, trifluoromethyl, trifluoromethoxy, $C_6$-$C_4$-alkyl, $C_1$-$C_4$-alkoxy, hydroxycarbonyl, $C_6$-$C_4$-alkoxycarbonyl, amino, $C_6$-$C_6$-alkylamino, aminocarbonyl, $C_6$-$C_6$-alkylaminocarbonyl and phenyl, $R^3$ and $R^4$ are hydrogen, $R^5$ is phenyl,
where phenyl may be substituted by 1 to 3 substituents, where the substituents are selected independently of one another from the group consisting of halogen, hydroxy, trifluoromethyl, trifluoromethoxy, $C_1$-$C_4$-alkyl and $C_6$-$C_4$-alkoxy, $R^6$ is $C_1$-$C_5$-alkyl,
where alkyl may be substituted by 1 to 3 substituents, where the substituents are selected independently of one another from the group consisting of halogen, cyano, hydroxy, $C_6$-$C_4$-alkoxy, hydroxycarbonyl, amino, $C_6$-$C_6$-alkylamino, aminocarbonyl, $C_6$-$C_4$-alkylcarbonyloxy, $C_6$-$C_4$-alkylcarbonylamino, $C_1$-$C_6$-alkylaminocarbonyl, $C_6$-$C_4$-alkoxycarbonylamino, $C_3$-$C_7$-cycloalkyl, $C_3$-$C_7$-cycloalkylamino, 5- to 7-membered heterocyclyl, 5- to 7-membered heterocyclylcarbonyl, $C_6$-$C_{10}$-aryl and 5- to 10-membered heteroaryl,
in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, cyano, $C_1$-$C_4$-alkyl, $C_1$-$C_4$-alkoxy, hydroxycarbonyl, $C_6$-$C_4$-alkoxycarbonyl, amino, $C_6$-$C_6$-alkylamino, aminocarbonyl and $C_6$-$C_6$-alkylaminocarbonyl,
and
in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_7$-cycloalkylamino and 5- to 7-membered heterocyclyl,
in which heterocyclyl in turn may be substituted by 1 to 3 substituents, where the substituents are selected independently of one another from the group consisting of $C_1$-$C_4$-alkyl and oxo, $R^7$ is hydrogen,
and $R^8$ is $C_1$-$C_5$-alkyl,
where alkyl may be substituted by 1 to 3 substituents, where the substituents are selected independently of one another from the group consisting of halogen, cyano, hydroxy, trifluoromethyl, $C_1$-$C_6$-alkoxy, hydroxycarbonyl, amino, $C_1$-$C_6$-alkylamino, aminocarbonyl, $C_6$-$C_4$-alkylcarbonyloxy, $C_6$-$C_4$-alkylcarbonylamino, $C_1$-$C_4$-alkylaminocarbonyl, $C_6$-$C_6$-alkylaminocarbonyl, $C_1$-$C_4$-alkoxycarbonylamino, $C_3$-$C_7$-cycloalkyl, $C_3$-$C_7$-cycloalkylamino, 5- to 7-membered heterocyclyl, 5- to 7-membered heterocyclylcarbonyl, $C_6$-$C_{10}$-aryl and 5- to 10-membered heteroaryl,
in which alkoxy and alkylamino may be substituted by 1 to 3 substituents, where the substituents are selected independently of one another from the group consisting of halogen, hydroxy and $C_1$-$C_4$-alkoxy,
and
in which cycloalkyl, cycloalkylamino, heterocyclyl, heterocyclylcarbonyl, aryl and heteroaryl may be substituted by 1 to 3 substituents, where the substituents are selected independently of one another from the group consisting of halogen, hydroxy, oxo, cyano, trifluoromethyl, $C_1$-$C_4$-alkyl, $C_6$-$C_4$-alkoxy, hydroxycarbonyl, $C_1$-$C_4$-alkoxycarbonyl, amino, $C_1$-$C_6$-alkylamino, aminocarbonyl and $C_6$-$C_6$-alkylaminocarbonyl,
and
in which alkylcarbonyloxy may be substituted by 1 to 3 substituents, where the substituents are selected independently of one another from the group consisting of hydroxycarbonyl, amino, $C_1$-$C_6$-alkylamino, $C_3$-$C_7$-cycloalkylamino and 5- to 7-membered heterocyclyl,
in which heterocyclyl in turn may be substituted by 1 to 3 substituents, where the substituents are selected independently of one another from the group consisting of $C_1$-$C_4$-alkyl and oxo.

3. The compound according to claim 1 or 2, characterized in that $R^1$ is —$OR^6$ or —$NR^7R^8$, $R^2$ is methyl, ethyl, n-butyl, prop-2-en-1-yl or 3-methyl-but-2-en-1-yl,
where methyl, ethyl, n-butyl and prop-2-en-1-yl may be substituted by 1 to 2 substituents, where the substituents are selected independently of one another from the group consisting of chlorine, methoxy, cyclopropyl, phenyl and phenoxy,
in which phenyl may be substituted by a substituent trifluoromethyl, $R^3$ and $R^4$ are hydrogen, $R^5$ is phenyl,
where phenyl may be substituted by 1 to 3 substituents, where the substituents are selected independently of one another from the group consisting of fluorine, chlorine, trifluoromethoxy and methyl, $R^6$ is $C_1$-$C_3$-alkyl,
where alkyl may be substituted by 1 to 2 substituents, where the substituents are selected independently of one another from the group consisting of halogen, cyano, hydroxy and methylcarbonyloxy,
in which methylcarbonyloxy may be substituted by 1 to 3 substituents, where the substituents are selected independently of one another from the group consisting of isobutylamino, dimethylamino, diethylamino, cyclopropylamino, pyrrolidinyl and morpholinyl, $R^7$ is hydrogen,
and $R^8$ is $C_1$-$C_3$-alkyl, where alkyl may be substituted by 1 to 2 substituents, where the substituents are selected independently of one another from the group consisting of halogen, cyano, hydroxy, trifluoromethyl, ethoxy, isobutylamino, dimethylamino, diethylamino, methylethylamino, aminocarbonyl, methylcarbonyloxy, propylcarbonyloxy, dimethylaminocarbonyl, diethylaminocarbonyl, ethoxycarbonylamino, cyclopropylamino, pyrrolidinyl, piperidinyl, morpholinyl, phenyl, thienyl, pyrazolyl, imidazolyl, triazolyl, pyridyl and benzimidazolyl, in which ethoxy and methylethylamino may be substituted by a substituent, where the substituent is selected from the group consisting of hydroxy and methoxy, and in which phenyl, pyrazolyl, imidazolyl, pyridyl and benzimidazolyl may be substituted by 1 to 3 substituents, where the substituents are selected independently of one another from the group consisting of methyl and methoxy, and in which methylcarbonyloxy and propylcarbonyloxy may be substituted by 1 to 3 substituents, where the substituents are selected independently of one another from the group consisting of hydroxycarbonyl, amino, isobutylamino, dimethylamino, diethylamino, cyclopropylamino, pyrrolidinyl and morpholinyl.

4. A process for preparing a compound of the formula (I) according to claim 1, characterized in that in process [A]

a compound of the formula

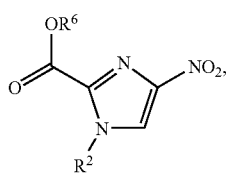

(IIa)

in which $R^6$ has the meaning indicated in claim 1, and $R^2$ has the meaning indicated in claim 1, is reacted in the first stage with a reducing agent, in the second stage where appropriate with a compound of the formula $X^1$—$R^3$ (III), in which $R^3$ has the meaning indicated in claim 1, and $X^1$ is halogen, preferably bromine or chlorine, and in the third stage in the presence of a carbonic acid derivative with a compound of the formula

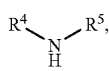

(IV)

in which $R^4$ $R^5$ have the meaning indicated in claim 1, to give a compound of the formula

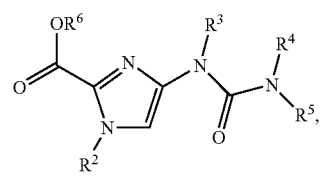

(Ia)

in which $R^6$ has the same meaning as in formula (IIa), and $R^2$, $R^3$, $R^4$ and $R^5$ have the meaning indicated in claim 1, or in process [B]

a compound of the formula (Ia), in which $R^8$ is methyl or ethyl, is reacted in the presence of a base to give a compound of the formula

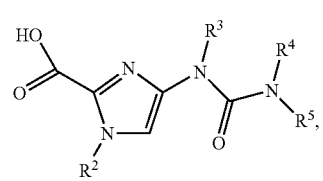

(Ib)

in which $R^2$, $R^3$, $R^4$ and $R^5$ have the meaning indicated in claim 1, or in process [C]

a compound of the formula (Ib) is reacted with a compound of the formula $R^1$—H (V), in which $R^1$ has the meaning indicated in claim 1, in the presence of dehydrating reagents to give a compound of the formula (I), or in process [D]

a compound of the formula

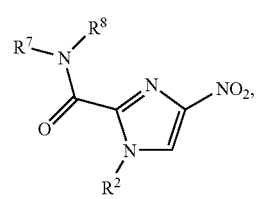

(IIb)

in which $R^2$, $R^7$ and $R^8$ have the meaning indicated in claim 1, is reacted in the first stage with a reducing agent, in the second stage where appropriate with a compound of the formula (III)

and in the third stage in the presence of a carbonic acid derivative with a compound of the formula (IV)

to give a compound of the formula

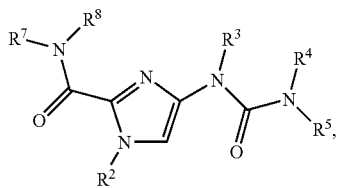

(Ic)

in which
R², R³, R⁴, R⁵, R⁷ and R⁸ have the meaning indicated in claim 1,
or
in process [E]
a compound of the formula (IIA) or (IIb)
is reacted in the first stage with a reducing agent,
in the second stage where appropriate with a compound of the formula (III)
and in the third stage with a compound of the formula

OCN—R⁵ (VI), in which
R⁵ has the meaning indicated in claim 1,
to give a compound of the formula

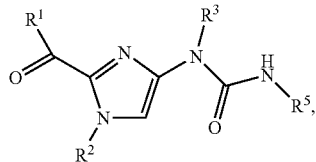

(Id)

in which
R¹, R², R³ and R⁵ have the meaning indicated in claim 1.

5. A pharmaceutical composition comprising a compound according to claim 1 in combination with at least one inert, non-toxic, pharmaceutically acceptable excipient.

6. A method for treating an infection with a cytomegalovirus in a human or animal comprising administering to said human or animal an antivirally effective amount of at least one compound according to claim 1 or at least one composition according to claim 5.

7. The method according to claim 6 wherein the cytomegalovirus is human cytomegalovirus (HCMV).

* * * * *